United States Patent
Port-Louis et al.

(10) Patent No.: US 11,751,573 B2
(45) Date of Patent: Sep. 12, 2023

(54) SEAWEED COMPOSITION

(71) Applicants: Bernard Port-Louis, Eve Island (SC); Benjamin Port-Louis, Eve Island (SC)

(72) Inventors: Bernard Port-Louis, Eve Island (SC); Benjamin Port-Louis, Eve Island (SC)

(*) Notice: Subject to any disclaimer, the term of this patent is extended or adjusted under 35 U.S.C. 154(b) by 428 days.

(21) Appl. No.: 16/764,919

(22) PCT Filed: Nov. 16, 2018

(86) PCT No.: PCT/AU2018/000224
§ 371 (c)(1),
(2) Date: May 18, 2020

(87) PCT Pub. No.: WO2019/095002
PCT Pub. Date: May 23, 2019

(65) Prior Publication Data
US 2020/0337315 A1 Oct. 29, 2020

(30) Foreign Application Priority Data

Nov. 17, 2017 (AU) .............................. 2017904664
Apr. 30, 2018 (AU) .............................. 2018901437

(51) Int. Cl.
*A01N 65/03* (2009.01)
*C05F 11/10* (2006.01)

(52) U.S. Cl.
CPC .............. *A01N 65/03* (2013.01); *C05F 11/10* (2013.01)

(58) Field of Classification Search
CPC ................................ A01N 65/03; C05F 11/10
USPC ............................................................ 504/117
See application file for complete search history.

(56) References Cited

U.S. PATENT DOCUMENTS

| | | | |
|---|---|---|---|
| 4,897,266 | A | 1/1990 | Herve et al. |
| 5,201,930 | A | 4/1993 | Campell |
| 2014/0105929 | A1 | 4/2014 | Wong et al. |
| 2017/0246228 | A1 | 8/2017 | Yamaguchi |

FOREIGN PATENT DOCUMENTS

| | | |
|---|---|---|
| CN | 102584440 | 7/2012 |
| CN | 103304278 | 9/2013 |
| CN | 103772038 | 5/2014 |
| CN | 104892157 | 9/2015 |
| CN | 104945107 | 9/2015 |
| CN | 105859405 | 8/2016 |
| CN | 106565335 | 4/2017 |

OTHER PUBLICATIONS

Kuma et al., Effect of liquid seaweed fertilizer of Sargassum wightii grev. on the growth and biochemical content of green gram (*Vigna radiata* (L.) R. wilczek). Recent Research in Science and Technology 2012, 4(4): 40-45. (Year: 2012).*

Ramya et al. Biofertilizing Efficiency of Brown and Green Algae on Growth, Biochemical and Yield Parameters of *Cyamopsis Tetragonolaba* (L.) Taub. Recent Research in Science and Technology 2010, 2(5): 45-52. (Year: 2010).*

Zdarska et al. Proteome Analysis in *Arabidopsis* Reveals Shoot- and Root-Specific Targets of Cytokinin Action and Differential Regulation of Hormonal Homeostasis. Plant Physiol. vol. 161, pp. 918-930, 2013. (Year: 2013).*

Stirk et al. Cytokinins in macroalgae. Plant Growth Regulation 41: 13-24, 2003. (Year: 2003).*

Atouani et al., "The invasive brown seaweed *Sargassum muticum* as new resource for alginate in Morocco: Spectroscopic and rheological characterization," Phycological Research, 64:185-93, 2016.

Eluvakkal et al., "Fucoidan in some Indian brown seaweeds found along the coast Gulf of Mannar," *International Journal of Botany*, 6(2):176-181, 2010.

Erulan et al., "Studies on the Effect of Sargassum polycystum (C.Agardh, 1824) Extract on the Growth and Biochemical Composition of *Cajanus cajan* (L.) Mill sp" American-Eurasian J. Agric. & Environ. Sci., 6(4):392-399. 2009.

Florez-Fernandez et al., "Ultrasound-assisted extraction of fucoidan from *Sargassum muticum*, " Journal of Applied Phycology, Ahead of Print, 2017.

Kumar et al., "Effect of liquid seaweed fertilizer of Sargassum wightii grev. on the growth and biochemical content of green gram (*Vigna radiata* (L.) R. wilczek)" Recent Research in Science and Technology, 4(4):40-45, 2012.

Kumar et al., "Fucoidan—A a-D-glucosidase inhibitor from *Sargassum wightii* with relevance to type 2 diabetes mellitus therapy", *International Journal of Biological Macromolecules*, 72:1044, 2015.

Kumareswari et al., "Nutritional superiority of seaweed based organic green leafy vegetable, *Amaranthus retroflexus* L." Journal of Pharma and Bio Sciences, 7(1):332-335, 2016.

Lim et al., "Chemical properties and toxicology studies of fucoidan extracted from Malaysian *Sargassum binderi*." Food Science and Biotechnology, 25(1): 23-29, 2016.

Office Communication issued in correspondence United Kingdom Application No. GB2009067.6 dated Feb. 21, 2022.

PCT International Search Report and Written Opinion issued in Australian Application No. 2017/904664 dated Nov. 17, 2017.

PCT International Search Report and Written Opinion issued in International Application No. PCT/AU2018/000224, dated Feb. 7, 2019.

Puspita et al., "Antioxidant and antibacterial activity of solid-liquid and enzyme-assisted extraction of phenolic compound from three species of tropical Sargassum", *IOP Conf. Ser.: Earth Environ. Sci.*, 55:012057, 2017.

(Continued)

*Primary Examiner* — Yih-Horng Shiao
(74) *Attorney, Agent, or Firm* — Parker Highlander PLLC

(57) ABSTRACT

A composition derived or derivable from seaweed is provided. The composition comprises one or more plant hormones; and/or one or more acidic polysaccharides. Also provided is a method for producing a composition, including the step of extracting one or more agents from seaweed. A method of stimulating plant growth by applying a composition derived or derivable from seaweed is also provided.

25 Claims, 30 Drawing Sheets

(56) References Cited

OTHER PUBLICATIONS

Sasikala et al., "Effect of Seaweed Extract (*Sargassum tenerrimum*) on Seed Germination and growth of Tomato Plant (*Solanum lycopersicum*)" *International Journal of Chem Tech Research*, 9(09): 285-293, 2016.

Selvam et al. "Micromorphological study of *Vigna mungo* L. using Seaweed liquid fertilizer from *Hypnea musciformis* (Wulf.) Lamouroux" *Indian Journal of Geo-Marine Science*, 45(9):1199-1207, 2016.

Sinha et al., "Polysaccharides from *Sargassum tenerrimum*: Structural features, chemical modification and anti-viral activity," *Phytochemistry*, 71(2-3):235-242, 2010.

Sivasankari et al., "Effect of seaweed extracts on the growth and biochemical constituents of Vigna sinensis" *Bioresource technology*, 97(14):1745-1751, 2006.

Somasundaram et al., "Cytotoxic effect of fucoidan extracted from *Sargassum cinereum* on colon cancer cell line HCT-15", *International Journal of Biological Macromolecules*, 91:1215-1223, 2016.

Stirk et al., "Abscisic acid, gibberellins and brassinosteroids in Kelpak®, a commercial seaweed extract made from Ecklonia maxima," Journal of Applied Phycology, 26:561-567, 2014.

Vijayanand et al., "Potential of liquid extracts of Sargassum wightii on growth, biochemical and yield parameters of cluster bean plant", *Asian Pacific Journal of Reproduction*, 3(2):150-155, 2014.

Bhosle, N. B. et al., "Effect of Seaweed Extract on the Growth of *Phaseolus vulgaris* L.," *Indian J. Mar. Sci.*, 4 (1975): 208-210.

\* cited by examiner

| HORMONE | RETENTION TIME |
|---|---|
| indole-3-acetic acid (IAA) | 5.39-5.47 |
| indole-3-acetic acid ethyl ester (IAAEt) | 7.75-7.81 |
| indole-3-acetyl-glycine (IAGly) | 3.81-3.88 |
| indole-3-acetyl-L-alanine (IAAla) | 4.97-5.08 |
| indole-3-carboxylic acid (I3CA) | 4.99-5.15 |
| indole-3-carboxylic acid methyl ester (I3CAMe) | 6.99-7.07 |
| indole-3-propionic acid (IPA) | 6.45-6.48 |
| indole-3-butyric acid (IBA) | 7.19-7.27 |
| indole-3-pyruvic acid (IPiA) | 6.21-6.30 |
| indole-3-glyoxylic acid methyl ester (IGAMe) | 6.25-6.33 |
| DL-indole-3-lactic acid (ILA) | 4.73-4.79 |
| indole-3-carboxaldehyde (IAld) | 4.90-5.01 |
| indole-3-acetamide (IAM) | 3.34-3.38 |
| tryptophol (IEt) | 5.29-5.37 |
| N6-isopentenyladenine (iP) | 4.54-4.68 |
| N6-isopentenyladenosine (iPR) (riboprine) | 5.88-5.97 |
| *trans*-zeatin-9-glucoside (*t*Z9G) | 1.35-1.39 |
| *trans*-zeatin-O-glucoside (*t*ZOG) | 1.38-1.39 |
| *cis*-zeatin (*c*Z) | 1.45-1.69 |
| dihydrozeatin (DHZ) | 1.35-1.40 |
| N6-benzyladenine (BA) | 4.76-4.97 |
| N6-benzyladenosine (BAR) | 6.06-6.14 |
| *ortho*-topolin (*o*T) | 4.15-4.36 |
| *para*-topolin (*p*T) | 1.94-2.14 |
| gibberellin A3 (GA3) | 4.96-5.08 |
| gibberellin A6 (GA6) | 5.77-5.85 |
| gibberellin A7 (GA7) | 8.40-8.48 |
| salicylic acid (SA) | 5.58-5.76 |
| (+)-*cis,trans*-abscisic acid (ABA) | 6.73-6.81 |
| (-)-jasmonic acid (JA) | 7.42-7.50 |
| (-)-jasmonic acid methyl ester (MeJA) | 8.45-8.55 |

Figure 29

SEAWEED COMPOSITION

This application is a national phase application under 35 U.S.C. § 371 of International Application No. PCT/AU2018/000224, filed Nov. 16, 2018, which claims the benefit of Australian Patent Application No. 2017904664, filed Nov. 17, 2017, and Australian Patent Application No. 2018901437, filed Apr. 30, 2018, the entirety of each of which is incorporated herein by reference.

TECHNICAL FIELD

The present invention relates to seaweed compositions. More particularly, the invention relates to compositions comprising seaweed extracts that are suitable for stimulating plant growth, although without limitation thereto. The invention also relates to methods of extraction of desired agents from seaweed.

BACKGROUND

A variety of methods for encouraging plant growth are used, both in horticultural and agricultural industry, and for small-scale (e.g. home) gardening. Commonly, fertilisers are applied to plants, to provide desirable amounts of essential nutrients. Additionally, certain compositions including agents, such as plant hormones, that regulate plant growth are sometimes used for enhancing or otherwise modifying the growth of plants or plant parts.

Compositions are available for use in plant fertilisation and/or growth regulation, including some seaweed-based compositions. However, particularly in the case of seaweed-based compositions, there is limited information available regarding the specific benefits of these compositions, and the basis for such benefits. Similarly, very little information exists regarding particular combinations and amounts of various agents extractable from seaweed that may be optimal for encouraging plant growth.

Accordingly, it is desirable to identify new compositions derived or derivable from seaweed having particular amounts and/or combinations of agents that are beneficial for encouraging plant growth. New methods for producing such compositions are also desirable.

SUMMARY

This invention broadly provides compositions derived or derivable from seaweed. The invention further broadly provides methods for producing compositions, including the step of extracting one or more agents from seaweed. Also broadly provided are applications using compositions derived or derivable from seaweed, such as methods for stimulation of plant growth by applying said compositions to a plant.

In a first aspect, there is provided a composition derived or derivable from seaweed, the composition comprising:
 (a) one or more plant hormones; and/or
 (b) one or more acidic polysaccharides.

Preferably, the one or more plant hormones are selected from the group consisting of an auxin; a cytokinin; a phenolic plant hormone; an isoprenoid plant hormone; an aromatic plant hormone; and a lipid plant hormone, or analogues or derivatives thereof.

Preferably, the one or more auxins are selected from the group consisting of indole-3-acetic acid (IAA); indole-3-acetic acid ethyl ester; indole-3-acetyl-glycine (IAGly); indole-3-acetyl-L-alanine (IAAla); indole-3-carboxylic acid (I3CA); indole-3-carboxylic acid methyl; indole-3-butyric acid (IBA); indole-3-glyoxylic acid methyl ester; DL-indole-3-lactic acid (ILA); indole-3-carboxaldehyde (IAld); and tryptophol (IEt), or analogues or derivatives thereof.

Preferably, the one or more isoprenoid plant hormones is or includes an abscisic acid and/or an isoprenoid cytokinin, or analogues or derivatives thereof.

Preferably, the one or more abscisic acids is or includes (+)-cis, trans-abscisic acid (ABA) or analogues or derivatives thereof. Preferably, the one or more isoprenoid cytokinins is N6-isopentenyladenine (iP) and/or cis-zeatin (cZ), or analogues or derivatives thereof.

Preferably, the one or more aromatic plant hormones is or includes an aromatic cytokinin, or a derivative thereof. Preferably, the one or more aromatic cytokinins is selected from the group consisting of N6-benzyladenine (BA); ortho-topolin (oT); para-topolin (pT), or analogues or derivatives thereof.

Preferably, the one or more lipid plant hormones is or includes a jasmonate. Preferably, the one or more jasmonates is (−)-jasmonic acid (JA) and/or (−)-jasmonic acid methyl ester, or analogues or derivatives thereof.

Preferably, the one or more gibberellins is selected from the group consisting of gibberellin A3 (GA3); gibberellin A6 (GA6); and gibberellin A7 (GA7), or analogues or derivatives thereof.

Preferably, the one or more salicylates is or includes salicylic acid, or analogues or derivatives thereof.

Preferably, the concentration of each of the one or more plant hormones in the composition is between about 0.01 parts per billion (ppb), and about 1 part per million (ppm).

In preferred embodiments, the total concentration of all of said one or more plant hormones in the composition is between about 1.5 ppb and about 1.5 ppm.

In embodiments:
 the total concentration of auxins in the composition is between about 1 and about 1000 ppb;
 the total concentration of cytokinins in the composition is between about 0.1 and about 50 ppb;
 the total concentration of gibberellins in the composition is between about 0.005 and about 5 ppb;
 the total concentration of salicylates in the composition is between about 0.01 and about 20 ppb;
 the total concentration of abscisic acid in the composition is between about 0.1 and about 10 ppb; and/or
 the total concentration of jasmonate in the composition is between about 0.1 ppb and about 50 ppb.

In embodiments wherein the composition comprises one or more acidic polysaccharides, preferably the acidic polysaccharide is or includes an alginate; a fucoidan; an agar and/or a carrageenan, or analogues or derivatives thereof.

Suitably, the alginate comprises mannuronic acid and/or guluronic acid. Preferably, the alginate comprises mannuronic acid and guluronic acid.

Suitably, the fucoidan comprises fucose, and one or more of glucose, galactose and/or mannose. Preferably, the fucoidan comprises fucose, glucose, galactose and mannose.

Suitably, the agar comprises agarose and agaropectin.

Suitably, the carrageenan comprises galactose and/or 3,6-anhydrogalactose, Preferably, the carrageenan comprises galactose and 3,6-anhydrogalactose.

In some preferred embodiments, the concentration of each of said one or more acidic polysaccharides in the composition is between about 50 ppm to about 5 percent (%).

In a preferred embodiment, the concentration of alginate in the composition is between about 0.1% and about 5%.

In a preferred embodiment, the concentration of fucoidan in the composition is between about 50 ppm to about 5000 ppm.

In some preferred embodiments, the total concentration of said one or more acidic polysaccharides in the composition is between about 0.1% and about 10%.

In preferred embodiments, the composition is or includes an extract of a seaweed. Preferably, the extract is an aqueous extract.

In a preferred embodiment, the seaweed is a brown seaweed.

In embodiments wherein the seaweed is a brown seaweed, preferably the seaweed is of the order Fucales. More preferably, the seaweed is of the genus *Sargassum*. In a particularly preferred embodiment, the seaweed is of the species *Sargassum wightii*.

In a preferred embodiment, the seaweed is a red seaweed.

In embodiments wherein the seaweed is a red seaweed, preferably the seaweed is of the order Gigartinales. More preferably, the seaweed is of the genus *Hypnea*. In a particularly preferred embodiment, the seaweed is of the species *Hypnea musciformis*.

In a second aspect, the invention provides a method of producing a composition, the method including the step of obtaining an extract from a seaweed to thereby produce the composition.

In an embodiment, the method of this aspect includes the step of washing or rinsing the seaweed prior to obtaining an extract from the seaweed.

In one preferred embodiment, the washing or rinsing is washing or rinsing in a solution comprising salt. Preferably, the solution comprising salt is a salt water solution.

In one preferred embodiment, the washing or rinsing is washing or rinsing in pure, or substantially pure, water.

In preferred embodiments wherein the method includes the step of washing or rinsing the seaweed, the washing or rinsing is performed for between about 3 hours and about 24 hours, more preferably about 12 hours.

Preferably, the method of this aspect includes the step of combining the seaweed or an extract thereof with a liquid before and/or after obtaining the extract from the seaweed to produce the composition. Preferably, the liquid is water. In one preferred embodiment, the water is pure or substantially pure water.

Preferably, the ratio of seaweed or extract thereof to liquid that is combined according to the method of this aspect is between about 50 and about 200 grams seaweed per litre (g/L), more preferably about 100 g/L.

Preferably, obtaining an extract from the seaweed according to the method of this aspect includes the step of mechanically disrupting the seaweed and/or heating or cooking the seaweed.

In embodiments wherein the method includes the step of mechanically disrupting a seaweed, preferably the mechanical disruption is or includes blending. Preferably, the mechanical disruption further includes compression, preferably after blending.

In embodiments wherein the method includes the step of heating or cooking a seaweed, preferably the seaweed is heated or cooked in a liquid, preferably wherein the liquid is water. Preferably, the heating or cooking is boiling or simmering in water.

In embodiments, the heating or cooking according to this aspect is performed at a temperature of between about 80° C. to about 130° C.

In embodiments, the heating or cooking of a seaweed according to this aspect is performed at approximately atmospheric pressure, i.e. ~1 atm.

In embodiments wherein the heating or cooking of a seaweed is performed at approximately atmospheric pressure, the heating or cooking is preferably performed at a temperature of between about 80° C. to about 100° C., more preferably about 90° C.

In embodiments, the heating or cooking of a seaweed according to this aspect is performed at elevated pressure, i.e. greater than 1 atm. Preferably, the elevated pressure is between about 1.3 atm and about 3 atm.

In embodiments wherein the heating or cooking of a seaweed according to this aspect is performed at elevated pressure, preferably the heating or cooking is performed at a temperature of between about 100° C. to about 130° C., more preferably about 120° C.

Preferably, said heating or cooking at elevated pressure is performed for a duration of between about 1 and about 3 hours, more preferably about 2 hours.

Preferably, the seaweed is at least partially dried prior to heating or cooking.

In some preferred embodiments, the seaweed that is mechanically disrupted and/or heated in a liquid to obtain an extract according to the method of this aspect is a brown seaweed.

In embodiments wherein the seaweed is a brown seaweed, preferably the seaweed is of the order Fucales. More preferably, the seaweed is of the genus *Sargassum*. In a particularly preferred embodiment, the seaweed is of the species *Sargassum wightii*.

In some preferred embodiments, the seaweed that is mechanically disrupted and/or heated in a liquid to obtain an extract according to the method of this aspect is a red seaweed.

In embodiments wherein the seaweed is a red seaweed, preferably the seaweed is of the order Gigartinales. More preferably, the seaweed is of the genus *Hypnea*. In a particularly preferred embodiment, the seaweed is of the species *Hypnea musciformis*.

A third aspect of the invention provides a composition produced according to the method of the second aspect. In preferred embodiments of the third aspect, the composition is a composition of the first aspect.

In a fourth aspect, there is provided a method of stimulating the growth of a plant, the method including the step of applying the composition of the first or third aspects to the plant, to thereby stimulate the growth of the plant.

In some preferred embodiments of the fourth aspect, the composition is diluted less than about 1 in 6 prior to application to the plant. In some preferred embodiments of the fourth aspect, the composition is undiluted, or substantially undiluted, when applied to the plant.

In a fifth aspect there is provided a plant or plant part wherein the growth of the plant or plant part is or has been stimulated by the application of the composition of the first or third aspects.

It will be appreciated that the indefinite articles "a" and "an" are not to be read as singular indefinite articles or as otherwise excluding more than one or more than a single subject to which the indefinite article refers. For example, "a" hormone includes one hormone, one or more hormones or a plurality of hormones.

As used herein, unless the context requires otherwise, the words "comprise", "comprises" and "comprising" will be understood to mean the inclusion of a stated integer or group of integers but not the exclusion of any other integer or group of integers.

BRIEF DESCRIPTION OF THE FIGURES

FIG. 29 sets forth LCMS retention time for various plant hormone standards.

DETAILED DESCRIPTION

Figure 1:
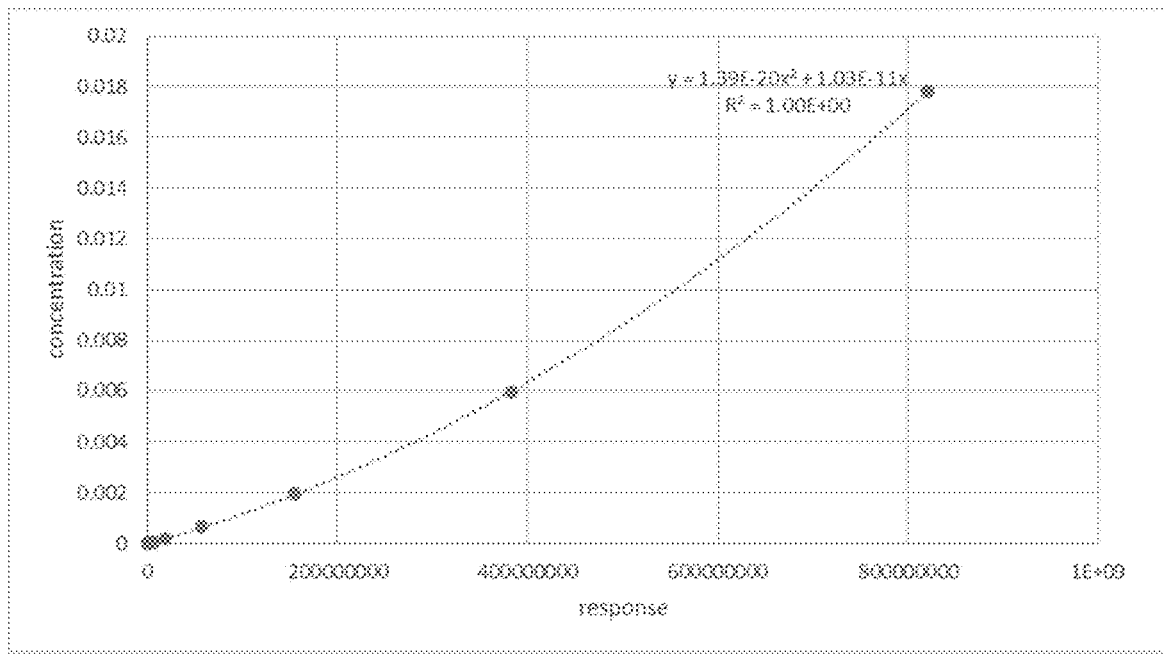
FIG. 1 sets forth an LCMS calibration curve for indole acetic acid.

The present invention is at least partly predicated on the identification of seaweed extracts that may have particularly desirable properties for stimulation of plant growth. The invention is also at least partly predicated on determination of methods that are effective for producing such seaweed extracts.

Compositions

In one aspect, there is provided a composition derived or derivable from seaweed, the composition comprising:
(a) one or more plant hormones, and/or
(b) one or more acidic polysaccharides.

Typically, the composition of this aspect comprises one or more plant hormones and one or more acidic polysaccharides.

Typically, the composition comprises a plurality of plant hormones.

Typically, the composition comprises a plurality of acidic polysaccharides.

Typically, the composition is an aqueous composition. As used herein, an "aqueous composition" will be understood to be a liquid composition wherein the primary solvent is water. However, while preferred, it will be appreciated that the composition need not necessarily be an aqueous composition. In certain alternative embodiments the composition may be, for example, in dry or substantially dry form, or in the form of a non-aqueous solution.

As will be understood by the skilled person, a "plant hormone" refers generally to a molecule that regulates plant growth, typically by cellular signalling. Plant hormones may alternatively be referred to as 'phytohormones', or 'plant growth substances'. For an overview of plant hormones, the skilled person is directed to Davies, P. J. (2010) The Plant Hormones: Their Nature, Occurrence, and Functions, In *Plant hormones* (pp. 1-15), Springer Netherlands. It will be appreciated that the inclusion of plant hormones in compositions of this aspect can be particularly desirable for stimulating plant growth, as herein described.

The one or more plant hormones of the composition of this aspect are typically selected from the group consisting of an auxin; a cytokinin; a phenolic plant hormone; an isoprenoid plant hormone; an aromatic plant hormone; and a lipid plant hormone.

In embodiments wherein the composition comprises one or more auxins, typically the auxin is or includes an auxin selected from the group consisting of indole-3-acetic acid (IAA); indole-3-acetic acid ethyl ester; indole-3-acetyl-glycine (IAGly); indole-3-acetyl-L-alanine (IAAla); indole-3-carboxylic acid (I3CA); indole-3-carboxylic acid methyl; indole-3-butyric acid (IBA); indole-3-glyoxylic acid methyl ester; DL-indole-3-lactic acid (ILA); indole-3-carboxaldehyde (IAld); and tryptophol (IEt).

In embodiments wherein the composition comprises one or more isoprenoid plant hormones, typically the isoprenoid plant hormone is or includes an abscisic acid and/or an isoprenoid cytokinin. Typically, the one or more abscisic acids is or includes (+)-cis, trans-abscisic acid (ABA). Typically, the one or more isoprenoid cytokinins is or includes N6-isopentenyladenine (iP) and/or cis-zeatin (cZ).

In embodiments wherein the composition comprises one or more aromatic plant hormones, typically the aromatic plant hormone is or includes an aromatic cytokinin. Typically, the aromatic cytokinin is or includes an aromatic cytokinin selected from the group consisting of N6-benzyladenine (BA); ortho-topolin (oT); para-topolin (pT).

In embodiments wherein the composition comprises one or more lipid plant hormones, typically the lipid plant hormone is or includes a jasmonate. Typically, the jasmonate is or includes (−)-jasmonic acid (JA) and/or (−)-jasmonic acid methyl ester.

In embodiments wherein the composition comprises one or more gibberellins, typically the gibberellin is or includes a gibberellin selected from the group consisting of gibberellin A3 (GA3); gibberellin A6 (GA6); and gibberellin A7 (GA7).

In embodiments wherein the composition comprises one or more salicylates, typically the salicylate is or includes salicylic acid.

As used herein, an "acidic polysaccharide" of compositions of this aspect will suitably be a polysaccharide that contains carboxyl groups, phosphate groups and/or sulfuric ester groups.

As will be known to the skilled person, seaweeds contain various acidic polysaccharides. Red seaweeds typically contain agar and carrageenan. Brown seaweeds typically contain alginates and fucoidans.

In embodiments wherein the composition comprises one or more acidic polysaccharides, typically the acidic polysaccharide is or includes an alginate; a fucoidan; an agar; and/or a carrageenan.

In a typical embodiment, the composition comprises an alginate and a fucoidan.

In a typical embodiment, the composition comprises an agar and a carrageenan.

As will be known to the skilled person, alginates typically exist in the form of a copolymer of β-D-mannuronic acid (M) and α-L-guluronic acid (G) residues, covalently linked together in different sequences or blocks. The monomers can appear in homopolymeric blocks of consecutive G-residues (G-blocks), consecutive M-residues (M-blocks) or alternating M and G-residues (MG-blocks).

Alginates have a range of industrial applications, including (by way of non-limiting example) additives in dehydrated products such as diet supplements; in the manufacture of paper and textiles; as a component of waterproofing and fireproofing fabrics; as a thickening agent for foods and cosmetics; and as a gelling agent. Alginate is also used as an ingredient in various pharmaceutical preparations, such as indigestion treatments in which it combines with bicarbonate to inhibit reflux; and as an impression-making material in dentistry and other prosthetics. Additionally, alginate can be useful as a soil conditioner and may have plant growth stimulating properties.

The skilled person will appreciate that fucoidans are fucose-containing sulfated polysaccharides, typically with a backbone of (1→3)-linked α-1-fucopyranosyl or of alternating (1→3)- and (1→4)-linked α-1-fucopyranosyl residues, but which also include sulfated galactofucans with backbones built of (1→6)-β-d-galacto- and/or (1→2)-β-d-mannopyranosyl units with fucose or fuco-oligosaccharide branching, and/or glucuronic acid, xylose or glucose substitutions. Notably, fucoidans offer several potentially beneficial bioactive functions for therapeutic treatment of humans or animals (see e.g. Fitton et al (2015) Therapies from Fucoidan: An Update, *Marine drugs* 13:5920-5946).

It will be appreciated by the skilled person that agars typically exist in the form of a mixture of agarose and agaropectin, with agarose making up about 70% of the mixture. Agarose is a linear polymer, formed from repeating units of agarobiose, a disaccharide of D-galactose and 3,6-anhydro-L-galactopyranose. Agaropectin is a heterogeneous mixture of smaller molecules formed from alternating units of D-galactose and L-galactose, modified with acidic side-groups such as sulfate and pyruvate.

Agar is commonly used as a gelling agent. It has particular applications as a food ingredient (common in Asian desserts), and as a solid substrate for microbiological culture. Agar can also used as a laxative, an appetite suppressant, a gelatine substitute, as a clarifying agent in brewing, and for sizing paper and fabrics.

The skilled person will appreciate that carrageenans are a family of linear sulfated polysaccharides. Carrageenans are high-molecular-weight polysaccharides made up of repeating galactose units and 3,6 anhydrogalactose (3,6-AG), both sulfated and nonsulfated, joined by alternating α-1,3 and β-1,4 glycosidic linkages. There are three main classes of carrageenan, which differ in degree of sulfation. Kappa-carrageenan has one sulfate group per disaccharide, iota-carrageenan has two, and lambda-carrageenan has three.

Carrageenans are widely used in the food industry, for their gelling, thickening, and stabilizing properties. A primary application is in dairy and meat products, due to the strong binding of carrageenans to food proteins. Other exemplary application of carrageenans include: in toothpaste as a stabiliser; in fire fighting foam as a thickener and foam adhesive; air-freshener gels; in shoe polish to increase viscosity; in pharmaceuticals as an excipient; in personal lubricants; and in biotechnology application e.g. for cell or enzyme immobilisation.

In embodiments of this aspect wherein the composition comprises an alginate, the alginate will suitably comprise poly M block, poly G block and/or copolymeric MG block regions.

Typically, the alginate comprises between about 30% and about 60% poly M block, including about: 35%, 40%, 45%, 50%, and 55% poly M block. In one embodiment, the alginate comprises about 45% poly M block.

Typically, the alginate comprises between about 10% and about 30% poly G block, including about: 15%, 20%, and 25% poly G block. In one embodiment, the alginate comprises about 19% poly G block.

Typically, the alginate comprises between about 25% and about 55% copoly MG block, including about: 30%, 35%, 40%, 45%, and 50% copoly MG block. In one embodiment, the alginate comprises about 36% copoly MG block.

In embodiments of this aspect wherein the composition comprises a fucoidan, the fucoidan will suitably comprise fucose, and one or more of glucose, galactose and/or mannose. Typically, the fucoidan comprises fucose, glucose, galactose and mannose.

Also included within the scope of this aspect are compositions comprising, additionally or alternatively, analogues and/or derivatives of the one or more plant hormones and/or one or more acidic polysaccharides as described above.

As used herein, an "analogue" refers to a chemical compound that is structurally similar to an original or 'parent' compound, but differs slightly in composition (e.g., an atom or functional group is different, added, or removed). The analogue may or may not have different chemical or physical properties than the parent compound and may or may not have altered biological and/or chemical activity. By way of non-limiting example, the analogue may be more hydrophilic or it may have altered reactivity as compared to the parent compound. The analogue may mimic the chemical and/or biologically activity of the parent compound (i.e., it may have similar or identical activity), or, in some cases, may have increased or decreased activity.

It will be further appreciated that an analogue may be a naturally or non-naturally occurring (e.g., recombinant) variant of an original compound. Analogues include isomers (enantiomers, diasteromers, and the like) and other types of chiral variants of a compound, as well as structural isomers. The analogue may be a branched or cyclic variant of a linear compound. For example, a linear compound may have an analogue that is branched or otherwise substituted to impart certain desirable properties (e.g., without limitation, improved hydrophilicity or bioavailability).

As used herein, a "derivative" refers to a chemically or biologically modified version of a chemical compound that is structurally similar to an original or parent compound and (actually or theoretically) derivable from that parent compound. A "derivative" differs from an "analogue" in that a parent compound may be the starting material to generate a derivative, whereas the parent compound need not necessarily be used as the starting material to generate an analogue.

A derivative may or may not have different chemical or physical properties than the parent compound. For example, the derivative may be more hydrophilic or it may have altered reactivity as compared to the parent compound. Derivatization (i.e., modification) may involve substitution of one or more moieties within the molecule (e.g., a change in functional group). By way of non-limiting example, a hydrogen may be substituted with a halogen, such as fluorine or chlorine, or a hydroxyl group (—OH) may be replaced with a carboxylic acid moiety (—COOH).

As used herein, the term derivative encompasses all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

Typically, in embodiments wherein the composition of this aspect comprises analogues or derivatives of a plant hormone or acidic polysaccharide, the analogue or derivative should be a biologically active analogue or derivative. As used herein a "biologically active" analogue or derivative will be understood to refer to an analogue or derivative retaining at least a portion of one or more biological activities of the parent compound. Without limitation thereto, the biological activity may stimulation of plant growth. Typically, the analogue or derivative should possess at least 10%, 20%, 30%, 40%, 50%, 60%, 70%, 80%, or 90% of one or more biological activities of the plant hormone or acidic polysaccharide, such as stimulation of plant growth.

The composition according to this aspect may contain any suitable concentration or amount of the one or more plant hormones and/or one or more acidic polysaccharides (or analogue(s) or derivative(s) thereof). Typically, although without limitation, the concentration of one or more of the one or more plant hormones and/or one or more acidic polysaccharides in the composition will be suitable for stimulating the growth of a plant.

It will be readily understood by the skilled person that compositions as described herein, e.g. plant fertiliser compositions, are often provided in concentrated form, that can be formulated to achieve a desired concentration for application.

In some typical embodiments, compositions as described herein can be considered concentrates, and are typically diluted prior to application, e.g. for stimulation of growth of a plant. In these embodiments, typically, the composition is diluted about 1 in 50 or less, including about 1 in 40 (i.e. 1:39), 1 in 30, 1 in 20, 1 in 15, 1 in 10, 1 in 5, 1 in 4, 1 in 3, and 1 in 2, prior to application. More typically, the composition is diluted less than about 1 in 6, including about 1 in 5, 1 in 4, 1 in 3, 1 in 2, or less.

In some typical embodiments, compositions as described herein are applied undiluted, or substantially undiluted.

For the sake of clarity, it will be understood that, unless the context requires otherwise, the concentrations referred to herein are concentrations in the composition in the absence of any dilution prior to application. It will be further understood that, unless the context requires otherwise, concentrations referred to herein are in weight per weight terms. The skilled person can readily convert weight per weight concentrations to other suitable concentration measures (e.g. weight per volume, volume per volume, etc.) as required.

Typically, in embodiments of the composition of this aspect comprising one or more plant hormones (or analogues or derivatives thereof), the concentration of each of the one or more plant hormones in the composition is between about 0.01 parts per billion (ppb), and about 1000 parts per billion (or 1 ppm), including about: 0.02, 0.03, 0.04, 0.05, 0.06, 0.07, 0.08, 0.09, 0.1, 1, 2, 3, 4, 5, 6, 7, 8, 9, 10, 20, 30, 40, 50, 60, 70, 80, 90, 100, 200, 300, 400, 500, 600, 700, 800, and 900 ppb.

In embodiments wherein the composition comprises one or more auxins, typically, the total concentration of said auxin(s) is between about 0.1 ppb and about 1000 ppb (or 1 ppm), including about: 1, 10, 20, 30, 40, 50, 60, 70, 80, 90, 100, 200, 300, 400, 500, 600, 700, 800, and 900 ppb.

In embodiments wherein the composition comprises one or more cytokinins, typically, the total concentration of said cytokinin(s) is between about 0.1 ppb and about 50 ppb, including about: 1, 2, 3, 4, 5, 6, 7, 8, 9, 10, 20, 30, and 40 ppb.

In embodiments wherein the composition comprises one or more gibberelins, typically, the total concentration of said gibberellin(s) is between about 0.005 ppb and about 5 ppb, including about: 0.01, 0.05, 0.1, 0.5, 1, 2, 3, and 4 ppb.

In embodiments wherein the composition comprises one or more salicylates, typically, the total concentration of said salicylate(s) is between about 0.01 and about 20 ppb, including about: 0.05, 0.1, 1, 2, 3, 4, 5, 10, and 15 ppb.

In embodiments wherein the composition comprises one or more abscisic acids, typically, the total concentration of said abscisic acid(s) is between about 0.05 and about 20 ppb, including about 0.1, 05, 1, 2, 3, 4, 5, 10, and 15 ppb.

In embodiment wherein the composition comprises one or more jasmonates, typically, the total concentration of said jasmonate(s) is between about 0.1 ppb and about 50 ppb, including about: 0.5 ppb, 1 ppb, 10 ppb, 20 ppb, 30 ppb, and 40 ppb.

In certain embodiments, the composition comprises a concentration of one or more of the plant hormones listed in Table 1, of between about 1% and 150%, including about: 2, 3, 4, 5, 6, 7, 8, 9, 10, 20, 30, 40, 50, 60, 70, 80, 90, 100, 110, 120, 130, and 140%, of the concentration in seaweed that is implied by the analysis of 'Composition 1'; 'Composition 2'; or the 'Control' composition. In some of said embodiments, the composition comprises a concentration of one or more of the plant hormones listed in Table 2 of between about 5% and about 100%; between about 7.5% and about 50%; between about 10% and about 25%; or about 10% of the concentration in seaweed implied by the analysis of one or more of said compositions.

In certain embodiments, the composition comprises a concentration of one or more of the plant hormones listed in Table 2, of between about 10% and 1000%, including about: 20, 30, 40, 50, 60, 70, 80, 90, 100, 150, 200, 250, 300, 350, 400, 450, 500, 550, 600, 650, 700, 750, 800, 850, 900, and 950%, of the concentration given for 'Composition 1' or 'Composition 2'. In some of said embodiments, the composition comprises a concentration of one or more of the plant hormones listed in Table 2 of between about 30% and about 300%; between about 50% and about 150%; or about 100% of the concentration given for 'Composition 1' or Composition 2'.

In embodiments of the composition of this aspect comprising one or more acidic polysaccharides (or analogues or derivatives thereof), the concentration of each of said one or more acidic polysaccharides in the composition may be between about 50 ppm to about 10%. Typically, the total concentration of said one or more acidic polysaccharides in the composition is between about 0.1% to about 20%.

In embodiments wherein the composition comprises one or more alginates, typically the concentration of said alginates is between about 0.1% to about 10%, including about: 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, and 9.5%. In some said embodiments said concentration is between about 0.5% to about 2.5%; or about 1%.

In embodiments wherein the composition comprises one or more fucoidans, typically the concentration of said alginates is between about 50 ppm to about 10000 ppm, including about: 100, 200, 300, 400, 500, 600, 700, 800, 900, 1000, 2000, 3000, 4000, 5000, 6000, 7000, 8000, and 9000 ppm. In some said embodiments said concentration is between about 100 ppm to about 3000 ppm; between about 150 ppm to about 250 ppm; or between about 1000 to about 3000 ppm.

It will be further understood that in embodiments of this aspect wherein the composition is derived from a seaweed, the composition will suitably be in the form of, or comprise, a seaweed extract. The seaweed extract may be obtained from the seaweed using any suitable extraction technique. Suitable extraction techniques may include simple extraction techniques such as mechanical processing and/or boiling, or more complex extraction techniques such as those involving a series of processing steps and/or solvents. It will be appreciated that the seaweed extract may obtained in any suitable form (e.g., solid or liquid; dry or in solution, such as aqueous solution).

For a non-limiting overview of plant extraction techniques, which techniques may be appropriate for obtaining seaweed extracts suitable for compositions of this aspect, the skilled person is directed to: *Phytochemical Methods A Guide to Modern Techniques of Plant Analysis*, J. B. Harborne, Chapman & Hall (1998). In particular regard to extraction of plant hormones, the skilled person is directed to: Koshiba, T (2010) Plant Hormones, Methods and Protocols, *Annals of botany*, 105(4), viii. In particular regard to extraction of seaweed polysaccharides, the skilled person is directed to: Chapter 14: Conventional and Alternative Technologies for the Extraction of Algal Polysaccharides, *In Functional Ingredients from Algae for Foods and Nutraceuticals* (Dopminguez, Ed.), Woodhead Publishing (2013).

In certain embodiments, the composition according to this aspect consists of, or consists essentially of, a seaweed extract. In certain embodiments, the composition consists of, or consists essentially of, a seaweed extract and water.

In alternative embodiments, the composition may include other suitable additives or components. Such other additives or components may include, generally, fillers, diluents, and excipients, all of which are known in the art. Such other additives or components may additionally or alternatively include additional active agents, inclusive of fertilisers, such as (by way of non-limiting example) ureas; nitrates (such as ammonium and calcium nitrate); sulfates (such as ammonium sulphate); phosphates (such as diammonium, monoammonium, and 'triple super' phosphate); nitrates (such as potassium nitrate); and chlorides (such as potassium chloride).

Active agents that may be included in the composition of this aspect may additionally or alternatively be in the form of plant hormones or other potentially growth-stimulating agents, inclusive of auxins, gibberellins, cytokinins, ethylenes, abscisic acids, brassinosteroids, jasmonates, salicylates, strigolactones, karrikins, oligosaccharins, oligogalacturonides, xyloglucans, arabinogalactan proteins, unconjugated N-glycans, lignins, plant peptide hormones, polyamines, nitric oxide, triacontanol, and/or any of the plant growth hormones and/or acidic polysaccharides hereinabove described.

It will be further understood that multiple distinct compositions according to this aspect may be obtained by differential extraction of various agents from seaweed.

Typically, compositions of this aspect comprise a plurality of plant hormones and a plurality of acidic polysaccharides. However, as will be evident to the skilled person in view of common knowledge and the Examples provided herein, distinct compositions comprising particular components can be produced, such as a composition comprising plant hormones, and a distinct composition comprising acidic polysaccharides, or any other agent-composition combinations that may be desirable. It will be appreciated that each distinct composition may consist of or consist essentially of a seaweed extract, or a seaweed extract and water. Alternatively, each distinct composition may include additional agents as hereinabove described.

In the above-described embodiments of this aspect wherein the composition comprises a seaweed extract, the seaweed extract may be from any suitable seaweed. As will be known to the skilled person, seaweed includes a variety of species of macroscopic, multicellular, marine algae. Generally, seaweed may be red algae (red seaweed), brown algae (brown seaweed), or green algae (green seaweed).

In some typical embodiments, the seaweed extract is of a brown seaweed of the class Phaeophyceae.

In embodiments, the brown seaweed may be of an order selected from the group consisting of Desmarestiales; Laminariales; and Fucales. Typically, the brown seaweed is of the order Fucales.

In embodiments, the brown seaweed may be of a genus selected from the group consisting of *Eisenia; Alaria; Durvillaea; Ecklonia; Saccharina; Laminaria; Postelsia; Nereocystis; Undaria; Fucus; Pelvetia; Sargassum; Himanthalia*; and *Cladosiphon*. Typically, the brown seaweed is of the genus *Sargassum*.

In embodiments, the brown seaweed may be of a species selected from the group consisting of *Sargassum fusiforme; Sargassum echinocarpum; Sargassum cinetum; Sargassum vulgare; Sargassum swartzii; Sargassum myriocysum*; and *Sargassum wightii*. Typically, the brown seaweed is of the species *Sargassum wightii*.

In some typical embodiments, the seaweed extract is of a red seaweed of the class Florideophyceae.

In embodiments, the red seaweed may be of an order selected from the group consisting of Bonnemaisoniales; Ceramiales; Gelidiales; Gigartinales; Gracilariales; Halymeniales; Nemastomatales; Peyssonneliales; Plocamiales; and Rhodymeniales. Typically, the red seaweed is of the order Gigartinales.

In embodiments, the red seaweed may be of a genus selected from the group consisting of *Acanthococcus; Austroclonium; Bifida; Calliblepharis; Ciliaria; Craspedocarpus; Cystoclonium; Dictyopsis; Erythronaema; Fimbrifolium; Gloiophyllis; Hypnea; Hypneocolax; Leptophyllium; Peltasta; Rhodophyllis; Stictophyllum*; and *Stictosporum*. Typically, the red seaweed is of the genus *Hypnea*.

In embodiments, the red seaweed may be of a species selected from the group consisting of *Hypnea musciformis; Hypnea saidana*; and *Hypnea valentiae*. Typically, the red seaweed is of the species *Hypnea musciformis*.

It will be appreciated, however, that compositions according to this aspect need not necessarily comprise a seaweed extract. In alternative embodiments, the composition may include plant hormones and/or acidic polysaccharides obtained from other sources, such as from extraction from other plants or algae, or by synthetic production.

The composition derived or derivable from seaweed according to this aspect is typically for stimulation of plant growth. As used herein, "stimulation or plant growth" will be understood to refer to increasing, enhancing, or otherwise facilitating one or more characteristics of plant growth and/or development. Without limitation, this may include enhancing vegetative growth of a plant, such as growth of leaves, stems, and/or branches; enhancing root growth; encouraging transition into a reproductive phase; and enhancing growth of reproductive tissues or organs such as flowers, fruit, and seeds.

In alternative embodiments, the composition may be for another suitable application. In this respect, the skilled person will appreciate that compositions comprising agents derived or derivable from seaweed may have other applications, for example in the fields of food preparation, biological research, cosmetics, and therapeutics, including those hereinabove described in relation to acidic polysaccharides.

In some embodiments, the composition may be for a therapeutic application, such as treatment of a disease or condition in a human or animal subject. In some embodiments, the composition may be used as an ingredient in food preparation.

Methods of Producing Compositions

In another aspect, the invention provides a method of producing a composition, the method including the step of obtaining an extract from a seaweed, to thereby produce the composition.

The technique that is used to obtain the seaweed extract according to the method of this aspect may be any suitable technique such as hereinabove described.

In embodiments, the method of this aspect includes the step of washing or rinsing the seaweed in a solution prior to obtaining an extract from the seaweed.

In a typical embodiment, the washing or rinsing is or includes washing or rinsing in a solution comprising salt. Typically, the solution comprising salt is a salt water solution.

In a typical embodiment, the washing or rinsing includes washing or rinsing in pure, or substantially pure water. Typically, the pure of substantially pure water is distilled water.

Typically, the step of washing or rinsing the seaweed is performed for about 3 hours to about 24 hours, including about 4, 5, 6, 7, 8, 9, 10, 11, 12, 13, 14, 15, 16, 17, 18, 19, 20, 21, 22, and 23 hours.

In embodiments, after washing or rinsing, the seaweed is separated from most or substantially all of the solution with which the seaweed was washed or rinsed.

Typically, the method of this aspect includes the step of combining the seaweed or an extract thereof with a liquid before and/or after obtaining the extract from the seaweed to produce the composition. Preferably, the liquid is water. By way of elaboration, it will be readily appreciated that, without limitation, an extract can be first obtained from a seaweed by suitable processing, then subsequently combined with water to thereby produce the composition. Alternatively, seaweed can be combined with water and processed, to release the seaweed extract into the water, to thereby produce the composition.

Typically, the ratio of seaweed or an extract thereof to liquid that is combined according to the method of this aspect is between about 50 and about 1000 grams seaweed per litre (g/L), including about: 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 g/L, more typically between about 50 and about 250 grams of seaweed per litre of liquid. In one embodiment said ratio is about 100 g/L. For clarity, in embodiments wherein a seaweed extract is combined with liquid according to the method of this aspect, typically the ratio will be an amount of extract obtainable from between about 50 and about 1000 grams, more typically between about 50 and about 250 grams, of seaweed per litre of liquid.

Typically, the extract is obtained from the seaweed by mechanically disrupting the seaweed and/or heating the seaweed.

In embodiments wherein the method includes the step of mechanically disrupting a seaweed to obtain the seaweed extract, typically the mechanical disruption is or includes blending. As will be readily understood by the skilled person, in this context, "blending" refers to mechanical processing typically using one or more blades such as rotatable blades. Typically after blending, the seaweed will be in the form of a sludge or slurry. The blended seaweed may be relatively or substantially homogenous.

In embodiments wherein the method includes the step of mechanically disrupting a seaweed to obtain the seaweed extract, typically the mechanical disruption includes compression. As will be readily understood by the skilled person, in this context, "compression" refers to the application of a force to the seaweed to squeeze or press the seaweed together.

In embodiments of this aspect wherein the method includes the step of heating a seaweed, typically the seaweed is heated in a liquid. Typically the liquid is water. Typically, the water is pure water or substantially pure water. In one typical embodiment, the water is distilled water. Heating in substantially pure water, typically distilled water, can be particularly desirable for red seaweed as hereinabove described, although without limitation thereto.

In embodiments, the step of heating is or includes boiling the seaweed in the liquid. "Boiling" will be understood to be the heating of a liquid to or near to its 'boiling point', wherein relatively rapid vaporisation of the liquid occurs.

Typically, the heating according to this aspect is performed at a temperature of between about 50° C. to about 130° C., including about: 55, 60, 65, 70, 75, 80, 85, 90, 95, 100, 105, 110, 115, 120, and 125° C.

In embodiments, the heating of a seaweed according to this aspect is performed at approximately atmospheric pressure, i.e. ~1 atm. In embodiments wherein the heating or cooking of a seaweed is performed at approximately atmospheric pressure, the heating or cooking is typically performed at a temperature of between about 70° C. to about 100° C., more typically about 80° or about 90° C.

In embodiments, the heating or cooking of a seaweed according to this aspect is performed at elevated pressure, i.e. greater than 1 atm. It will be understood that, as used herein, heating of a seaweed, typically in liquid, at elevated pressure, may be referred to as 'pressure cooking'.

Typically, the elevated pressure is about 1.1 atm to about 5 atm including about: 1.1, 1.2, 1.3, 1.4, 1.5, 1.6, 1.7, 1.8, 1.9, 2, 2.5, 3, 3.5, 4, and 4.5 atm. It will be appreciated that a pressure of about 1.1 atm to about 5 atm is equivalent to a pressure of 0.1 atm and about 4 atm above atmospheric pressure.

In embodiments wherein the heating or cooking of a seaweed according to this aspect is performed at elevated pressure, typically the heating or cooking is performed at a temperature of between about 100° C. to about 130° C., more typically about 120° C. or about 121° C.

Typically, the duration of heating of the seaweed according to the method of this aspect is between about 10 minutes and about 10 hours, including about: 20 minutes, 30 minutes, 40 minutes, 50 minutes, 60 minutes, 1 hour, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, and 9.5 hours.

In some embodiments, heating of the seaweed is first performed at around atmospheric pressure, and pressure cooking is then subsequently performed. In these embodiments, typically, the duration of heating the seaweed at around atmospheric pressure is about 3 to about 9 hours, including about 4, 5, 6, 7, and 8 hours. In these embodiments, typically the duration of heating the seaweed at elevated pressure is about 0.5 to about 5 hours, including about 1, 1.5, 2, 2.5, 3, 3.5, 4, and 4.5 hours.

Typically, the ratio of seaweed to liquid that is heated according to embodiments of the method of this aspect is between about 50 and about 200 grams per litre (g/L), including about: 60, 70, 80, 90, 100, 110, 120, 130, 140, 150, 160, 170, 180, and 190 g/L. In one embodiment said ratio is about 100 g/L.

In embodiments, the seaweed is at least partially dried prior to heating in a liquid. In embodiments, the seaweed may be between about 20% and about 80% dried, including about: 30, 40, 50, 60, and 70% dried, relative to the water content of freshly harvested seaweed. Any suitable drying technique may be used for said drying, such as sun drying or oven drying, as will be well known to the skilled person. Typically, the drying is sun drying.

Typically, after processing of the seaweed such as by mechanical disruption and/or boiling, a further step of filtering or otherwise separating at least a substantial amount of a solid component from a liquid component of the processed material is performed according to the method of this aspect, to obtain the seaweed extract. Any suitable filter or other apparatus may be used for said filtering step. In an embodiment, the liquid component is filtered using a sieve, e.g. comprising wire or plastic mesh to form openings through which material may pass. Typically, the opening or sieve size of the sieve is between about 0.01 to about 1 mm, including about 0.02, 0.03, 0.04, 0.05, 0.06, 0.07, 0.08, 0.09, 0.1, 0.2, 0.3, 0.4, 0.5, 0.6, 0.7, 0.8, and 0.9 mm. In one embodiment, the sieve size is about 0.1 mm.

Typically the liquid component that is separated from the solid component is used as, or to obtain, the seaweed extract to produce the composition.

In alternative embodiments, the solid component that is separated from the liquid component is used as, or to obtain, the seaweed extract.

Any suitable seaweed may be used to obtain the extract according to the method of this aspect, as hereinabove described.

In some typical embodiments, the seaweed is a brown seaweed of the class Phaeophyceae.

In embodiments, the brown seaweed may be of an order selected from the group consisting of Desmarestiales; Laminariales; and Fucales. Typically, the brown seaweed is of the order Fucales.

In embodiments, the brown seaweed may be of a genus selected from the group consisting of *Eisenia; Alaria; Durvillaea; Ecklonia; Saccharina; Laminaria; Postelsia;*

*Nereocystis; Undaria; Fucus; Pelvetia; Sargassum; Himanthalia;* and *Cladosiphon*. Typically, the seaweed is of the genus *Sargassum*.

In embodiments, the brown seaweed may be of a species selected from the group consisting of *Sargassum fusiforme; Sargassum echinocarpum; Sargassum cinetum; Sargassum vulgare; Sargassum swartzii; Sargassum myriocysum;* and *Sargassum wightii*. Typically, the brown seaweed is of the genus *Sargassum wightii*.

In some typical embodiments, the seaweed extract is of a red seaweed of the class Florideophyceae.

In embodiments, the red seaweed may be of an order selected from the group consisting of Bonnemaisoniales; Ceramiales; Gelidiales; Gigartinales; Gracilariales; Halymeniales; Nemastomatales; Peyssonneliales; Plocamiales; and Rhodymeniales. Typically, the red seaweed is of the order Gigartinales.

In embodiments, the red seaweed may be of a genus selected from the group consisting of *Acanthococcus; Austroclonium; Bifida; Calliblepharis; Craspedocarpus; Cystoclonium; Dictyopsis; Erythronaema; Fimbrifolium; Gloiophyllis; Hypnea; Hypneocolax; Leptophyllium; Peltasta; Rhodophyllis; Stictophyllum;* and *Stictosporum*. Typically, the red seaweed is of the genus *Hypnea*.

In embodiments, the red seaweed may be of a species selected from the group consisting of *Hypnea musciformis; Hypnea saidana;* and *Hypnea valentiae*. Typically, the red seaweed is of the species *Hypnea musciformis*.

Typically, the extract obtained from a seaweed according to the method of this aspect is used directly as the composition.

In alternative embodiments, the method of this aspect may include the further step of combining one or more additional additives or components with the seaweed extract to produce the composition.

As hereinabove described, such other additives or components may include, generally, fillers, diluents, and excipients, all of which are known in the art. Such other additives or components may additionally or alternatively include additional active agents, inclusive of fertilisers, such as (by way of non-limiting example) ureas;

nitrates (such as ammonium and calcium nitrate); sulfates (such as ammonium sulphate); phosphates (such as diammonium, monoammonium, and 'triple super' phosphate); nitrates (such as potassium nitrate); and chlorides (such as potassium chloride). Active agents that may be included may additionally or alternatively be in the form of or other potentially growth stimulating agents, inclusive of auxins, gibberellins, cytokinins, ethylenes, abscisic acids, brassinosteroids, jasmonates, salicylates, strigolactones, karrikins, oligosaccharins, oligogalacturonides, xyloglucans, arabinogalactan proteins, unconjugated N-glycans, lignins, plant peptide hormones, polyamines, nitric oxide, triacontanol, and/or any of the plant growth hormones and/or acidic polysaccharides hereinabove described.

A related aspect provides a composition produced according to the method of this aspect. Typically, the composition will be as described for the preceding aspect.

Method of Stimulating Plant Growth

Another aspect of the invention provides a method of stimulating the growth of a plant, including the step of applying a composition of the previous aspects to the plant, to thereby stimulate the growth of the plant.

In some typical embodiments, the composition is diluted prior to application to the plant. Typically, the dilution is dilution in water. In these embodiments, typically, the composition is diluted about 1 in 50 or less including about 1 in 40 (i.e. 1:39), 1 in 30, 1 in 20, 1 in 15, 1 in 10, 1 in 5, 1 in 4, 1 in 3, and 1 in 2, prior to application. More typically, the composition is diluted less than about 1 in 6, including about 1 in 5, 1 in 4, 1 in 3, 1 in 2, or less.

In some typical embodiments, the composition is applied to the plant undiluted, or substantially undiluted.

The composition may be applied to the plant according to the method of this aspect in any suitable manner.

In some embodiments, the composition is applied to the plant by adding the composition to a growth medium within which the plant is placed or located. It will be appreciated that such a growth medium may be a soil, or a planting or potting mix as are well known in the art. Other growth mediums include, without limitation, liquid growth mediums such as for hydroponic plant culture; and synthetic planting mixes or mediums such as are known in the art and may be, for example, used in the context glasshouse-based plant growth and/or tissue culture.

In some embodiments, the composition is applied to the foliage of the plant, in the form of a foliar fertiliser as are known in the art.

Stimulation of plant growth according to this aspect may be in any suitable form such as described herein. That is, according to the method of this aspect, one or more of growth and/or development of a plant or plant part will suitably be increased, enhanced, or otherwise facilitated by the application of the composition to the plant. Without limitation, the method of this aspect may enhance vegetative growth of a plant, such as growth of leaves, stems, and/or branches; enhance root growth; encourage transition of a plant into a reproductive phase; and/or enhance growth of reproductive tissues or organs such as flowers, fruit, and seeds.

In embodiments, the method of this aspect may increase, enhance, or facilitate a plant growth characteristic that can be quantified as a percentage relative to a corresponding plant that has been untreated, or treated with one or more other compositions. The skilled person can readily determine suitable parameters for said quantification. By way of non-limiting example, suitable parameters may include size, height, breadth or width, or weight of an entire plant or the above or below ground components thereof. Suitable parameters may also include size or weight of individual plant components, including vegetative components such as stems, leaves, roots, branches etc.; and/or reproductive components such as flowers, fruit, and/or seeds. In some embodiments, suitable parameters may relate to the timing of a developmental event, such as flowering or fruiting, e.g. as measured in days-post planting.

In embodiments, the percentage stimulation of a plant that is achieved according to the method of this aspect is within the range of about 0.1% to about 100%, including about: 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75% 80%, 85%, 90%, and 95%.

In a related aspect, there is provided a plant or part thereof, wherein the growth of the plant or plant part is or has been has been stimulated by the application of a composition as herein described.

It will be understood that the plant or plant part with stimulated growth according to the preceding aspects may be any suitable plant or plant part as herein described. In this context, the term "plant" will be understood to include:

"Embryophyta" or "land plants", with reference to Margulis, L (1971) Evolution, 25: 242-245 (incorporated herein by reference) and inclusive of liverworts, hornworts, mosses, and vascular plants;

"Viridiplantae" or "green plants", with reference to Copeland, H F (1956) Palo Alto: Pacific Books, p. 6 (incorporated herein by reference) and inclusive of land plants and green algae.

"Archaeplastida" with reference to Cavalier-Smith, T (1981) *BioSystems* 14: 461-481 (incorporated by reference) and inclusive of land plants, green plants, *Rhodophyta* (red algae) and *Glaucophyta* (glaucophyte algae); and "Vegetabilia" with reference to Linnaeus, C (1751) *Philosophia botanica*, 1st ed, p. 37 (incorporated by reference) and inclusive of land plants, green plants, Archaeplastida, and diverse algae and fungi, such as edible fungi including mushrooms.

Typically, the plant is a monocotyledonous plant or a dicotyledonous plant.

In certain embodiments, the plant is grass of the Poaceae family such as sugar cane; a *Gossypium* species such as cotton; a berry such as strawberry; a tree species inclusive of fruit trees such as apple and orange and nut trees such as almond; an ornamental plant such as an ornamental flowering plant, inclusive of rosaceous plants such as rose; a vine inclusive of fruit vines such as grapes; a cereal including sorghum, rice, wheat, barley, oats, and maize; a leguminous species including beans such as soybean and peanut; a solanaceous species including tomato and potato; a brassicaceous species including cabbage and oriental mustard; a cucurbitaceous plants including pumpkin and zucchini; a rosaceous plants including rose; an asteraceous plants including lettuce, chicory, and sunflower, or a relative of any of the preceding plants.

Also provided according to an aspect of the invention is a method of treating a disease or condition in a subject, the method including the step of administering an effective amount of the composition of the previous aspect to the subject, to thereby treat the disease or condition in the subject. The subject may be any suitable subject, such as an animal or human subject.

EXAMPLES

Example 1. Extraction Techniques

Techniques for obtaining seaweed extracts were developed for the invention, and compositions comprising these extracts were produced, as described in this example.

Technique 1

Fresh seaweed samples (predominantly *Sargassium wightii* with trace amounts of *Enhalus acoroides*) were blended using an industrial blender, as are well-known in the art. The particular setting of blending speed was adjusted to achieve effective blending, with a higher blending setting required where a greater amount of fresh seaweed was used. Blending was performed for a suitable period of time to produce a sludge or slurry. Similar as for blending speed, the duration of blending required varied depending on the amount of fresh seaweed used. After blending, the slurry was compressed, either by hand or using an industrial squeezing or juicing apparatus, as are well-known in the art. Filtering was then performed using an industrial sieve of pore size 0.1 mm, and the liquid component was collected as a seaweed extract.

After collection of the seaweed extract, the extract was diluted in water by combining 10 L of water with extract obtained from 1 kg of seaweed, to form a composition (Composition 1) suitable for stimulation of plant growth. Alternatively, higher concentrations of extract may be used, such as approximately 1 L of water with 0.25 L of extract (i.e. 1 L extract to 4 L water), to form compositions suitable for stimulation of plant growth. Additionally, remaining solid seaweed material was pulverised into a powder to form a further composition, which may be used as a potting mix or soil conditioner.

Technique 2

Fresh seaweed samples as for Technique 1 were first sun dried until the samples were approximately 60% dry, typically for a duration of about 6 to about 12 hours. After drying, the seaweed was combined with water at a ratio of 10 L water per 1 kg seaweed (fresh weight), and boiled for 1 hour at 90° C. It will be appreciated however that, alternatively, a higher concentration of seaweed may be used, such as up to about 500 g of seaweed (fresh weight) per 1 L of water, or even higher.

After boiling, solid seaweed material was removed from the water, with the remaining liquid component forming the extract. This boiled seaweed extract formed a composition (Composition 2) suitable for stimulation of plant growth. Additionally, remaining solid seaweed material was pulverised into a powder to form a further composition, which may be used as a potting mix.

Example 2. Determination of Plant Hormones in Seaweed Compositions

Quantification of growth hormones in Composition 1 and Composition 2, and in a Control composition for comparison, was performed as described in this example.

Summary of Procedures

Samples

Composition 1 and Composition 2, as described in Example 1, were used for analysis according to this Example. Additionally, a control ethanol/water extract (Control) was prepared by extraction of dried, powdered seaweed samples similar as described in Example 1, as described in detail below.

Analysis

Composition 1, Composition 2, Control, and relevant standards as described in detail below were separately chromatographed on a DEAE Sephadex column. Specifically, the column was eluted with ethanol:water containing acetic acid. Two fractions of 500 mL each were collected followed by 1 L fractions to give a total of 13 fractions. Each fraction was separately concentrated except in the case of the standards, where fractions 1 and 2 were combined and concentrated. The concentrate was then made up to an accurately known volume in methanol and analysed by LC-MS.

For LC-MS analysis, an external standard with a similar molecular structure (cordycepin) was added to each diluted concentrate and the solution injected onto the LC-MS to give a chromatogram of each sample with associated masses. This instrument detects the mass to 4 decimal places so enables accurate assessment of the molecular weight. The mass spectrometer uses electrospray to ionise the molecules and generates both a positive ion and negative ion spectrum. Some molecules do not produce ions in the negative ion spectrum.

Each of the standards was serially diluted then put through the LC-MS to determine the response (by integration of the peaks) and retention time. The responses were graphed against the concentration to construct a calibration curve (as set out in FIGS. 1-23. The specific positive and negative ion masses were calculated for each plant hormone, and these masses were searched for in the positive and negative ion traces for each fraction. Peaks corresponding to the retention time for the standard were integrated and the concentration in the fraction calculated from the calibration curve. The concentrations for each fraction were converted to amounts in the whole fraction then added to give the total amount in each extract.

The injections of the fractions and standards were periodically interspersed with an injection of a mixture of standards. The same mixture was used each time. It was expected that the external standard could be used to normalise each run. It is usually assumed that this is valid, however in this case it proved not to be so as each molecule varied differently to the others between runs. So, the values were not normalised, but instead the mixture of standards was used to calculate the variation in response.

Due to the time taken to run each DEAE column, only one column was run for each sample so variation from this is not included but this is assumed to be within the level of variation of the mass spectrum for the purposes of the results presented herein. The standard deviation derived from the variation in the mass spectrum is given as the experimental uncertainty for each value. This was not determined for IAA-Ala, IAA-Gly or IAAEt so the highest standard deviation for other auxins was used for these. This does not account for any uncertainties in running the DEAE Sephadex column as these were not repeated. These could be substantial; other reports on uncertainties put some up to 50% of the reported figure.

Each compound was identified by both its accurate mass and its retention time on the column as compared to the standard. Variations in retention time were within ±0.12 min. The response for each compound was determined by integration under the mass peak for the accurate mass of the molecular ion. In some cases the peaks were not single sharp peaks, due to spreading on the LC, but the pattern in the standard matched that in the sample. In some cases, a second mass fragment ion could be used for confirmation of the structure. These were used where present.

Given that the components are identified by their accurate mass, it was also possible to search the LC-MS trace for a compound for which a standard was not available, and rule it out if it was not there. This was carried out for a number of compounds.

Results and Discussion

Comparison of Composition 1, Composition 2, and Control

Composition 1 and Composition 2 were found to contain auxins, cytokinins, gibberellins, salicylic acid, abscisic acid and jasmonates (Table 1). However, the profile of the two Compositions was substantially different, at least in respect of some hormones.

Composition 1 was missing several of the auxins, perhaps due to lack of solubility in water, or failure of the water to access the storage site in the seaweed. Notably, the recovery of indole acetic acid ethyl ester from the column was over 100%. This was attributed to conversion of indole acetic acid to its ethyl ester on the column due to use of ethanol in the solvent. As the values in the table are adjusted for recovery, this has been accounted for. However, it is possible that the ester seen in the analysis comes completely from this route.

The total auxin content was significantly higher in Composition 2 than in Composition 1, as was the total cytokinin. This is may be because many of these compounds are not particularly water soluble and the temperature treatment used to produce Composition 2 may have assisted such compounds to dissolve.

In contrast, the total gibberellin content however was higher in Composition 1 than in Composition 2. This could indicate that gibberellins are converting to other molecules in water at 90° C. The concentration of salicylic acid and jasmonates were also higher Composition 1 than in Composition 2. Abscisic acid concentration was found to about the same in both extracts, within experimental error.

In regard to the Control sample, this sample was partitioned between methanol/water and petroleum spirit to remove any waxes and chlorophyll. This protocol resulted in a comparable quantity of auxins to Composition 1, and similarly, no IAA.

Control gave a greater quantity of cytokinins than Composition 1, but not as much as Composition 2. Notably, the cytokinin content of Control was predominated by ortho-topolin, whereas Composition 2 was predominated by para-topolin. Both ortho- and para-topolin have low solubilities in water at room temperature, so it is possible that selective extraction occurred by the ethanol/water used for Control or the higher temperature of heat treatment used for Composition 2. It is also possible that differential solubility arises from the potential of ortho-topolin to form a hydrogen bond between the phenolic hydroxyl group and the amine on the 6 position of the ring. In this regard, it can be seen from analysis of the Composition 1, Composition 2, and Control, that extraction of cis-zeatin, benzyladenine and ortho-topolin is incomplete using water extraction.

From each extract the original concentration of the growth hormone in the plant was estimated. This estimate of course depends on the efficiency of extraction, which would be variable. Nevertheless, estimates of the original concentrations (in pmol/g and ng/g, respectively) in seaweed based on concentrations detected in the respective samples are set out in Table 1.

Relevantly, these respective concentrations set out in Table 1 are also proportionate to the concentration of the respective plant hormones as present in Composition 1 and Composition 2 (and Control), with both Composition 1 and Composition 2 featuring a ratio of 10 g fresh weight seaweed to 100 mL water, or 10% seaweed by weight.

Comparison of Composition 1 and Composition 2 with Existing Seaweed Formulations The concentrations of the respective plant hormones as present in Composition 1 and Composition 2 are given in Table 2. Additionally, the plant hormones detected in Composition 1 and Composition 2 can be compared to certain commercial seaweed formulations for which figures are available, with this information also presented in Table 2.

The best characterised commercial extract is Kelpak (Stirk and Van Staden 1997, Stirk et al. 2004, Masny et al. 2004, Papenfus et al. 2012, Stirk et al. 2014). The technical sheet for Kelpak available from the manufacturer gives the total concentrations of auxins and cytokinins in Kelpak to be 11000 μg/mL and 30 μg/L respectively. However, these figures are substantially higher than the concentrations reported in the scientific literature at 7.2 μg/L and 5.7 μg/L respectively (Stirk et al. 2004, Stirk et al. 2014 b Tay et al. 1985, Tay et al. 1987). This discrepancy probably arises from the means of determination, which in the technical sheet may be based on a biological response test, whereas in the scientific literature is based on chemical analysis. Thus, the higher value probably indicates the effect of the auxin and cytokinin content, and thus is a catch all, whereas the chemical analysis only looks at specific examples. It is also thought that some of cytokinin-like activity arises from amino acid derived betaines which have been shown to have cytokinin like activity (Blunden and Gordon 1986). Thus, the analysis described herein is not expected to necessarily equal the total auxin and total cytokinin content measured by biological response.

The chemical analysis performed herein indicates that the auxin, gibberellin and abscisic acid content, overall, is 2 orders of magnitude higher in both Composition 1 and Composition 2 than in Kelpak. The cytokinin content is also higher in Composition 2, but lower in Composition 1, than in Kelpak. In both cases however, the specific compounds present differ.

The auxin content in Composition 1 and Composition 2 is comparable to that in another commercial composition, Seasol, but the cytokinin content is lower. Notably however, Seasol corresponds to 1 L of extract per 1.5 kg of wet seaweed (Tay et al 1987). The concentrations of the auxins and cytokinins which have been determined in other commercial compositions Kelpro and Maxicrop are much higher than in Composition 1 and Composition 2. However, these products are designed for preparation at relatively high dilutions, and Maxicrop is a powder, not a solution.

Discussion of the classes of growth hormones identified in Composition 1 and Composition 2 and comparison with analysis that has been performed for Kelpak, in the context of plant growth stimulation, follows. It will be appreciated however, that the overall contribution of hormones to plant growth stimulation is complex, and the relative activity of each of the growth hormones and the interaction and balance between them is also important.

Auxins

There are two main tests for activity of auxins: The *Avena* test and the Pea test. Compounds which show 'primary' growth promoting in the Pea test are not always active in the *Avena* test. In the primary (Pea) test, indoleacetic, indolepropionic, indolebutryric acids and their esters all display similar activity, however indolecarboxylic acid and its esters do not (Koepfli et al. 1938). On the basis that IAA, IPA, IBA, ILA and their esters and amides have similar activity and using $\frac{1}{28}^{th}$ of the activity for IGAMe to make it equivalent to IAA (Pilet 1971), Kelpak is reported to have a total of 33.91 pmol/mL of IAA equivalents, whereas Composition 1 has 28 pmol/mL, Composition 2 has 1998 pmol/mL and Control has 236 pmol/mL.

Cytokinins

The activity of cytokinins has been measured in a number of tests, of which the most common is the tobacco callus bioassay (Reinert and Yeoman 1982). It can be seen from Table 4 that there is significant variation in activity between the cytokinins. The minimum concentration required for an effect and the optimum concentration in the tobacco callus assay are much better for iP and tZ than the other cytokinins, with BA still quite good.

The papers referenced in Table 4 do not have figures for the topolins, but it has been reported that mT and its riboside have similar minimum concentrations required for activity to tZ and BA whereas oT and oTR are 100 fold worse (i.e. similar to DHZ). mT also had similar optimum concentration to tZ (Holub et al. 1998). The activity of pT in this assay has not been reported. In a *Phaseolus lunatus* callus bioassay, one half of the maximal growth is achieved at about 0.02 µM for tZ, 0.04 µM for BA, 0.3 µM for cZ, 0.05 µM for mT, 1 µM for oT and 30 µM for pT (Mok et al. 2005).

On this basis, cytokinin activity in Composition 2 could be expected to be primarily attributable to iP and this may be significantly lower in Composition 1 due to the lack of this compound. Nevertheless, the response of plant growth to different cytokinins can vary depending on the specific circumstances. For example, in the *P. lunatus* callus bioassay, iP, iPR, BA and cZ have very similar minimum/optimum concentrations at 0.01/3 µM, 0.03/3 µM, 0.01/3 µM and 0.03/3 µM respectively and tZ and tZR are 10-fold better at 0.001/0.3 µM and 0.003/0.1 µM respectively. In the *Phaseolus vulgaris* callus assay, BA (0.001 µM) is about 10-fold better than tZ (0.0301), tZR (0.03 µM) and cZ (0.01 µM), 100-fold better than iP (0.3 µM) and 1000-fold better than iPR (1 µM) for minimum concentration, but similar to tZ (3 µM), tZR (3 µM) and cZ (3 µM) for optimum concentration, 10-fold better than iP (10 µM) and 30-fold better than iPR (30 µM) (Matsbuara 1990).

Ratio of Auxins to Cytokinins

The relative amounts of auxins and cytokinins may be significant in the context of plant growth stimulation. For example, the cell fate in a particular tissue depends on the ratio of auxins to cytokinins. In the root meristem, auxins induce cell division, whereas cytokinins promote a switch to differentiated cells through inhibiting the auxin signal. In the shoot meristem however, cytokinins promote stem-cell proliferation and inhibit cell differentiation whereas auxins trigger primordium initiation through suppression of cytokinin biosynthesis (Su et al. 2011).

Kelpak is stated to be formulated for root growth with an auxin:cytokinin ratio of 367:1, which is asserted to be optimal. An advertising leaflet distributed by Kelpak suggests an auxin:cytokinin ratio of 15:1 produces a callus, 150:1 roots, 1:150 shoots and 0:1 no growth. Notably, both Composition 1 and Composition 2 have a much greater predominance of auxins over cytokinins. This may suggest that the compositions would be particularly beneficial for promoting root growth.

Gibberellins, Salicylates, Abscisic Acid and Jasmonates

The gibberellin analysis performed herein is limited by not having standards for GA1 and GA4. It should also be noted that the figures obtained appear to be very high by comparison with other analyses. The LCMS traces for the accurate masses corresponding to GA3, GA6 and GA7 were quite noisy, so it is possible that these values are artificially enhanced by other impurities in the region. Similar can be observed for abscisic acid and the jasmonates.

The content of salicylic acid and jasmonates cannot be compared to other products as there is no comparable analysis. However, the presence of jasmonates in Composition 1 and Composition 2 may confer advantages for wound recovery, pathogen attack, water stress, flowering, fruiting and tuber formation. It is also notable that the abscisic acid content detected in Composition 1 and Composition 2 is much higher than that in Kelpak.

Detailed Materials and Methods

General Considerations

All solutions of fractions and standards were prepared using volumetric flasks and automatic pipettes. Petroleum spirit used was the fraction boiling at 40-60° C.

Preparation of Control Sample

To produce the Control, air dried seaweed (50.007 g) was dried over phosphorus pentoxide for 3 days at 4-10 mbar to give 37.418 g of dried seaweed. This was ground with a mortar and pestle then sieved through a 0.433 mm sieve to give 28.574 g of sieved material and 8.773 g of material which did not pass through the sieve. 25.003 g of this material was stirred with 80:20 methanol:Milli-Q water for 24 h at room temperature then filtered through a porosity 3 sintered glass filter.

The filtrate was stored in the fridge at 6° C. The solid material was resuspended in 80:20 methanol:Milli-Q water and stirred at room temperature (6-22° C.) for 3 days then filtered again and the filtrate combined with the previous one. The solid was then resuspended in 80:20 methanol:Milli-Q water and heated to 70° C. for 4 h. The suspension was filtered hot and the solid washed with ethanol (50 mL). The combined filtrates were concentrated under reduced pressure to give a dark green semisolid (4.504 g). This was taken up in 75:25 methanol:Milli-Q water (100 mL) and petroleum spirit. The precipitated solid was filtered off, washed with further petroleum spirit (25 mL which was combined with the filtrate, then 100 mL) and air dried, then dried under vacuum overnight over phosphorus pentoxide to give an off white solid, 1.712 g which appeared to be an inorganic salt due to lack of peaks in the NMR spectrum.

The two phases of the filtrate were separated and the methanol/water phase washed with the 100 mL of the second wash by petroleum spirit of the solid described above, then further petroleum spirit (3×100 mL). The combined petroleum spirit phases were extracted with 75:25 methanol:Milli-Q water (3×100 mL). The combined methanol/water extracts were then concentrated under reduced pressure to a green-brown semisolid. (2.745 g). This solid was taken up in 1:1 ethanol:Milli-Q water and the soluble material decanted onto the DEAE Sephadex column described herein.

Standards

Standards for LC-MS analysis of the following compounds were obtained:
  indole-3-carboxaldehyde (IAld)
  indole-3-carboxylic acid (I3CA)
  tryptophol (IEt) [3-(2-hydroxyethyl)indole]
  indole-3-acetamide (IAM)
  indole-3-carboxylic acid methyl ester (I3CAMe)
  indole-3-acetic acid (IAA)
  indole-3-propionic acid (IPA)
  indole-3-glyoxylic acid methyl ester (IGAMe)
  indole-3-pyruvic acid (IPiA)
  indole-3-acetic acid ethyl ester (IAAEt)
  indole-3-butyric acid (IBA)
  DL-indole-3-lactic acid (ILA)
  4-chloroindole-3-acetic acid (4ClIAA)
  DL-indole-3-lactic acid methyl ester (ILAMe)
  indole-3-acetyl-glycine (IAGLY)
  melatonin (M) [N-acetyl-5-methoxytryptamine]
  indole-3-acetyl-1-alanine (IAAla)
  N6-isopentenyladenine (IP)
  trans-zeatin (tZ)
  cis-zeatin (cZ)
  dihydrozeatin (DHZ)
  kinetin (K)
  N6-benzyladenine (BA)
  ortho-topolin (oT)
  para-topolin (pT)
  N6-isopentenyladenosine (iPR) (riboprine)
  trans-zeatin riboside (tZR)
  dihydrozeatin riboside (DHZR)
  N6-benzyladenosine (BAR)
  dihydrozeatin riboside-o-glucoside (DHZROG)
  gibberrellin A3 (GA3)
  gibberellin A6 (GA6)
  gibberellin A7 (GA7)
  salicylic acid (SA)
  (+)-cis,trans-abscisic acid (S-ABA) natural isomer
  (−)-jasmonic acid (JA)
  (−)-jasmonic acid methyl ester (MeJA)

To prepare the standards, cordycepin (23.80 mg) was made up in 250 mL of 10% Milli-Q water in methanol in a volumetric flask. Solutions of the standards were made up in this solution then serially diluted with 10% Milli-Q water in methanol. For ILA, BA, MeJA, DHZR, tZ, K, tZR, BAR, ICA, IAAGly, IAA-Ala and DHZOGR a mixed calibration standard was made up by taking 200 L of the highest concentration of each calibration standard and combining them then serially diluting them with 10% Milli-Q water in methanol. A mixed calibration standard ("All standards" sample) made up similarly was also injected at regular intervals during each LCMS run to test reproducibility.

Preparation of DEAE Sephadex Column

DEAE Sephadex A-25 was obtained from Pharmacia Co. 120 g of DEAE Sephadex A25 was swollen with deionised water then the excess water decanted off. It was then mixed with 0.5M hydrochloric acid (1 L), allowed to settle and the liquid decanted off. This procedure was repeated with further hydrochloric acid (1 L) then deionised water (2×1 L) then 0.5M sodium hydroxide solution, further deionised water (2×1 L) then 1M sodium acetate solution (1 L). It was then mixed with further 1M sodium acetate solution (1 L) then allowed to stand at room temperature for several hours. The slurry was then poured into a 7.5 cm internal diameter glass column and eluted with Milli-Q water until the pH of the eluted water was the same as the water loaded on. It was then eluted with 1:1 Milli-Q water:ethanol (2×1 L), slurried with 1:1 Milli-Q water:ethanol in the column to remove air bubbles twice and allowed to settle giving a column height of 11 cm. Finally the excess solvent was eluted through.

Separation on DEAE Sephadex

Composition 1, Composition 2, and Control samples (250 mL) were loaded directly onto the DEAE Sephadex column, then eluted successively with 1:1 ethanol:Milli-Q water, then 1%, 10%, 20%, 30%, 40%, 50%, 60% and 80% glacial acetic acid in 1:1 ethanol:Milli-Q water (1 L each) then 100% glacial acetic acid (2 L). Elution was carried out using gravity only. Eluate was collected from when the extract was loaded on throughout the elution and concentrated under pressure at room temperature to give 13 fractions (fractions 1 and 2, 500 mL each; fractions 3-13 1 L each). The fractions were taken up in 2 mL or 5 mL of methanol in volumetric flasks. In some fractions, methanol insoluble material was dissolved in water and analysed separately. In other fractions, solid material from degradation of the column was filtered off and washed with a little solvent, then the filtrates reconcentrated. In two cases, a portion of the fraction concentrate was dissolved in methanol (5 mL) and the amount calculated taking this into account.

Regeneration of DEAE Sephadex Column

Following the completion of elution, the column was washed with 2M sodium chloride solution (2 L) then 0.5M sodium hydroxide solution (2 L), then deionised water until the pH of the eluate was the same as the water loaded on. It was then eluted again with 0.5M sodium hydroxide (1 L) then deionised water until the pH of the eluate was the same as the water loaded on. It was then eluted with 1M sodium acetate solution (1 L) then mixed with further sodium acetate solution (1 L) and stood for several hours before being eluted with deionised water until the pH of the eluate was the same as the water loaded on. It was then eluted with 1:1 Milli-Q water:ethanol (2×1 L), slurried with 1:1 Milli-Q water:ethanol in the column to remove air bubbles twice, allowed to settle and the excess solvent eluted through. Finally the column was eluted with 1:1 Milli-Q water:ethanol (1 L).

Separation of a Mixture of Standards to Determine Recovery

200 µL each of 90% methanol in water solutions of DHZ (0.105 mg/mL), iP (0.110 mg/mL), iPR (0.106 mg/mL), IAA (0.162 mg/mL), IBA (0.208 mg·mL), ILA (0.183 mg/mL), ABA (0.166 mg/mL), cZ (0.111 mg/mL), cZOG (0.500 mg/mL), tZ9G (0.108 mg/mL), tZOG (0.084 mg/mL), BA (0.139 mg/mL), IPA (0.111 mg/mL), IAAEt (0.133 mg/mL), IEt (0.144 mg/mL), IAld (0.125 mg/mL), IPiA (0.136 mg/mL), pT (0.0125 mg/mL), oT (0.0147 mg/mL), IGAMe (0.250 mg/mL), I3CAMe (0.282 mg/mL), M (0.282 mg/mL), JA (0.224 mg/mL), MeJA (0.524 mg/mL), SA (0.216 mg/mL), IAM (0.236 mg/mL), GA3 (0.26 mg/mL), GA7 (0.28 mg/mL) and GA6 (0.20 mg/mL) were combined. This mixture was loaded onto the DEAE Sephadex column described above and the separation carried out as described above for the separation of the seaweed extracts. The content was determined using LCMS as described below, then divided by the original content to determine % recovery.

Preparation of LCMS Samples 0.900 mL of each concentrated fraction dissolved in methanol as described above was diluted with a solution of 0.100 mL of Milli-Q water containing 0.152 mg/mL of cordycepin as an internal standard then centrifuged for 20 min at 20,000 g. They were then filtered through a 0.2 µM PTFE syringe filter.

Liquid Chromatography-Mass Sectrometry (LCMS)

Mass spectrometric analyses were performed on a Thermo Scientific™ Q Exactive mass spectrometer fitted with a HESI-II ion source. Positive and negative ions were recorded in an appropriate mass range at 140,000 mass resolution. The probe was used with 0.3 ml/min flow of solvent. The nitrogen nebulizing/desolvation gas used for vaporization was heated to 400° C. in these experiments. The sheath gas flow rate was set to 35 and the auxiliary gas flow rate to 25 (both arbitrary units). The spray voltage was 3.5 kV for positive ion and 3.0 kV for negative ion, and the capillary temperature was 320° C.

Chromatographic analysis was performed using a Dionex 3000 UHPLC system with a Diode Array Detector. The Chromatographic conditions were as follows:

Column: Thermo Scientific™ Hypersil Gold (50×2.1 mm, 1.9 µm particle size)

Mobile Phase B: 100% Methanol with 0.1% formic acid

Mobile Phase C: 90% Milli-Q Water, 10% Methanol with 0.1% formic acid

Gradient: 95% C for 2 minutes, changing to 100% B over 10 minutes. Held at 100% B for 8 minutes. Changed to 95% C over 3 minutes, then held for 2 minutes. The mass spectrometer did not collect data for the last 5 minutes.

Flow Rate: 0.300 ml/min

Column Temperature: 30° C.

Sample Injection Volume: 10 µl for samples, 1 µl for "All standards" sample

LCMS data was processed using Thermo Scientific™ Xcalibur™ software. Peaks were integrated manually. Calibrations standards were run under the same conditions as samples. Calibration curves were constructed from the calibration standards (FIGS. 1-23) and were used to determine the concentration in the samples. Non linearity in the calibration curves occurs due to saturation at higher concentrations.

Figure 30:
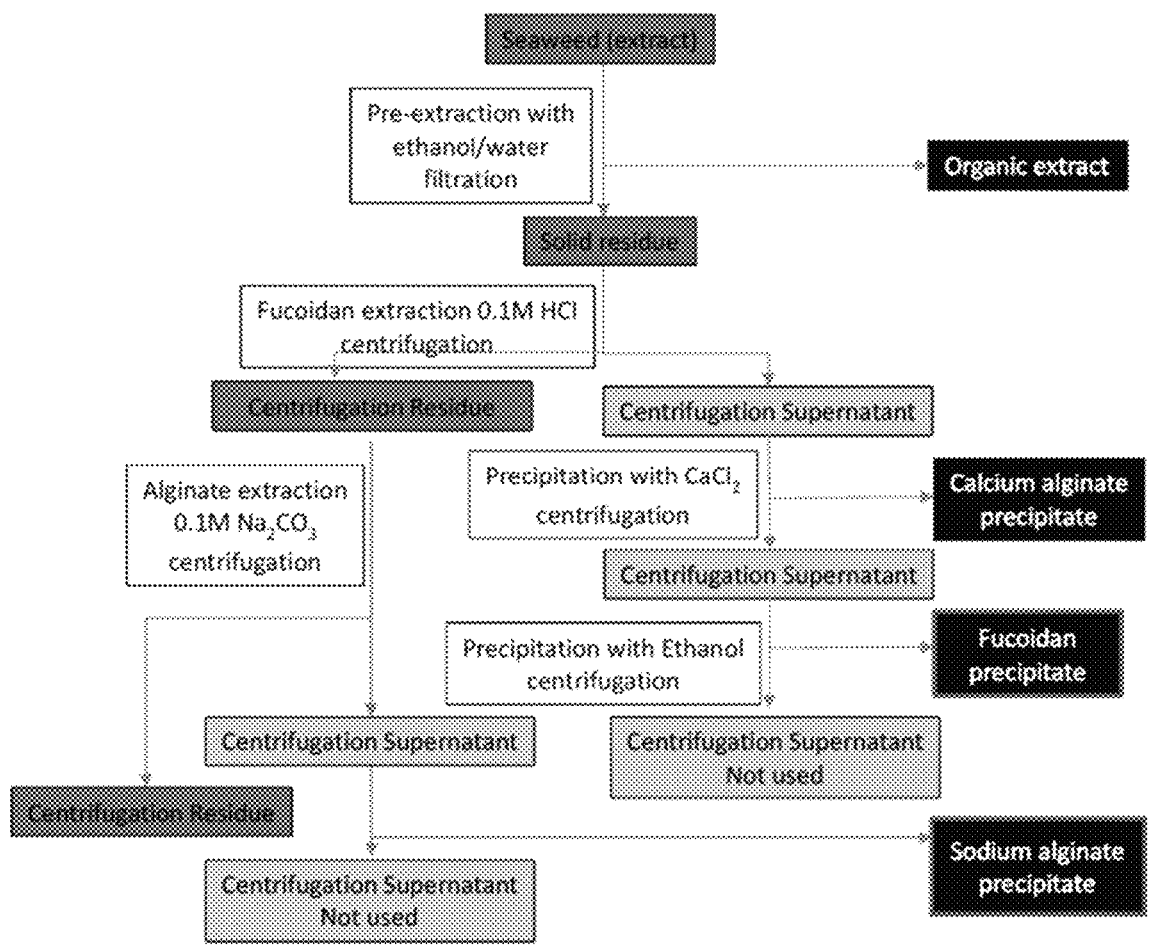
FIG. 30 sets forth a schematic diagram of an extraction process for alginate and fucoidan from seaweed.

Example 3. Determination of Fucoidan and Alginate Concentrations in Seaweed Compositions Summary of Procedures and Results Composition 1 and Composition 2, along with a dried sample corresponding to the seaweed used to obtain these compositions, were processed as schematically depicted in FIG. 30, based on the method of Yuan and Macquarrie 2015.

The extraction method used herein results in firstly, extraction of growth hormones from seaweed to produce a sample similar as the Control sample described in Example 2, and subsequent extraction of the fucoidan and alginate. It will be appreciated that this method can be used to prepare up to three independent compositions from seaweed: (1) a composition comprising plant growth hormones; (2) a composition comprising fucoidan; and (3) a composition comprising alginate.

For this process, small molecule organic compounds were extracted out first (including the growth hormones) using 80:20 ethanol:water. As alginate and fucoidan are precipitated from water with ethanol, it was expected that extraction of these two polysaccharides using this solvent system would be minimal.

Dilute hydrochloric acid was then used to extract the fucoidan and the mixture was centrifuged. Calcium chloride was added to the supernatant to precipitate any alginate that was present in the acidic supernatant. The calcium alginate was separated by centrifugation and the supernatant was diluted with ethanol to precipitate the fucoidan. The residue from the initial centrifugation was treated with aqueous sodium carbonate to solubilise the alginate as the sodium salt. After centrifugation the supernatant was treated with ethanol to precipitate the sodium alginate.

Alginate

Alginate was precipitated as calcium alginate $[(C_{12}H_{14}CaO_{12})n]$ and sodium alginate $[(C_6H_7NaO_6)n]$. 100 mL of Composition 1 delivered 5.53 mg of calcium alginate and 1.017 g of sodium alginate, corresponding to 4.99 mg and 904 mg respectively or a total of 909 mg of alginic acid. 100 mL of Composition 2 delivered 0.59 mg of calcium alginate and 940 mg of sodium alginate, corresponding to 0.53 mg and 836 mg respectively or a total of 837 mg of alginic acid. As such, Composition 1 contained more alginic acid at 9.09 mg/mL than Composition 2 at 8.37 mg/mL.

The ground, dried seaweed delivered 81.03 mg of calcium alginate and 6.633 g of sodium alginate from 25.003 g of dried material. This corresponds to 73.13 mg and 5.897 g respectively or a total of 5.970 g of alginic acid. However, a sample of the dried material was further dried over phosphorus pentoxide for 4 days at 3-4 mbar and lost a further 7.7% of its weight, so the 25 g corresponds more accurately to 23.996 g. It is still possible that further drying may decrease this weight by a little more, but this figure is close to dry weight. On this basis, alginic acid constituted 25% of the dry weight of the S. wightii supplied. Notably, this is above the commercially viable level as set out in Rinaudo 2007.

Figure 31:
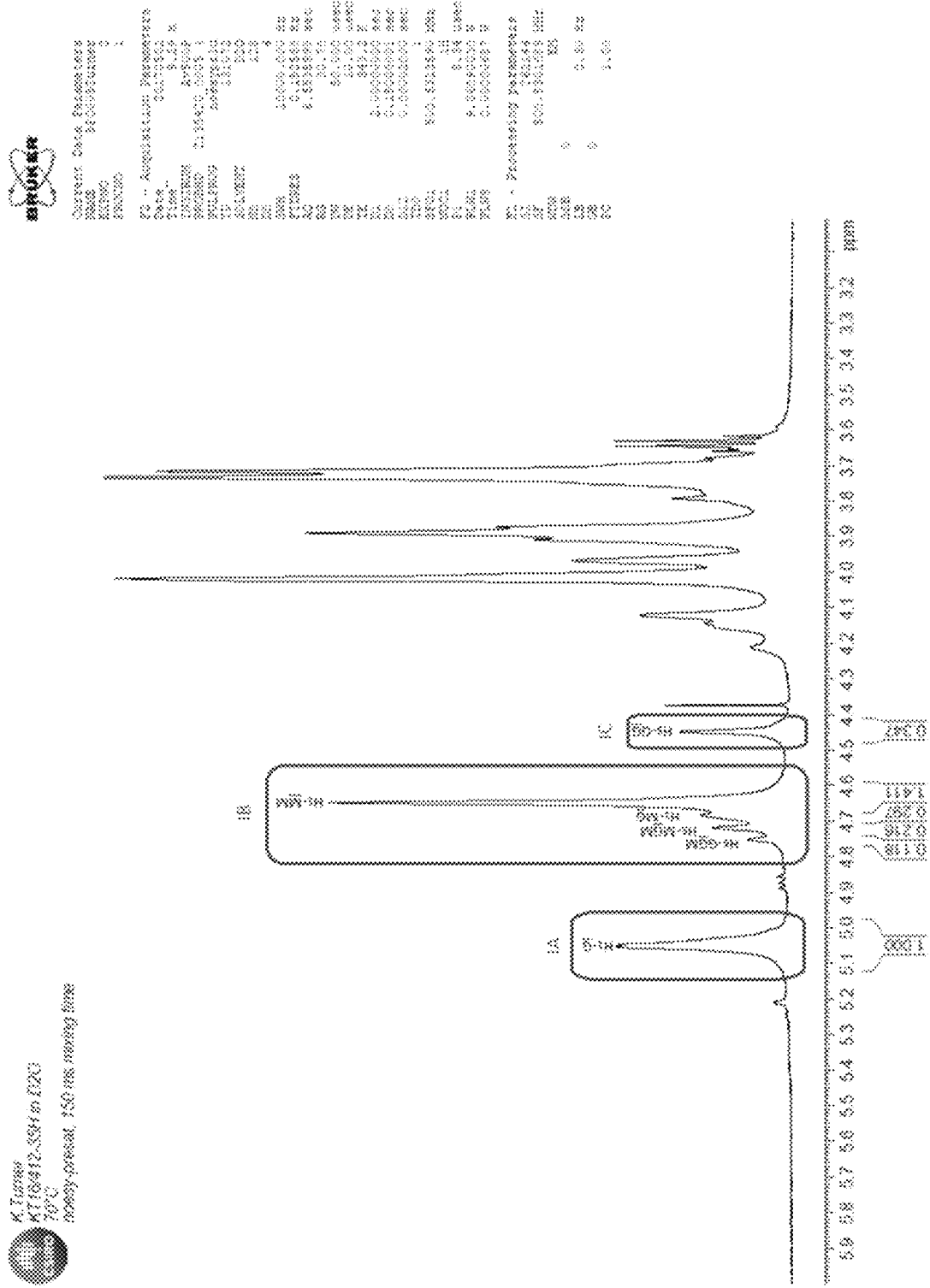
FIG. 31 sets forth a $^1$H NMR spectrum of *S. wightii* alginate.

NMR (FIG. 31) and FTIR spectra (FIG. 32) were obtained, and revealed certain information regarding the structure of the alginate present in the seaweed used to produce Composition 1 and Composition 2.

The 1H NMR spectrum can be used to determine the ratio of (1-4)-β-D-mannuronic acid (M) and α-L-guluronic acid (G) and the percentage of the different blocks in the polymer using the equations of Gradsalen et al (1979).

Figure 2:
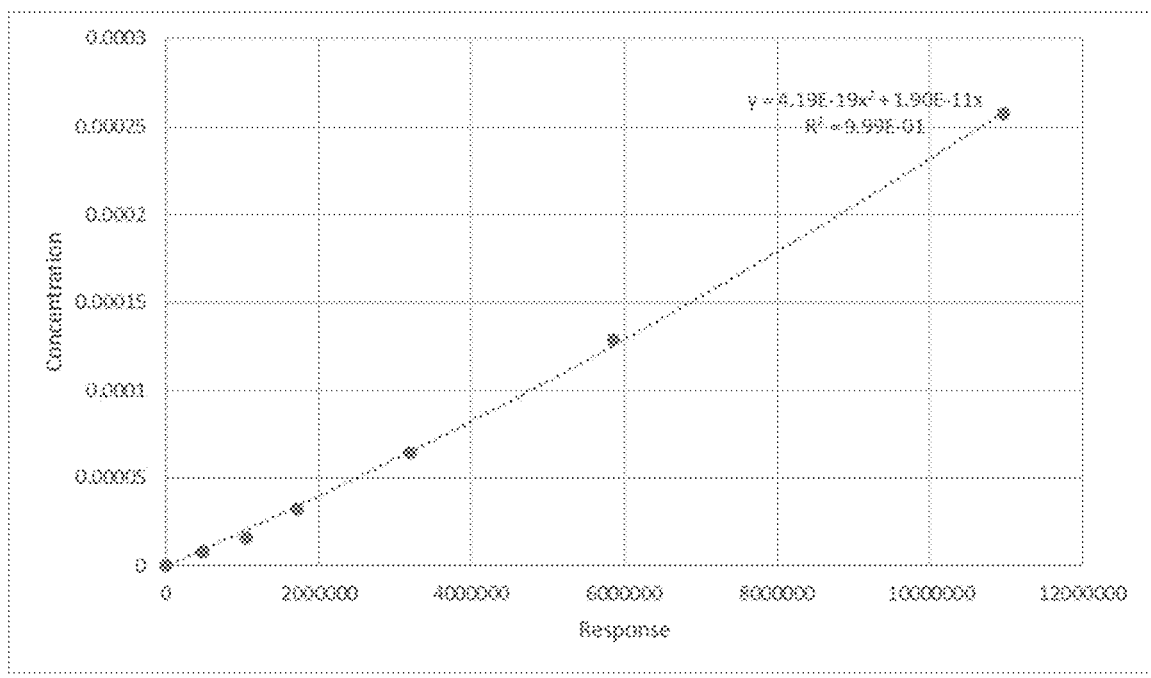
FIG. 2 sets forth an LCMS calibration curve for indole acetic acid ethyl ester.
Figure 3:
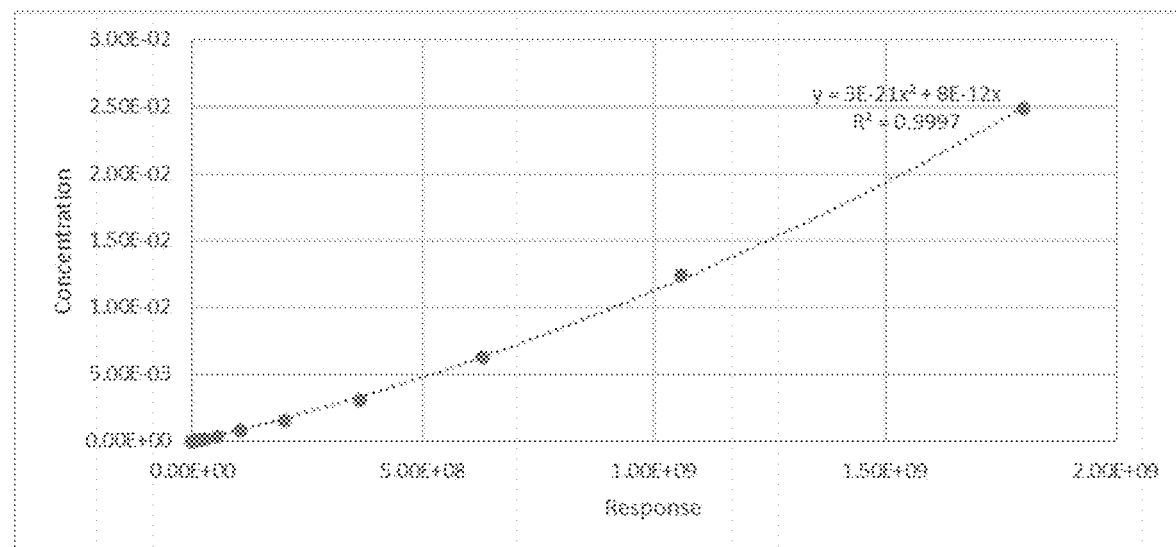
FIG. 3 sets forth an LCMS calibration curve for indolyl-3-acetyl glycine.
Figure 4:
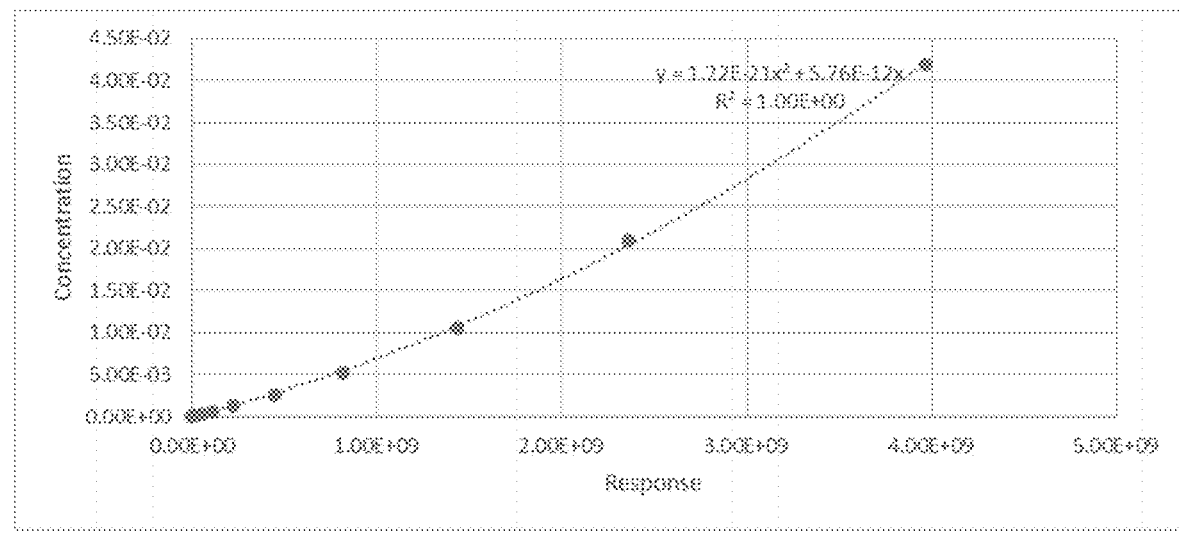
FIG. 4 sets forth an LCMS calibration curve for indolyl-3-acetyl alanine.
Figure 5:
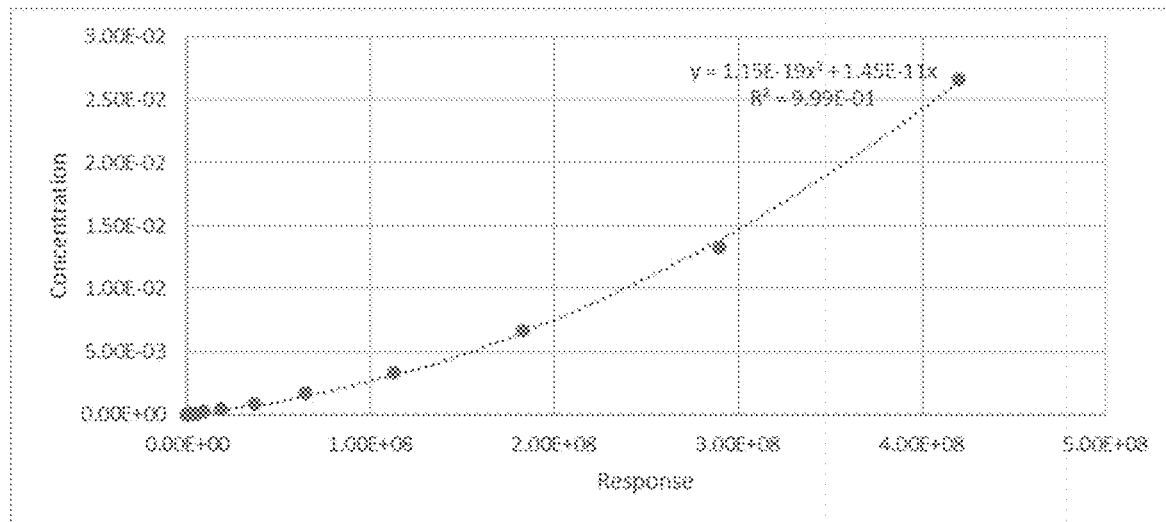
FIG. 5 sets forth an LCMS calibration curve for indole-3-carboxylic acid.
Figure 6:
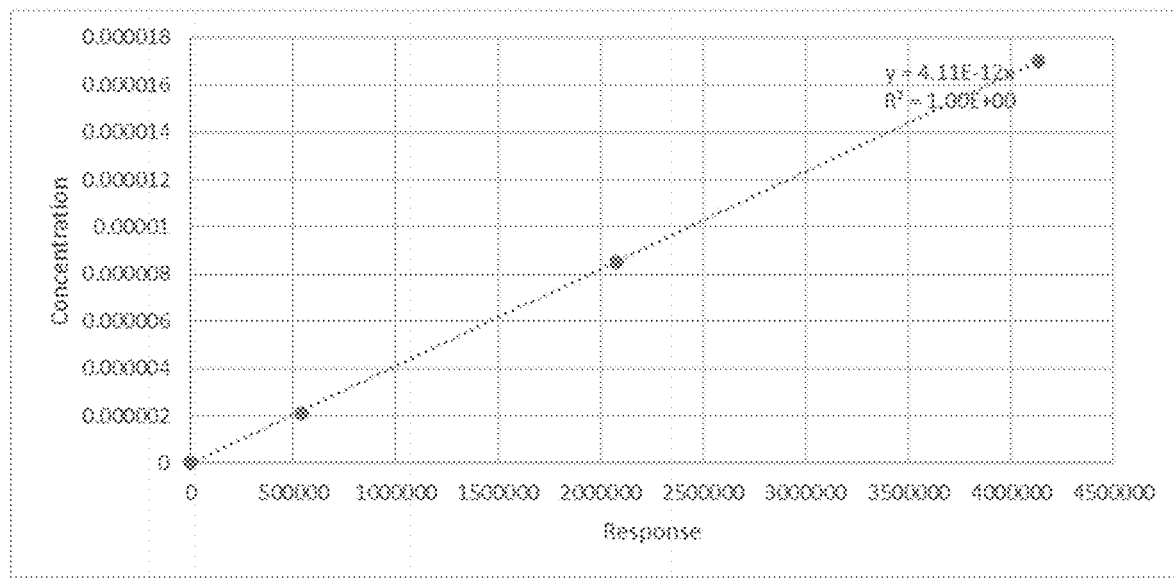
FIG. 6 sets forth an LCMS calibration curve for indole-3-carboxylic acid methyl ester.
Figure 7:
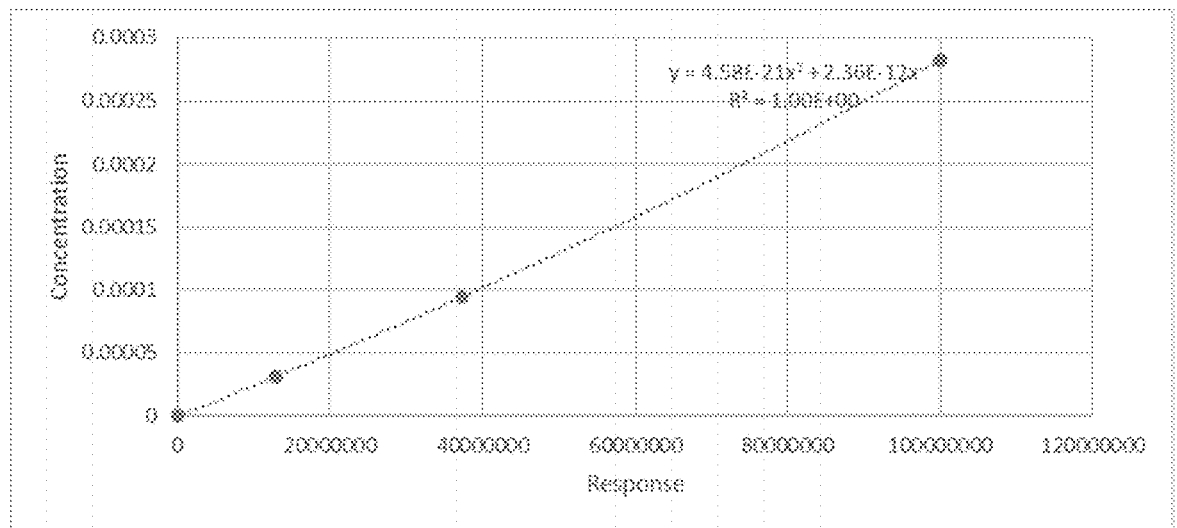
FIG. 7 sets forth an LCMS calibration curve for indole-3-butyric acid.
Figure 8:
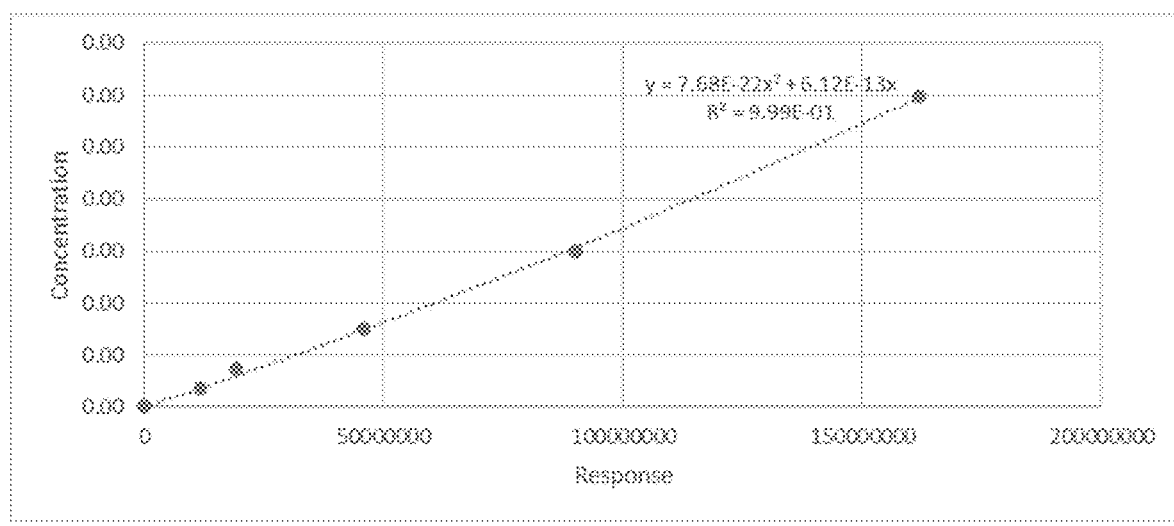
FIG. 8 sets forth an LCMS calibration curve for indole-3-glyoxylic acid methyl ester.
Figure 9:
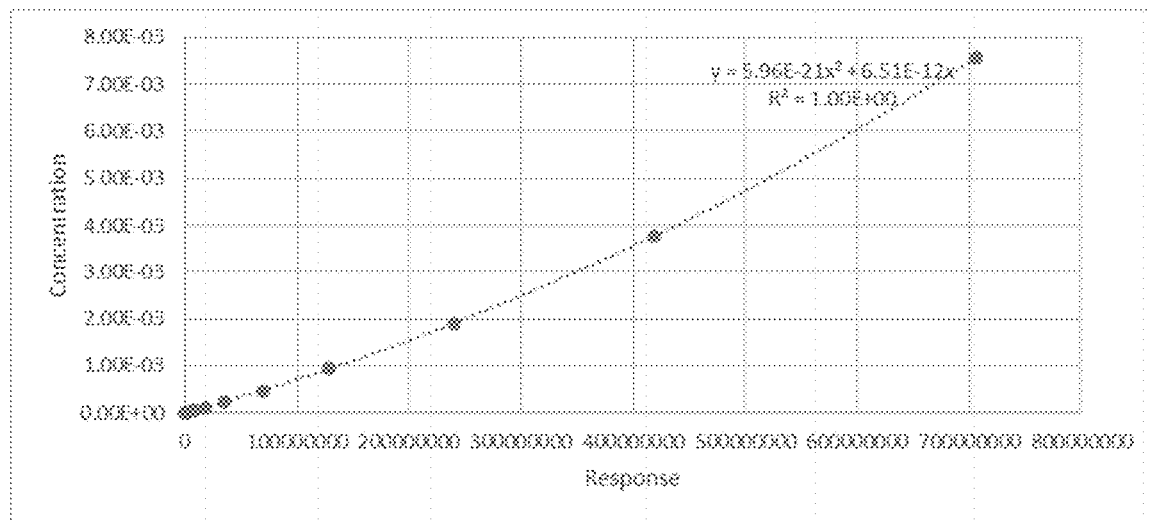
FIG. 9 sets forth an LCMS calibration curve for indole-3-lactic acid.
Figure 10:
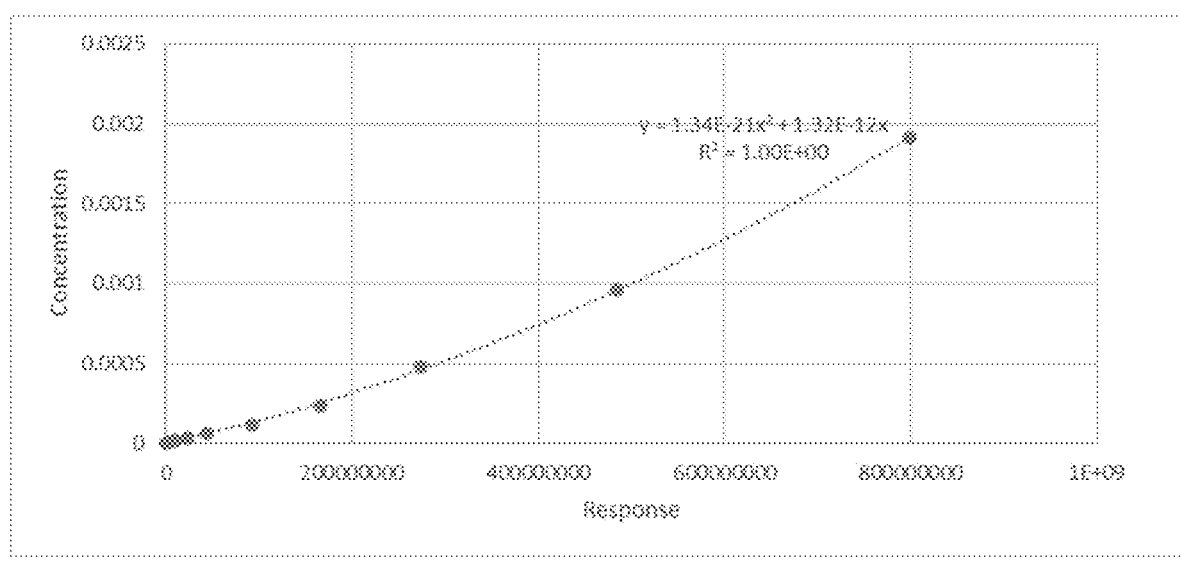
FIG. 10 sets forth an LCMS calibration curve for calibration curve for indole-3-carboxaldehyde.
Figure 11:
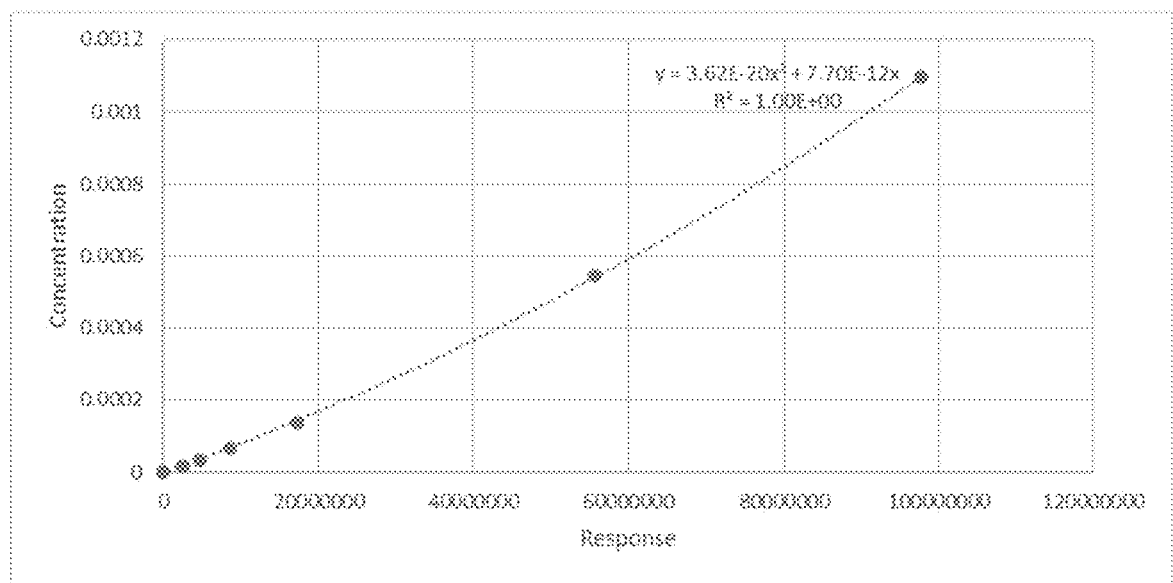
FIG. 11 sets forth an LCMS calibration curve for tryptophol.
Figure 12:
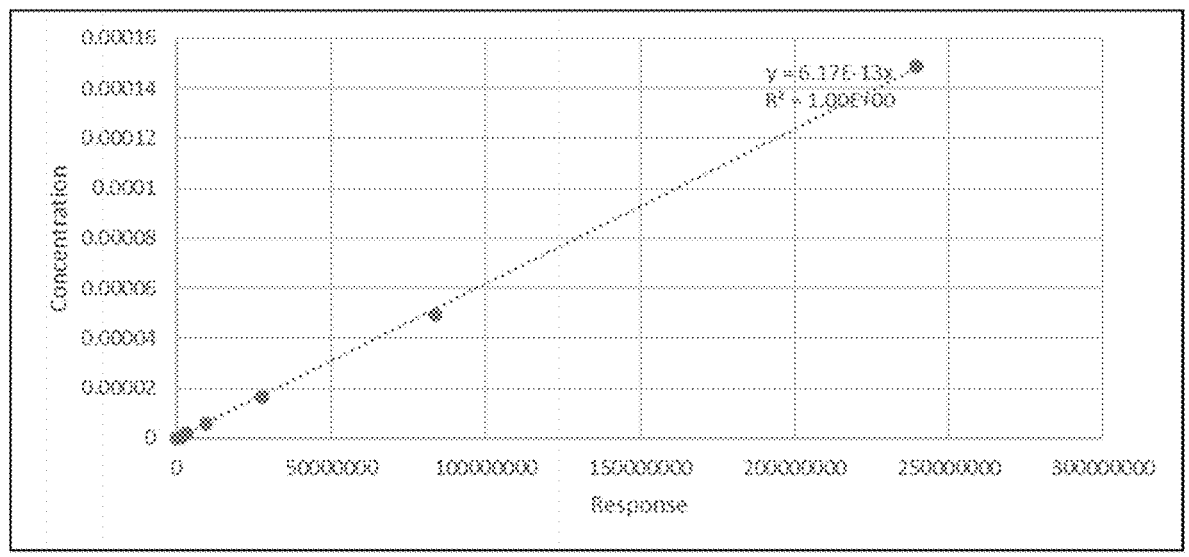
FIG. 12 sets forth an LCMS calibration curve for isopentenyladenine.
Figure 13:
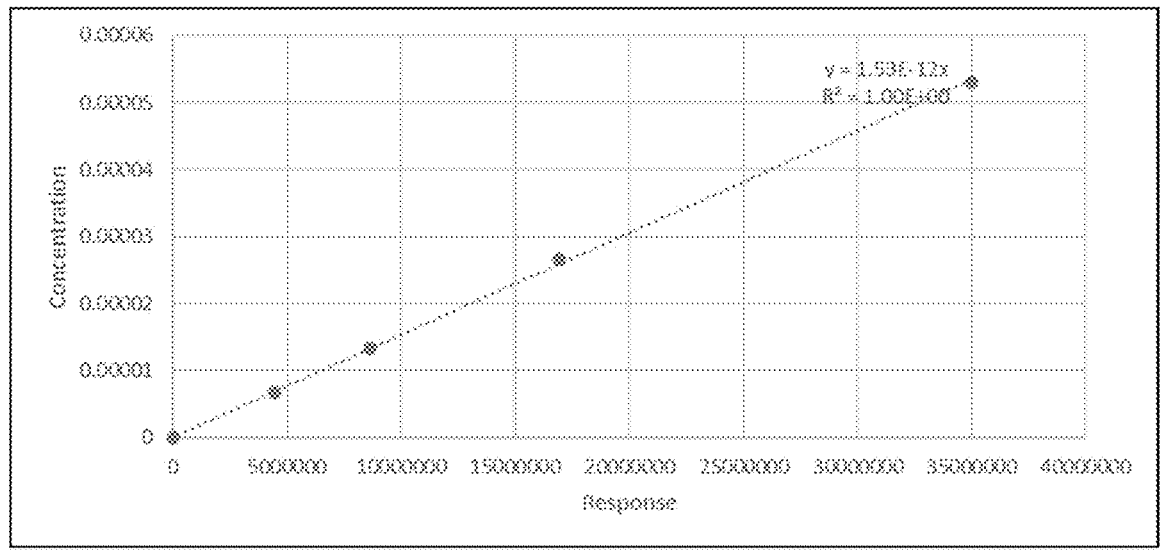
FIG. 13 sets forth an LCMS calibration curve for cis-zeatin.
Figure 14:
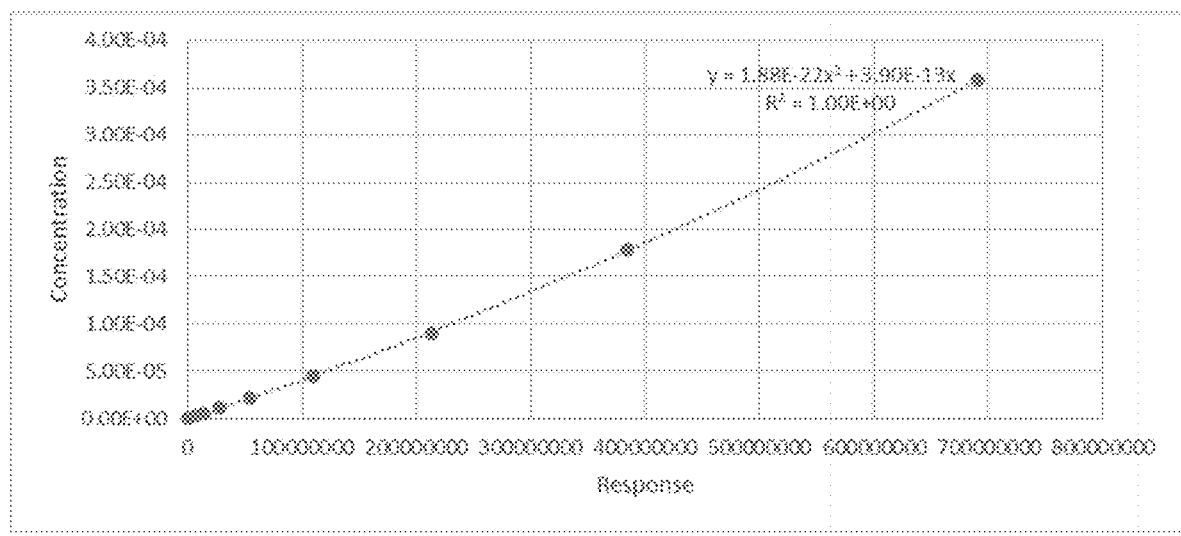
FIG. 14 sets forth an LCMS calibration curve for N6-benzyladenine.
Figure 15:
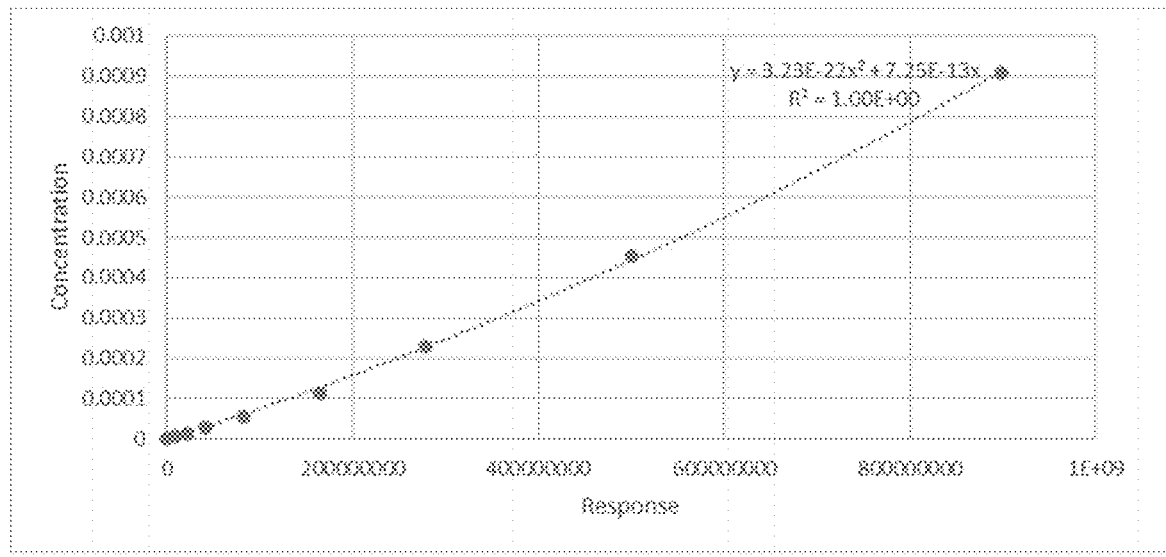
FIG. 15 sets forth an LCMS calibration curve for ortho-topolin.
Figure 16:
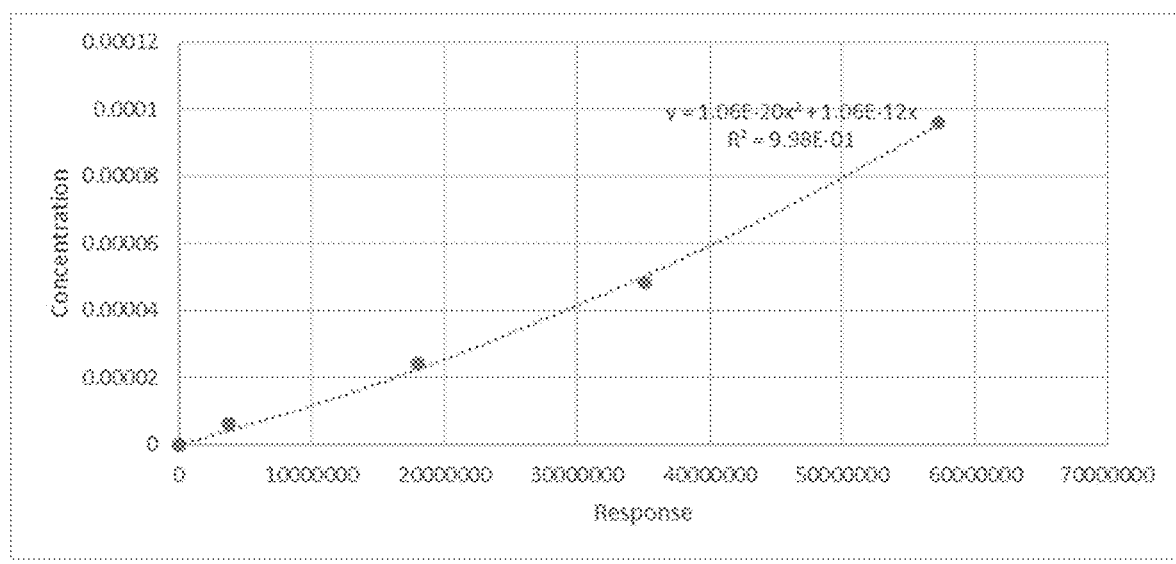
FIG. 16 sets forth an LCMS calibration curve for para-topolin.
Figure 17:
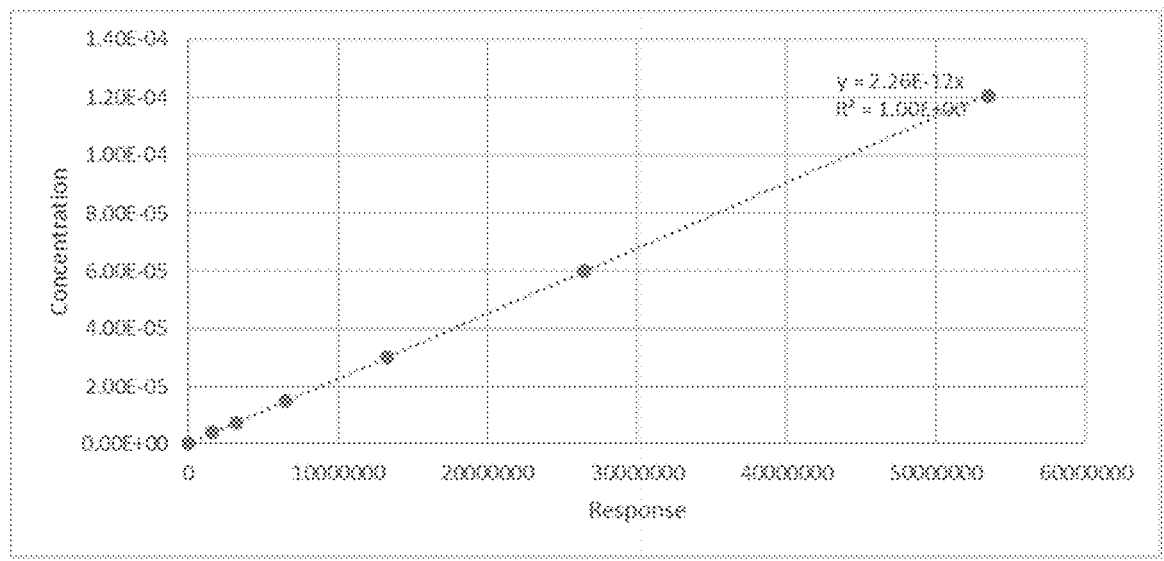
FIG. 17 sets forth an LCMS calibration curve for Gibberellin A3.
Figure 18:
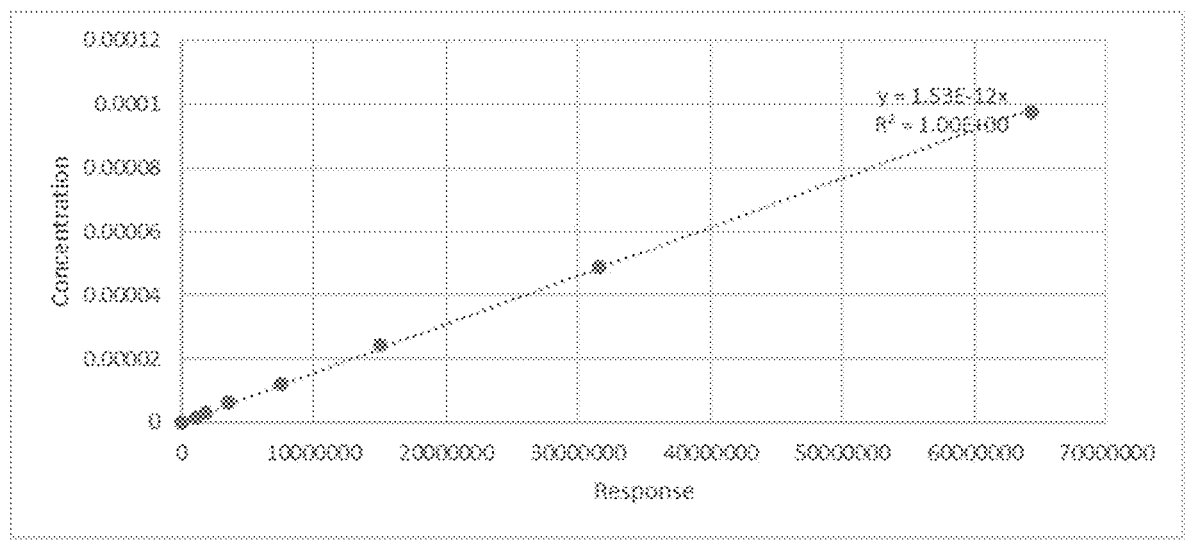
FIG. 18 sets forth an LCMS calibration curve for Gibberellin A6.
Figure 19:
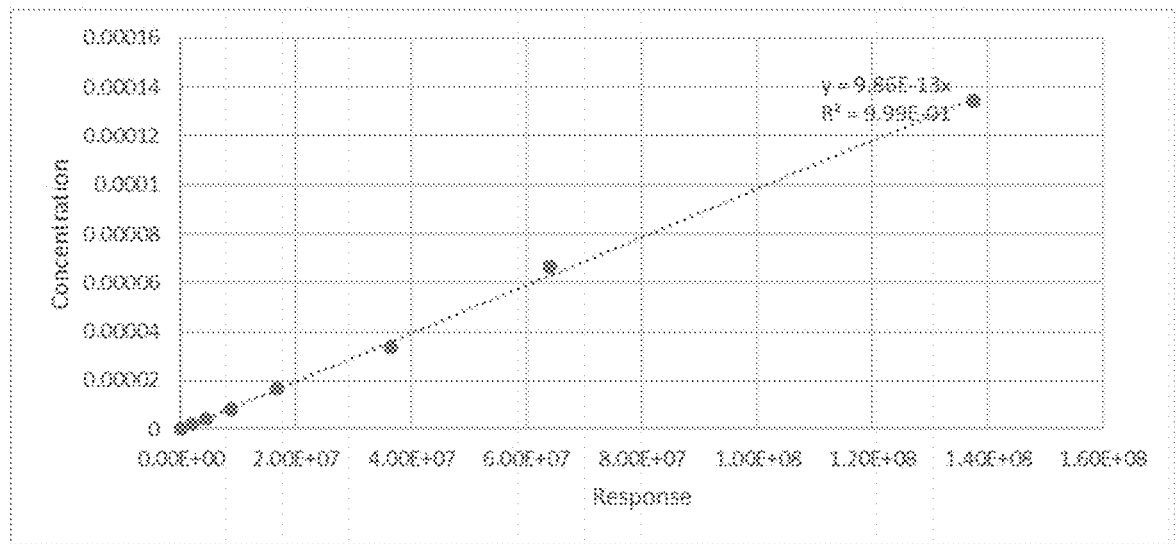
FIG. 19 sets forth an LCMS calibration curve for Gibberellin A7.
Figure 20:
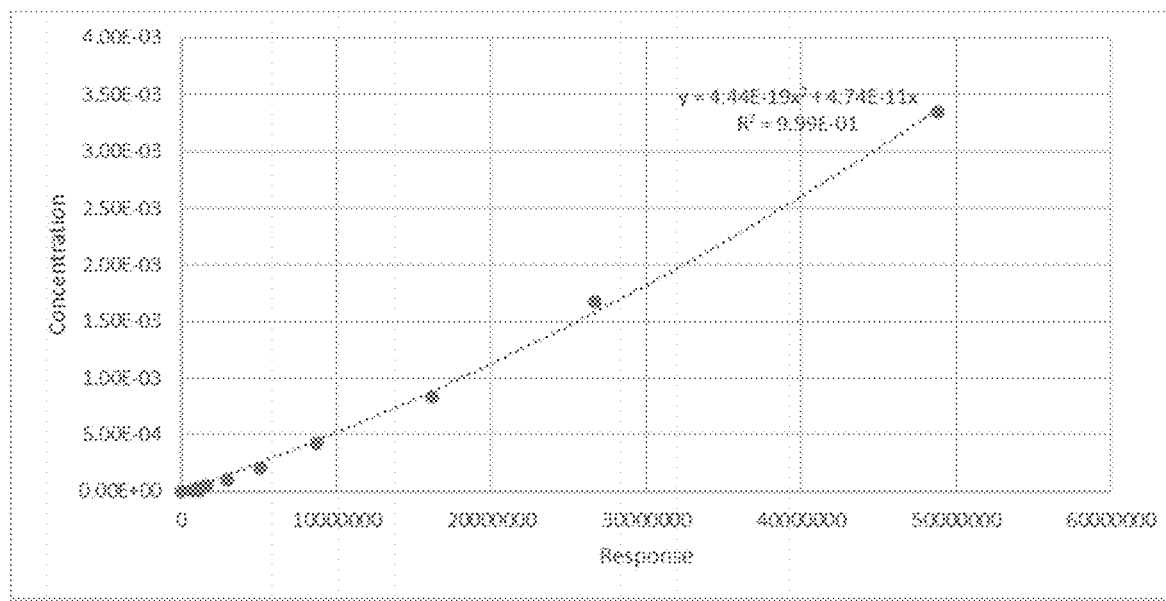
FIG. 20 sets forth an LCMS calibration curve for salicylic acid.
Figure 21:
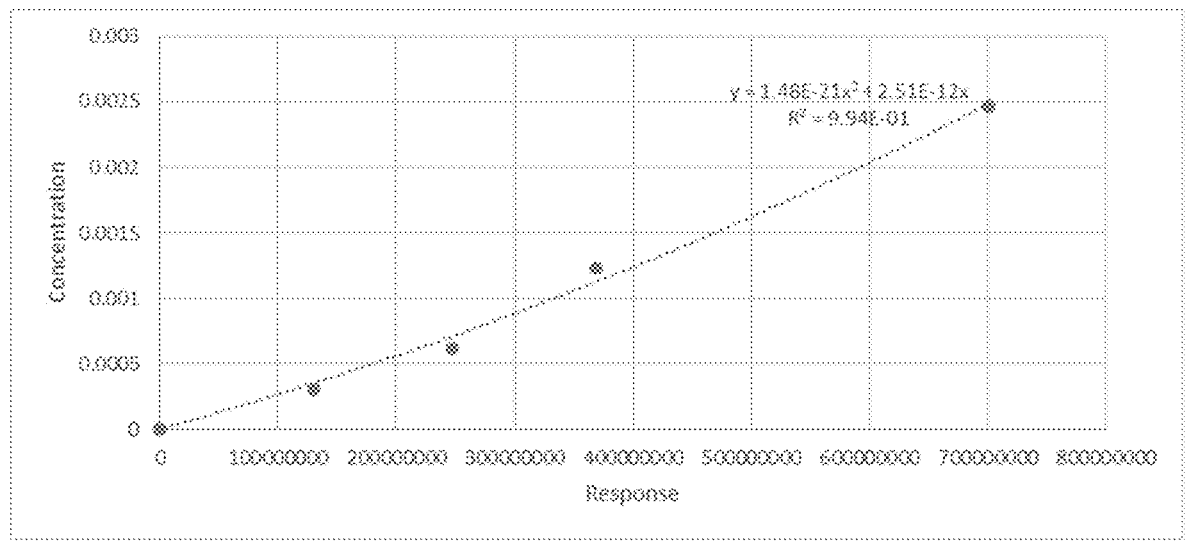
FIG. 21 sets forth an LCMS calibration curve for abscisic acid.
Figure 22:
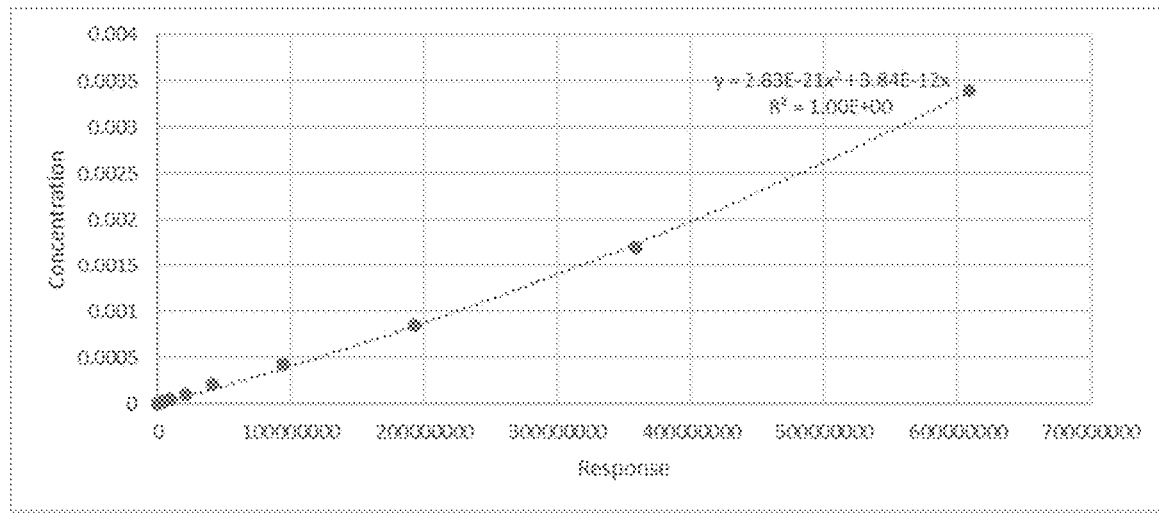
FIG. 22 sets forth an LCMS calibration curve for jasmonic acid.
Figure 23:
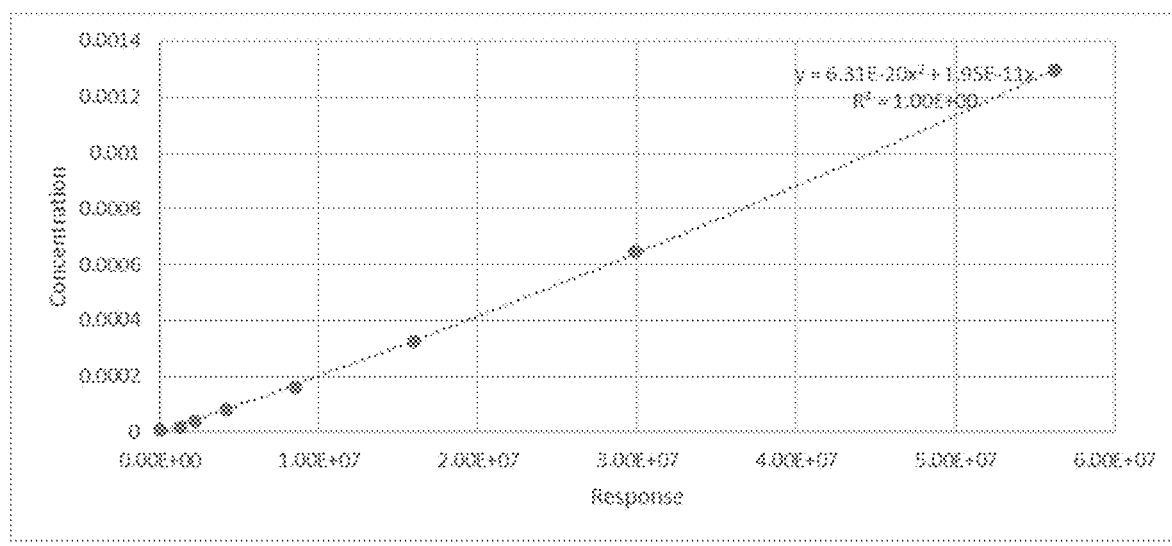
FIG. 23 sets forth an LCMS calibration curve for jasmonic acid methyl ester.
Figure 24:
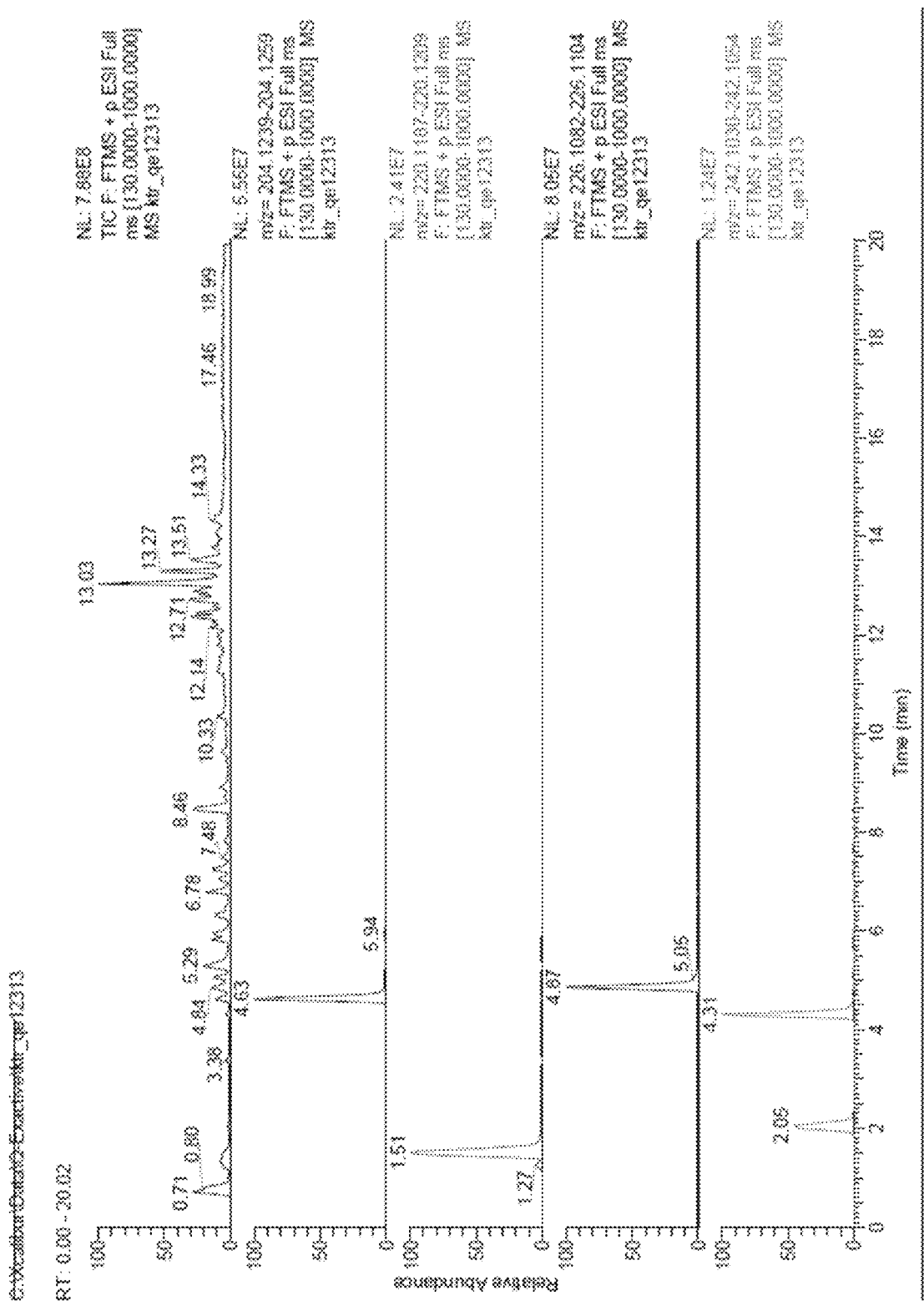
FIG. 24 sets forth an LCMS trace for a mixed standards sample showing molecular ion traces for N6-isopentenyladenine (iP; 4.63), cis-zeatin (cZ; 1.51), N6-benzyladenine (BA; 4.87), para-topolin (pT; 2.05), and ortho-topolin (oT; 4.31).
Figure 25:
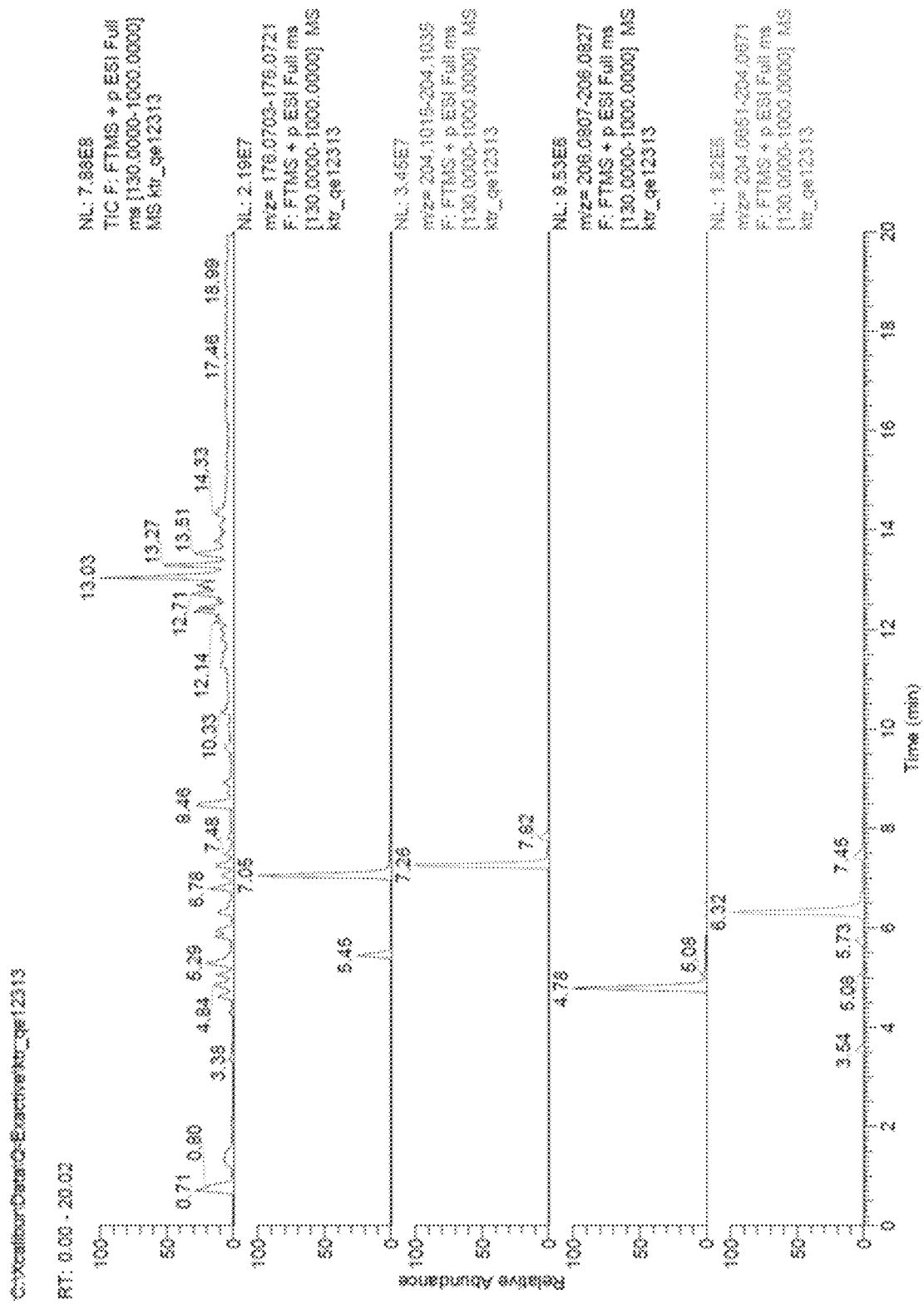
FIG. 25 sets forth an LCMS trace for the mixed standards sample showing molecular ion traces for indole-3-acetic acid (IAA; 5.45), indole-3-carboxylic acid methyl ester (I3CAMe; 7.05), indole-3-butyric acid (IBA; 7.26), DL-indole-3-lactic acid (ILA; 4.78), and indole-3-glyoxylic acid methyl ester (IGAMe; 6.32).
Figure 26:
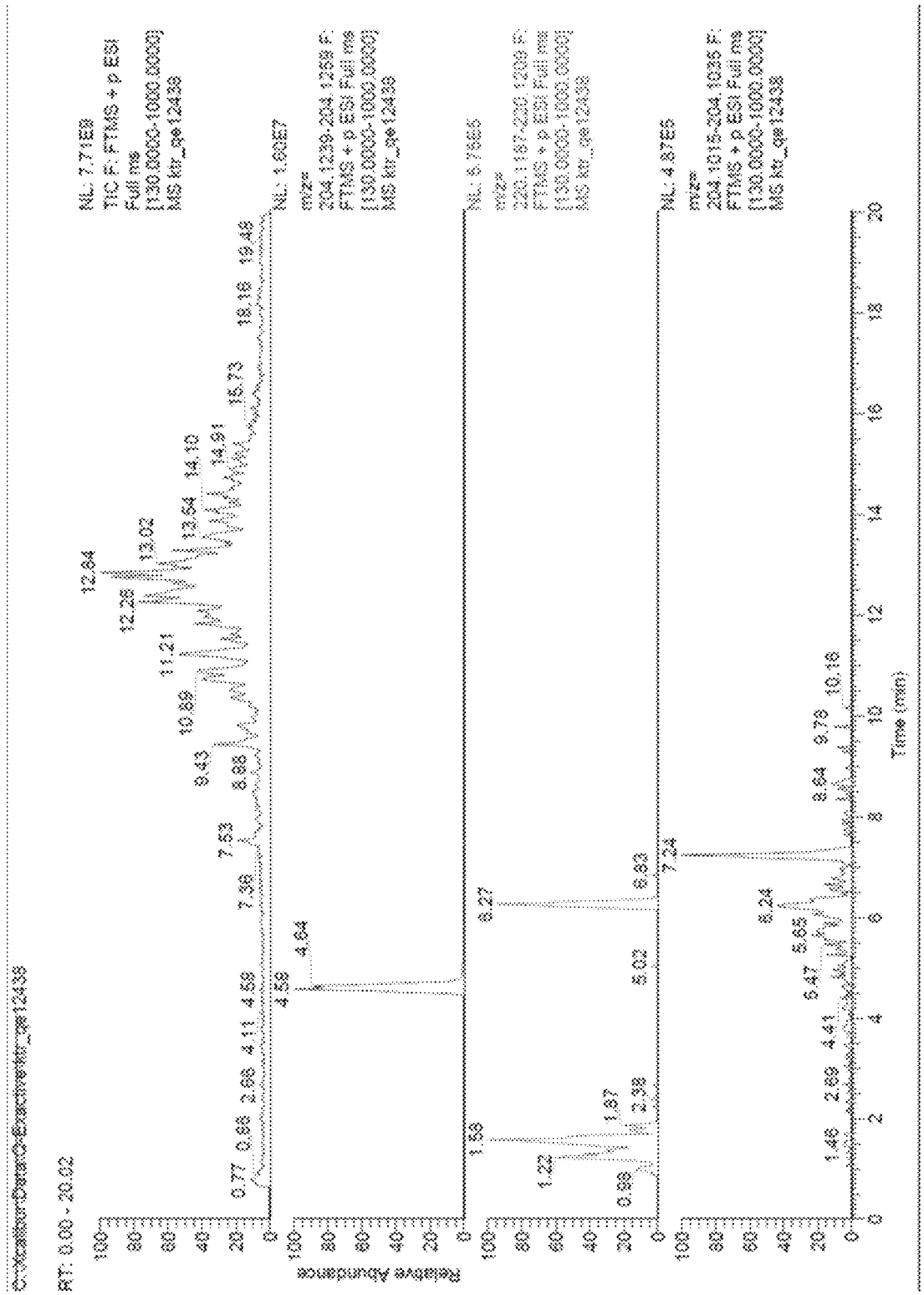
FIG. 26 sets forth an LCMS trace for fraction 3 of Composition 2 showing molecular ion traces for N6-isopentenyladenine (iP; 4.58), cis-zeatin (cZ; 1.58), and indole-3-butyric acid (IBA; 7.24).
Figure 27:
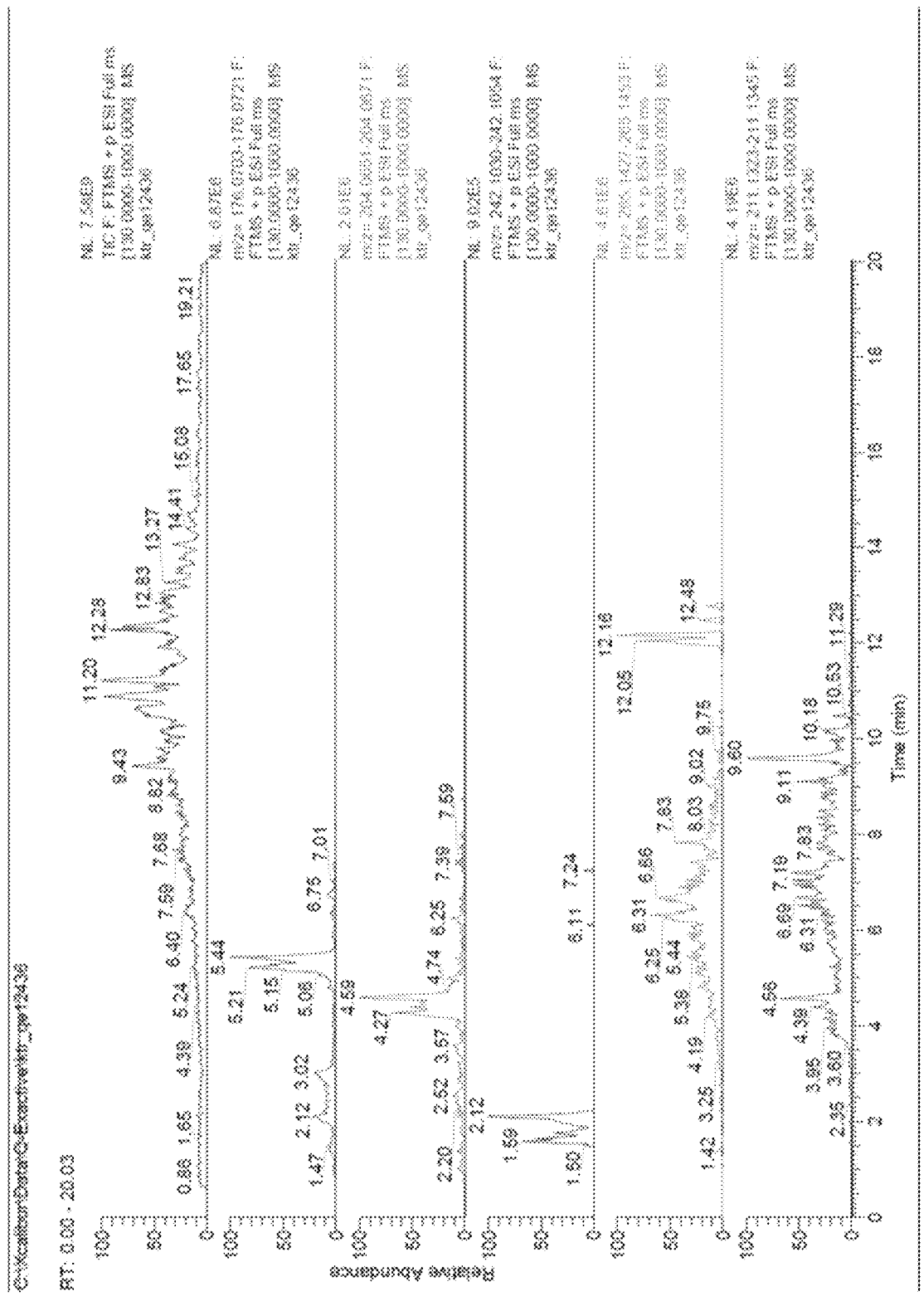
FIG. 27 sets forth an LCMS trace for fraction 5 of the Composition 2 showing molecular ion traces for indole-3-acetic acid (IAA; 5.44), indole-3-glyoxylic acid methyl ester (IGAMe; 6.30), para-topolin (pT; 2.12), (+)-cis,trans-abscisic acid (ABA; 6.79) and (−)-jasmonic acid (JA; 7.49).
Figure 28:
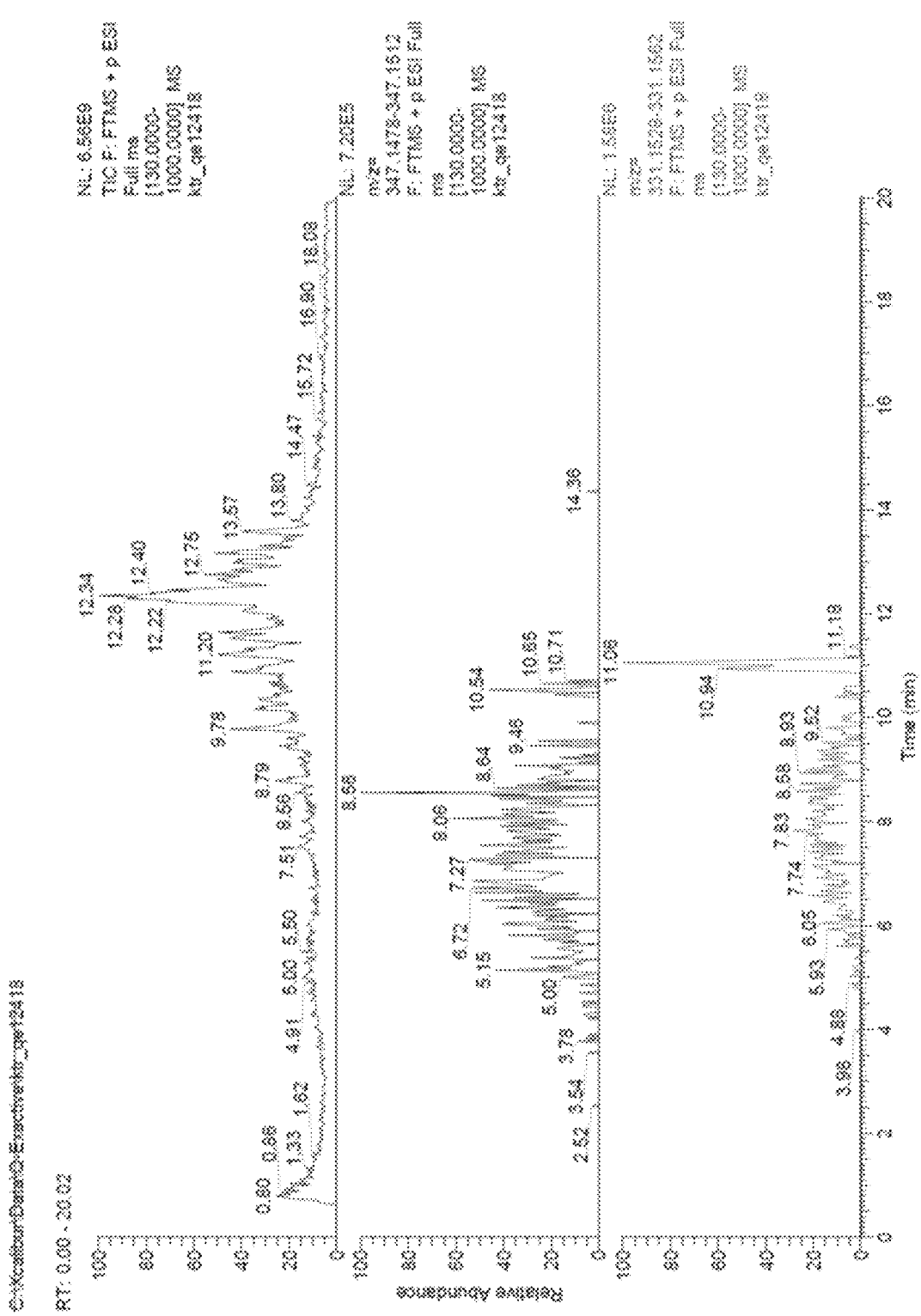
FIG. 28 sets forth an LCMS trace for fraction 6 of Composition 1 showing molecular ion traces for GA3 (5.06) and GA7 (8.45).

The two values FM (fraction of M) and FG (fraction of G) can be calculated from the following:

$$F_G = IA/(IB+IC)$$

$$F_M = 1-FG$$

$$M/G = (1-F_G)/F_G$$

where IA is the integral of the signal for H1-G, IB is the combined integrals for H5-GGM, H5-MGM, H1-MG and H1-MM and IC is the signal for H5-GG (FIG. 2). This gives a M/G ratio of 1.47 for the alginate from the seaweed used to produce the compositions. It can be seen from Table 5 that this is towards the higher end of observed M/G ratios and may therefore be expected to produce a relatively low stiffness gel.

The percentage of blocks can be calculated from the following equations:

$$F_{GG} = IC/(IB+IC)$$

$$F_{MG} = F_{GM} = F_G - F_{GG}$$

$$F_{MM} = F_M - F_{MC}$$

This gives a composition of 45% of the poly M block, 19% of the poly G block and 36% of the copolymeric MG block for the current seaweed.

Figure 32:
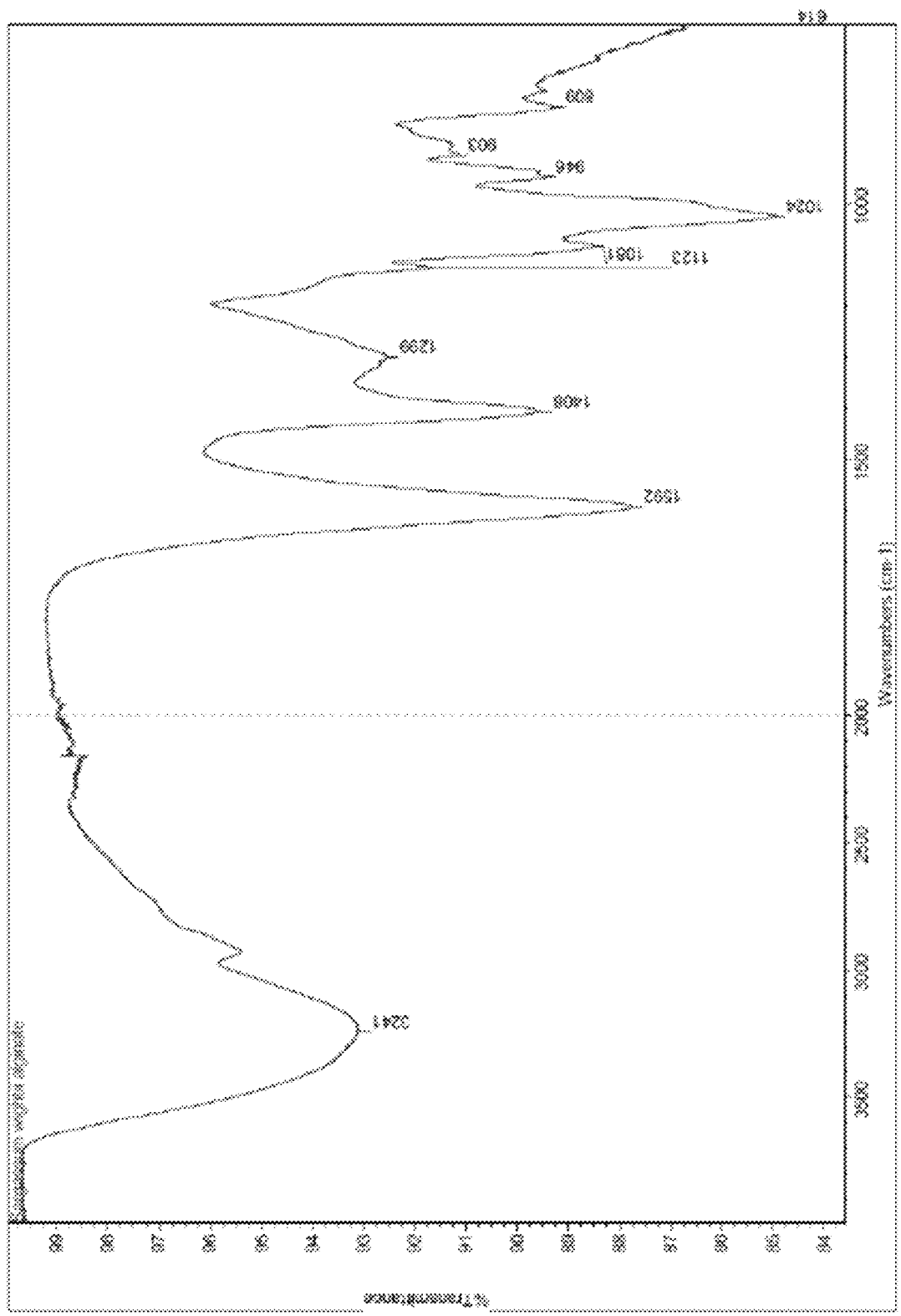
FIG. 32 sets forth an FTIR spectrum of *S. wightii* alginate.

The fourier transform infrared spectrum (FTIR) set forth in FIG. 32 can also be used to estimate the M/G ratio using the peaks at 903 cm$^{-1}$ and 809 cm$^{-1}$, but it doesn't appear to be as accurate and is complicated by the complexity of the peak at 903 cm$^{-1}$ in this sample, so has not been used. The broad band at 3241 cm$^{-1}$ is due to hydrogen-bonded O-H stretching vibrations. There are 8 characteristic bands in the 2000-600 cm$^{-1}$ spectrum of alginates (El Atouni et al. and references therein). The peak at 1592 is due to stretching of the O—C—O in the carboxylate moiety, the lack of any peak at 1720 cm$^{-1}$ indicating essentially complete conversion of the alginic acid into alginate. The band at 1406 cm$^{-1}$ may be due to the C—OH bending vibration, with some contribution from the O—C—O vibration.

The lack of a broad band around 1220-1260 cm$^{-1}$ indicates the absence of contaminating fucoidan. The weaker band at 1081 cm$^{-1}$ and the strong band at 1025 cm-1 arise from C—O and C—C stretching vibrations in the pyranose ring. The band at 945 cm$^{-1}$ has been assigned to C—O stretching in uronic acid. There is normally a peak around 879 cm$^{-1}$ assigned to the Cl—H deformation in β-D-mannuronic acid units but this is obscured in this sample.

Fucoidan

Fucoidan was extracted with dilute acid and precipitated with ethanol. Composition 2 contained much less fucoidan at 17.93 mg or 0.179 mg/mL than Composition 1, which contained 194.26 mg or 1.94 mg/mL of fucoidan. These correspond to 2.5 mg/g or 0.25% for Composition 2 and 27 mg/g or 2.7% for Composition 1 measured relative to the seaweed used to prepare the compositions. The seaweed itself used for production of these compostions, based on the approximate dry weight figure, contained 1.496 g or 6.2% fucoidan by weight. As such, Composition 1 was found to contain almost half the extractable fucoidan, with substantially less in Composition 2.

Fucoidans are complex materials, and a full structural determination has not been performed here. However, certain structural insights can be obtained from the literature in view of some preliminary analysis that has been conducted for this example.

Notably, some structural studies have been conducted on fucoidan from *Sargassum wightii* as was used to produce the compositions described here. Variation has been observed, depending on the species, pH of extraction and the size fraction of the fucoidan. Eluvakkal et al. (2014) found fucose, glucose, galactose and mannose in *S. wightii* fucoidan, with galactose being most abundant. They also found that fucose varied from 15-21% of the total sugars and sulphate varied from 16-38% of the fucoidan by weight for different fractions from the same *Sargassum* sample. Kumar et al. (2015) reported a concentration of 53% of fucose and 36% of sulphate. Zhong et al. (2015) found fucose, rhamnose, xylose, mannose, glucose and galactose in *S. wightii* fucoidan.

Figure 33:
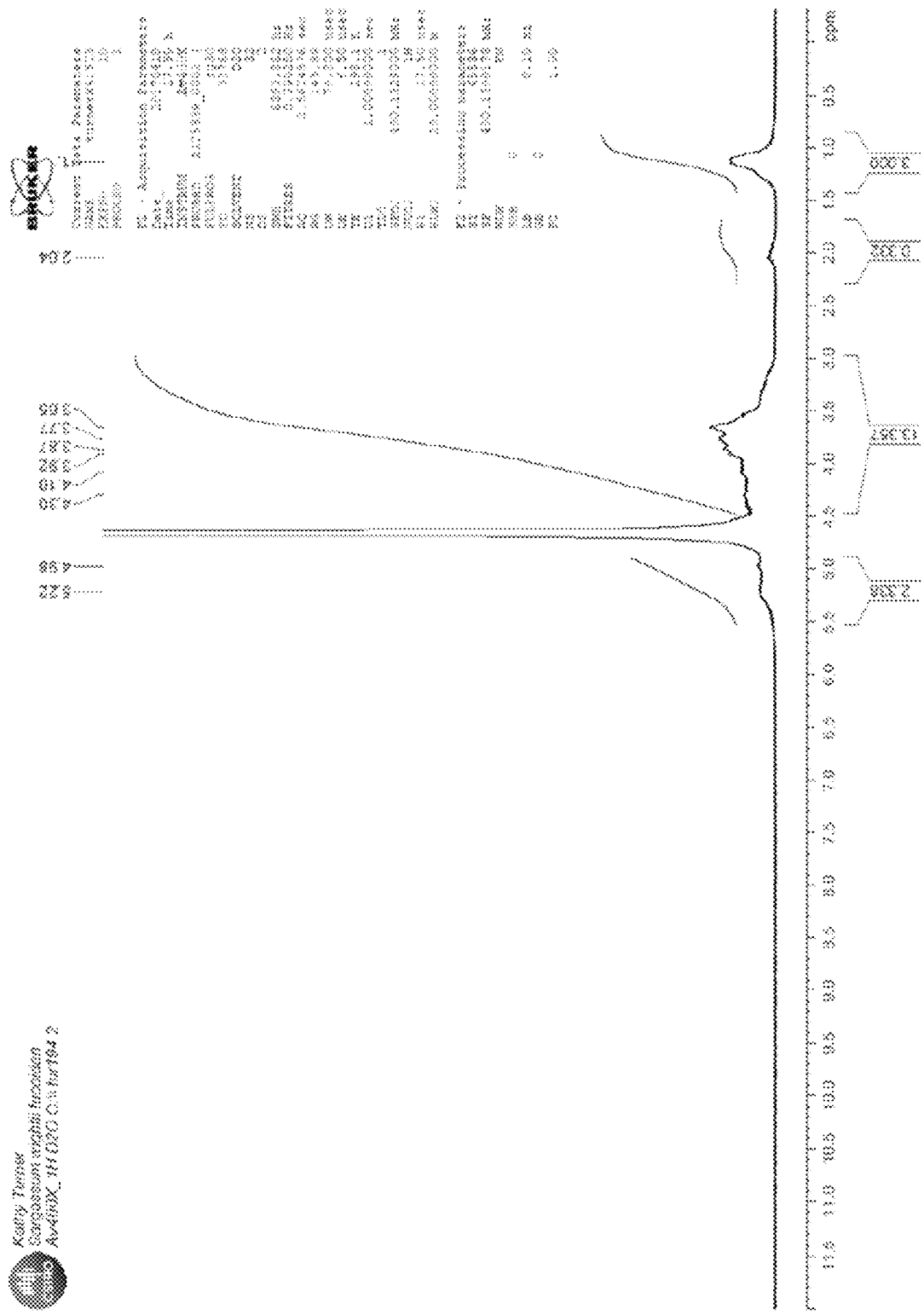
FIG. 33 sets forth $^1$H NMR spectrum of *S. wightii* fucoidan.

$^1$H NMR spectroscopy enables investigation of the hydrogen atoms on a molecule. The $^1$H NMR spectrum for the fucoidan obtained here (FIG. 33) is broadly similar that previously described for *S. wightii* fucoidan by Kumar et al, however certain key difference have also been observed. $^1$H NMR is quantitative, so the integrals for each peak correspond to the number of hydrogens responsible for them. Note that the large peak in the spectrum corresponds to water so is not relevant.

Figure 34:
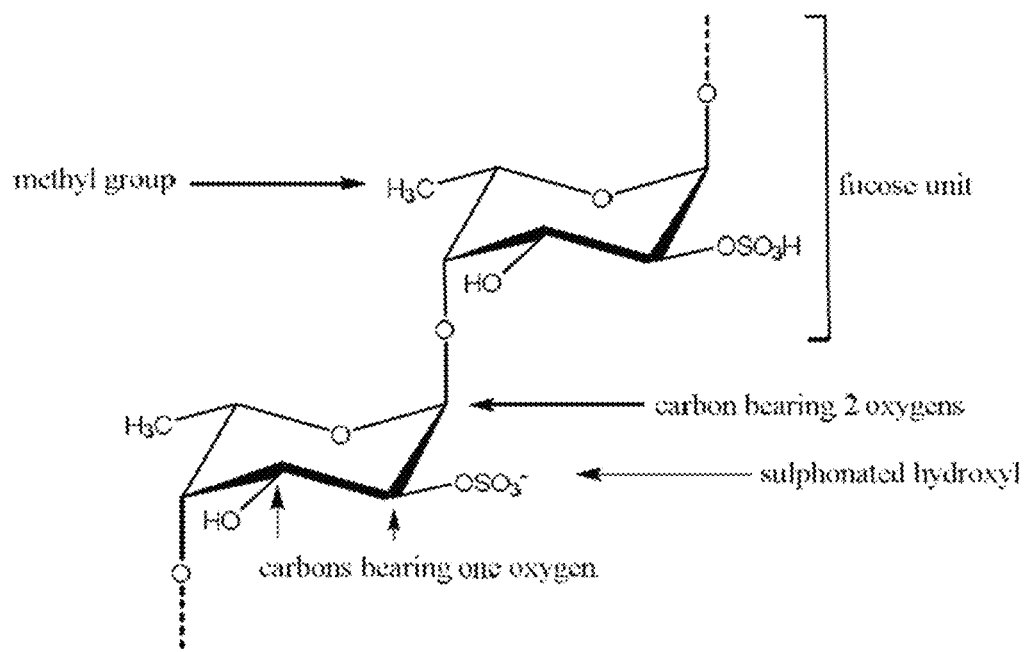
FIG. 34 sets forth an example of a monsulphonated fucose subunit in a fucoidan.

The signals at around 1.1 ppm can be attributed to the hydrogens of the methyl group on the 2-position of the fucose unit (see FIG. 34). The signals between 3.0 and 4.5 are attributable to the hydrogens on the carbons of all the sugar rings which carry a single oxygen and the signals between 4.9 and 5.5 are attributable to the hydrogens on the carbons bearing two oxygens. The signals at 2.0 are probably indicative of acetylation, which is notably much lower in the current samples than that reported by Kumar et al.

Another significant difference between the spectrum for the current sample and that reported by Kumar et al. is the integration between the methyl groups at 1.1 and the hydrogens on singly oxygenated carbons at 3.0-4.5 ppm. If the fucoidan were entirely composed of the type of structural unit shown in FIG. 3, then the ratio of the signals at 1.1 to those at 3.0-4.5 to those at 4.9-5.5 should be 3:4.

In the reported sample of Kumar et al., that ratio is 3:5.9. In the current sample it is 3:13.4. This indicates that both samples contain methoxy groups, and sugars which do not bear a methyl group, but the current sample contains significantly more. It may be expected then that the fucose and sulphate content is probably lower. Eluvakkal et al. report that their *S. wightii* fucoidan is dominated by galactose, contains xylose and some acetylation is present. Those researchers reported sharp signals at 3.85 and 3.65 in the 1H NMR spectrum attributable to the methoxy group of 2-O-methyl-(1→4)-linked-3,6-anhydrogalactose and 6-O-methyl-(1→3)-linked galactose residues. The peaks at 3.87 and 3.65 in the Seychelles fucoidan may correspond to the same components.

Figure 35:
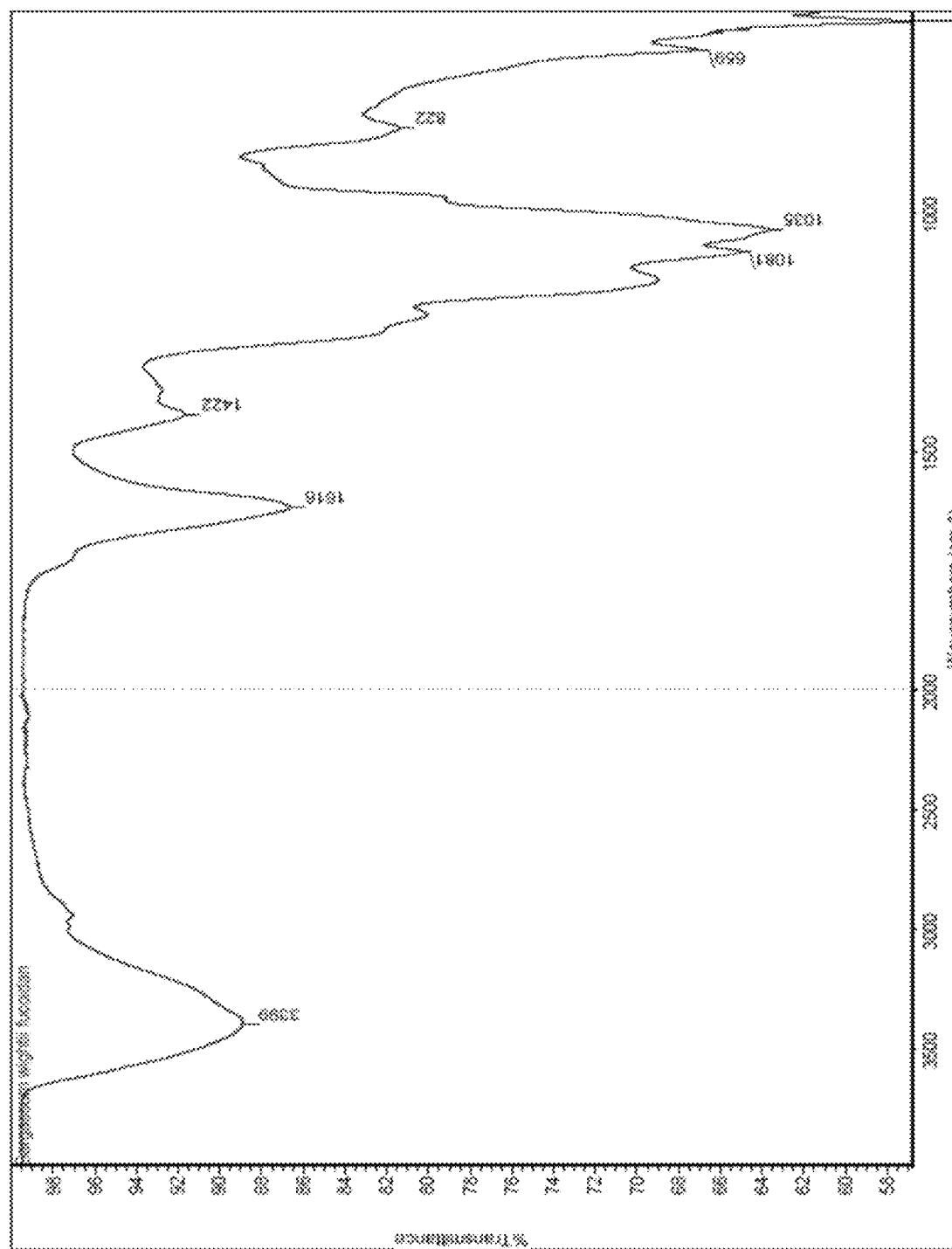
FIG. 35 sets forth an FTIR spectrum of *S. wightii* fucoidan.
Figure 36:
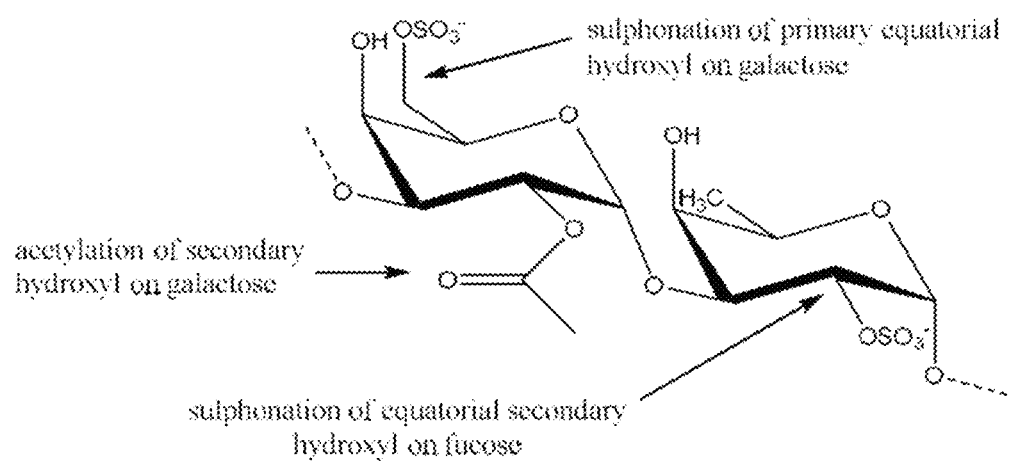
FIG. 36 sets forth possible structural components of *S. wightii* fucoidan.

Infrared spectroscopy has also been used for characterisation of fucoidans from the current samples. The FTIR spectrum is shown in FIG. 35. Again this has some key differences to that reported by Kumar et al.

The band at 3399 cm$^{-1}$ corresponds to O—H stretching. The bands between 1200 and 970 cm$^{-1}$ correspond to C—C, C—O and C—O—C stretching. Strong bands in this region are characteristic of polysaccharides. The band at 1616 cm$^{-1}$ corresponds to C=O stretching and indicates some acetylation of sugars. This is substantially lower in the current sample than the ones reported by Kumar and Elukkaval. This is consistent with the smaller peak for the acetyl methyls in the NMR.

The peak around 1250 attributed to O=S=O stretching is characteristic of sulphated polysaccharides. The band at 822 cm$^{-1}$ is due to C—O—S bending. A signal closer to 832 cm$^{-1}$, indicates that the sulphate is in an equatorial position on a secondary ring hydroxyl. The material reported by Kumar et al has this signal at 838 cm$^{-1}$, indicative of sulphonation at the axial C-4 position. The Seychelles sample signal at 822 cm$^{-1}$ is however indicative of sulphonation of an equatorial primary hydroxyl group attached to a pyranose ring (Lloyd and Dodgson 1961). The pyranose form of fucose does not have a primary hydroxyl group, so this signal must arise from other sugars in the polysaccharide which are sulphonated. It is somewhat broad, so there are probably also some sulphonated fucose ring hydroxyl groups. Examples of the sort of sugars the fucoidan may contain based on these results are shown in FIG. 35. The two sugars shown are fucose and galactose. These are shown with sulphonation of both sugars and acetylation of the galactose, whereas in the fucoidan, only some will sulphonated and acetylated.

Discussion

Both Composition 1 and Composition 2 were found to contain alginate and fucoidan, although extraction of both from the seaweed used to produce the compositions appears incomplete. Composition 1 and Composition 2 were found to contain similar amounts of alginate, however Composition 1 was found to contain much more fucoidan. Given that alginates are soil conditioners and their breakdown products, oligo-alginates may have growth promoting properties, the alginate in both Composition 1 and Composition 2 may be advantageous in the context of use of the compositions for stimulating plant growth.

As extraction of the fucoidan and alginate in Composition 1 and Composition 2 is incomplete, this provides the opportunity of isolating more from the seaweed residue after extraction used to produce these compositions. Either the remaining fucoidan or both the fucoidan and the alginate could be obtained, for example to produce further compositions comprising or consisting of, for example, fucoidan, alginate, a soil conditioner comprising the residue without the fucoidan and the residue with fucoidan.

It is notable that, if the fucoidan were removed to produce a composition comprising alginate to be used as a soil conditions, the effect of the addition of any acid on the properties of the composition as a soil conditioner would need to be considered. By way of elaboration, the protocol described here uses hydrochloric acid to precipitate fucoidan, but use of phosphoric acid followed by neutralisation may be more appropriate if a composition from which fucoidan was removed was to be used as a soil conditioner.

Detailed Materials and Methods

General Considerations

All water used was Milli-Q water supplied by a Milli-Q water purifier (Millipore). Centrifugation was conducted at 4696 g for 20 min unless stated otherwise.

Determination of Fucoidan and Alginate in Composition 1 and Composition 2

(A) 100 mL of Composition 1 or Composition 2 was concentrated under reduced pressure at 20° C. to a brown gum (2.349 g for Composition 1; 535 mg for Composition 2). This gum was soaked with 70:30 ethanol:water overnight then centrifuged at 3000 g for 20 min. The supernatant was decanted off and the residue stirred with 80:20 ethanol:water for 3 days then centrifuged. The supernatant was again decanted off and the residue stirred with further 80:20 ethanol:water (120 mL) and heated to 70° C. then maintained at this temperature for 4 h. This was then centrifuged and the supernatant decanted off again.

(B) The residue from A was suspended in 0.1M hydrochloric acid then stirred and heated to 90° C. then maintained at 87-95° C. for 25 min. This was then cooled to room temperature then centrifuged and the supernatant decanted off again. The solid was washed with water (1 mL), centrifuged again and the supernatant decanted off again. The supernatants (181 mL total) were combined.

(C) Calcium chloride dihydrate (4.77 g, 3.24 mmol) was added to the combined supernatants from B to give a 2% solution and the mixture stood at 6° C. overnight. This was then centrifuged, and the supernatant decanted off. Water (1 mL) was added to the solid and the resulting suspension centrifuged again and the supernatant decanted off. The residual solid was dried at 3 mbar over phosphorus pentoxide to give calcium alginate as a brown solid (5.53 mg for Composition 1; 0.59 mg for Composition 2).

(D) The supernatant from C was diluted with ethanol (364 mL, 2 volume equivalents) and stood overnight at 6° C., then centrifuged again and the supernatant decanted off. The residual solid was washed with 1:1 ethanol:water (10 mL), centrifuged and the supernatant decanted off. The solid was then washed with ethanol (10 mL), centrifuged and the supernatant decanted off. The solid was then dried under vacuum over phosphorus pentoxide to give fucoidan (194.26 mg Composition 1; 17.93 mg Composition 2) as a tan solid.

(E) The solid from B was suspended in 0.1M sodium carbonate solution (180 mL) then stirred and heated to 100° C. It was maintained at this temperature for 10 min then cooled to room temperature and centrifuged. The supernatant was decanted off and the solid washed with water (50 mL). The suspension was centrifuged and the supernatant removed. The combined supernatants were diluted 1:1 with ethanol, shaken vigorously then centrifuged. The precipitated solid was washed with 1:1 ethanol:water (20 mL), centrifuged then the supernatant decanted off. The solid was then the solid was washed with ethanol (20 mL), centrifuged then the supernatant decanted off. The solid was dried at room temperature under vacuum (3 mbar) for 3 days to give sodium alginate (1.017 g for Composition 1; 940 mg for Composition 2) as a brown solid.

Determination of Fucoidan and Alginate in Seaweed after Extraction with Ethanol/Water (A) Air dried *Sargassium wightii* supplied by Seaweed Seychelles was dried over phosphorus pentoxide for 3 days at 4-10 mbar to give 37.418 g of solid. This was ground with a mortar and pestle, then sieved through a 0.433 mm sieve. The sieved material (28.574 g) and the material too large to go through the sieve (8.773 g) were recombined.

(B) A portion (25.003 g) of the solid material from part A was stirred with 80:20 ethanol:water for 24 h then filtered through a porosity 3 sintered glass filter. The solid material was resuspended in 80% ethanol (300 mL) and stirred at room temperature (6-22° C.) for 3 days. It was then filtered again. The solid was resuspended in 80% ethanol (300 mL) then heated to 70° C. for 4 h. The suspension was filtered hot, the solid washed with 50 mL of ethanol and dried under vacuum overnight at 40 mbar, then 3 h at 3 mbar to give a brown solid (20.680 g).

(C) The remainder of the material from part A (12.428 g) was dried under vacuum over phosphorus pentoxide at 3-4 mbar for 4 days to give a brown solid (11.929 g).

(D) The solid material from B was suspended in 0.1M hydrochloric acid (450 mL), stirred and heated to 90° C. then maintained at 90-92° C. for 25 min. It was then cooled to room temperature and centrifuged. The supernatant was decanted off and the residue washed with water (150 mL) and centrifuged again. The supernatant was combined with the previous supernatant.

(E) Calcium chloride dihydrate (14.57 g, 99 mmol) was then added to the supernatant from D (550 mL) to give a 2% solution of calcium chloride. The mixture was stood overnight at 6° C., then centrifuged again at 4696 g. The supernatant was decanted off and the combined residues washed with 2% calcium chloride solution (10 mL). This was centrifuged again and the supernatant decanted off then combined with the previous supernatant. The combined residues were dried for 3 days under vacuum at 3-4 mbar over phosphorus pentoxide to give calcium alginate (81.03 mg) as a tan solid.

(F) The solid material (residue) from D was suspended in 0.1M sodium carbonate solution (450 mL) then stirred and heated to 100° C. The temperature was maintained at 100° C. for 10 min then cooled to room temperature, centrifuged and the supernatant decanted off. The solid material was washed with water (120 mL), centrifuged and the supernatant decanted off. This process was repeated once more. All the supernatants were combined and diluted 1:1 with ethanol, shaken vigorously, then centrifuged. The precipitated alginate was washed with 1:1 ethanol:water (100 mL) then ethanol (100 mL) and dried under vacuum (3-4 mbar) at room temperature over phosphorus pentoxide for 4 days to give sodium alginate (6.633 g) as a brown solid.

(G) The combined supernatants from E were diluted 2:1 with ethanol then stood overnight at 6° C. The resulting suspension was centrifuged then the supernatant decanted off. The solid was washed with 2:1 ethanol:water (30 mL), centrifuged and the supernatant decanted off. It was then washed with ethanol (30 mL), centrifuged and the supernatant decanted off. The residual solid was then dried for 3 days under vacuum (3-4 mbar) at room temperature over phosphorus pentoxide to give fucoidan (1.496 g) as a tan powder.

FTIR Spectroscopy

Fourier transform infrared spectroscopy was conducted with the sample in solid form on a Thermo Nicolet 6700 Fourier transform infrared spectrophotometer.

NMR Spectroscopy

NMR Spectroscopy was conducted on a Bruker Biospin Av400 spectrometer at 400 MHz. Chemical shifts were measured relative to the resonance of $D_2O$ (heavy water). The fucoidan sample was stirred 3 times with $D_2O$ then concentrated under reduced pressure to remove exchangeable protons. The samples were dissolved in deuterium oxide for NMR analysis.

Example 4. Additional Processing Steps

Salt water washing and/or pressure cooking steps can be desirable for producing seaweed extracts as described herein. Exemplary such steps that have been performed are set out as follows.

Salt Water Washing

Salt water washing is performed using 1000 L washing tanks, containing salt water pumped directly from the sea. Seaweed is soaked in sea water using a series of four (4) 1000 L tanks, with the seaweed being transferred from tank to tank. The total duration of soaking in the tanks is about 12 hours.

Pressure Cooking

An industrial pressure cooking tank is filled approximately half way, and water at a temperature of 80° C. is then pumped into the tank to cover the seaweed. Subsequently, additional seaweed and water at 80° C. is added until the tank is full. The seaweed is left to soak for 1 to 6 hours before pressure cooking starts.

Pressure cooking starts by activating heating coils in the tank. Once the temperature reaches about 121° C. the heating is stopped and the seaweed is cooked on its own with the use of the pressure inside the vessel. The inside pressure is typically elevated by about 0.5 to 1.7 bar (i.e. the total pressure around 1.5 to 2.7 atm). The duration of cooking at elevated pressure is about 2 hours.

For red seaweed, it is considered particularly desirable to use substantially pure water, typically distilled water, for pressure cooking.

Example 5. Assessment of Application of Compositions on Lettuce Yield

Introduction

An experimental trial was conducted to evaluate the yield response of lettuce to different rates of application of Composition 2 as described in Example 1. The lettuce variety used was Mindelo. The experiment was conducted between the months of June to August at the Anse Boileau Crop Research and Development station (Seychelles) in sandy soils and under open field conditions.

A total of seven treatments were evaluated. The different treatments represented five different rates of dilution of seaweed extract; a conventional fertiliser (positive control); and an untreated plot (negative control) as set out in Table 6. The treatments were replicated four times in a randomised block design layout in the field. The lettuce seeds were sown in the nursery in large wooden boxes on the $27^{th}$ of June. Two weeks after germination the seedlings were transplanted into poly-pots. The first treatment application was carried out on the $26^{th}$ of July in the nursery as per the treatment schedule.

Field preparation began on the $27^{th}$ of July. Prior to transplanting into the open field, the experimental plot, measuring 10.8 m×30.0 m (324.0 m$^2$) was cleared of all visible vegetation and plant debris. The planting area was then ploughed to a depth of 30 cm before demarcation of the treatment plots and installation of the micro-sprinklers. The experimental plot was divided and labeled into 28 treatment plots. Each treatment plot measured 5.5 m×1.2 m (6.6 m$^2$) and consisted of 3 rows of plants with a spacing of 50 cm between plants and 40 cm between rows with a total of 33 plants. Holes were dug about 15 cm deep in each treatment plot to which well-decomposed poultry manure at a rate of 15 T/ha (equivalent to 300 g/hole) were added and then covered with a thin layer of soil before being irrigated continuously for three days prior to transplanting in the same holes. The sample plot size measured 2.0 m×1.0 m (2.0 m$^2$) equivalent to 10 plants.

The lettuce seedlings were transplanted to the different treatment plots in the open field on the $31^{st}$ of July according to the experimental trial layout. The first treatment applications in the field were carried out on the $4^{th}$ of August as per the treatment schedule.

Cultural practices such as earthing-up and weeding were carried out throughout the experiment as the need arose. The lettuce plants were harvested on the $31^{st}$ of August. At the time of harvest the lettuce plants from the different sample plots of each treatment were carefully uprooted. The fresh weights of the plants along with the roots were recorded. The roots were then cut off and weighed separately in order to obtain the root weight. The weight of the above ground parts where then determined.

Results

Figure 37:
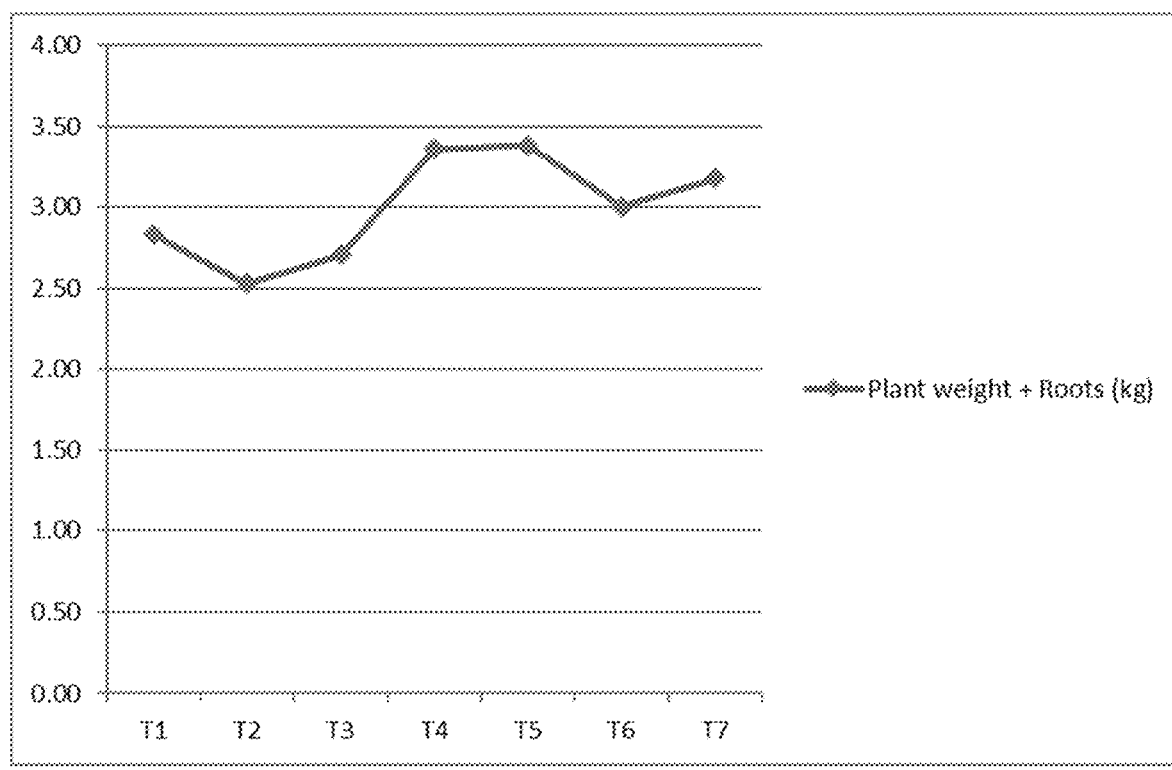
FIG. 37 sets forth lettuce weight (including roots) grown under application of various dilutions of seaweed extract compositions (T1-T5), a conventional fertiliser (T6), and a negative control (T7).

The application of the seaweed extract at the rate of 200 ml/L and 250 ml/L had the greatest effect on lettuce yield compared to the control and the other treatments as shown in Table 7 and FIG. 37. The plants+roots weight recorded for Treatment 4 (200 ml/L) and Treatment 5 (250 ml/L) were 12% and 12.7% higher compared to the control. However the difference between these two treatments and that of Treatment 7 (negative control) was only 5.7% and 6.3%. This result suggests that there might be a residual and/or interacting effect influencing the yield of the lettuce plants based on previous fertiliser applications or from the basal poultry manure applied.

No major differences in root weights between the different treatments were observed as shown in Table 7.

Figure 38:
FIG. 38 sets forth an exemplary photograph of lettuce grown under application of a seaweed extraction composition.

An exemplary photograph of lettuce grown under application of seaweed extract is provided in FIG. 38.

Conclusions

The results obtained demonstrate that the application of seaweed extract dilution rates of 200 ml/L and 250 ml/L had a superior effect on lettuce yield as compared to conventional fertiliser application, and no fertiliser application. It is noted, however, that there appeared to be some residual and/or interacting effect in the experiment, with the untreated control showing higher yield than the seaweed extract application at 50, 100, and 150 ml/L, and application of the conventional fertiliser. Soil analysis to better understand nutrient content in the untreated plots could provide a better understanding of these effects.

Figure 39:
FIG. 39 sets forth an exemplary photograph of corn grown under application of a seaweed extraction composition.
Figure 40:
FIG. 40 sets forth an exemplary photograph of banana grown under application of a seaweed extraction composition.
Figure 41:
FIG. 41 sets forth an exemplary photograph of pumpkin grown under application of a seaweed extraction composition.

Example 6. Preliminary Assessment of Application of Seaweed Extract Compositions on Yield of Other Crops The application of compositions as described herein to stimulation of growth of a range of other plants has been qualitatively assessed. In general, positive effects of the application of the compositions, particularly at dilution rates of less than about 1 in 6, have been observed. Exemplary photographs of corn (FIG. 39), banana (FIG. 40), and pumpkin (FIG. 41) grown under application of compositions as described herein are provided.

Throughout the specification, the aim has been to describe preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

REFERENCES

Abd El-Rehim H A Characterization and possible agricultural application of polyacrylamide/sodium alginate crosslinked hydrogels prepared by ionizing radiation. Journal of Applied Polymer Science 101(6) 3572-3580. DOI: 10.1002/app.22487.

Blunden G and Gordon S M (1986) Betaines and their sulphino analogues in marine algae. Progress in Phycological Research 4, 39-79.

Chen H, Cong, Q, Du Z, Liao W, Zhang L, Yao Y and Ding K (2016) Sulfated fucoidan FP08S2 inhibits lung cancer cell growth in vivo by disrupting angiogenesis via targeting VEGFR2/VEGF and blocking VEGFR2/Erk/VEGF signalling. Cancer Letters 382(1), 44-5.

Dobrev Pl, Kaminek M (2002) Fast and efficient separation of cytokinins from auxin and abscisic acid and their purification using mixed-mode solid phase extraction. Journal of Chromatography A 950, 21-29.

El Atouni S, Bentiss F, Reani, A, Zrid R, Belattmania Z, Pereira L, Mortadi A, Cherkaoui O and Sabour B (2016), The invasive brown seaweed *Sargassum muticum* as new resource for alginate in Morocco: Spectroscopic and rheological characterization. Phycological Research 64, 185-93.

Eluvakkal T, Sivakumar S, Arunkumar K (2010) Fucoidan in some Indian brown seaweeds found along the coast Gulf of Mannar. International Journal of Botany 6(2), 176-181.

Eluvakkal T, Shanthi N, Murugan M, Arunkumar K (2014) Extraction of antibacterial substances, galactofucoidan and alginate successively from the Gulf of Mannar brown seaweed *Sargassum wightii* Greville ex J. Agardh. Indian Journal of Natural Products and Resources 5(3), 249-257.

Florez-Fernandez N, Lopez-Garcia M, Gonzalez-Munoz M J, Vilarino J M L and Dominguez H (2017) Ultrasound-assisted extraction of fucoidan from *Sargassum muticum*. Journal of Applied Phycology, Ahead of Print.

Gradsalen H, Larsen B, Smidsrød O (1979) A p.m.r. study of the composition and sequence of urinate residues in alginates. Carbohydrate Research 68, 23-31.

Holub J, Hanus J, Hanke D E and Strnad, M (1998) Biological activity of cytokinins derived from ortho- and meta-hydroxybenzyladenine. Plant growth regulation 26, 109-115.

Immanuel G, Sivagnanavelmurugan M, Marudhupandi T, Radhakrishnan S and Palavesam A (2012) The effect of fucoidan from brown seaweed *Sargassum wightii* on WSSV resistance and immune activity in shrimp *Penaeus monodon* (Fab). Fish & shellfish immunology 32(4), 551-64.

Immanuel G, Sivagnanavelmurugan M, Balasubramanian V, Palavesam A (2012a) Sodium alginate from *Sargassum wightii* retards mortalities in *Penaeus monodon* postlarvae challenged with white spot syndrome virus. Diseases of Aquatic Organisms 99(3), 187-196.

Katsumi M and Ishida K (1991) The gibberellin control of cell elongation. In: Takahashi N, Phiney B O, MacMillan J (eds) Gibberellins. Springer-Verlag, New York.

Koepfli J B, Thimann K V and Went, F W (1938) Phytohormones: Structure and physiological activity. I. Journal of Biological Chemistry 122(3), 763-780.

Kumar A, Altabella T, Taylor M A and Tiburcio A F (1997) Recent advances in polyamine research. Trends in Plant Science 2(4), 124-130. DOI: 10.1016/S1360-1385(97)01013-3.

Kumar T V, Lakshmanesenthil S, Geetharamani D, Marudhupandi T, Suja G, Suganya P (2015) Fucoidan—A a-D-glucosidase inhibitor from *Sargassum wightii* with relevance to type 2 diabetes mellitus therapy. International Journal of Biological Macromolecules 72, 1044.

Lakshmana Senthil 5, Vinoth Kumar T, Geetharamani D, Suja G, Yesudas R, Chacko A (2015) Fucoidan—An α-amylase inhibitor from *Sargassum wightii* with relevance to NIDDM International Journal of Biological Macromolecules 81, 644-647.

Letham D S, Palni L M S, Tao G-Q, Gollnw, B I and Bates C M (1983) Regulators of cell division in plant tissues XXIX. The Activities of cytokinin glucosides and alanine conjugates in cytokinin bioassays. Journal of Plant Growth Regulation 2, 103-115.

Lloyd, A G and Dodgson K S (1961) Infrared studies on sulphate esters. II. Monosaccharide sulphates. Biochimica et Biophysica Acta 46, 116-120.

Lim S J, Mustapha W A W, Maskat M Y, Latip J, Badri K H, Hassan O (2016) Chemical properties and toxicology studies of fucoidan extracted from Malaysian *Sargassum binderi*. Food Science and Biotechnology 25(S1), 23-29.

Lim S J, Mustapha W A W, Maskat, M Y Latip J, Badri K H, Hassan O Yamin and Bohari M (2016a) Characterisation of fucoidan extracted from Malaysian *Sargassum binderi*. Food Chemistry 209, 267-273.

Martinsen A, Skjåk-Bræk G and Smidsrød (1989) Alginate as Immobilization Material: I. Correlation between chemical and physical properties of alginate gel beads. Bioengineering and Biotechnology 1987, 33, 79-89.

Marudhupandi T, Kumar T T A (2013) Antibacterial effect of fucoidan from *Sargassum wightii* against the chosen human bacterial pathogens. International Current Pharmaceutical Journal 2(10), 156-158, 3 pp.

Masny A, Basak A and Zurawicz E (2004) Effects of foliar applications of Kelpak S L and Goëmar B M 86® preparations on yield and fruit quality in two strawberry cultivars. Journal of Fruit and Ornamental Plant Research 12, 23-27.

Matsubara 5 (1990) Structure-activity relationships of cytokinins. Critical Reviews in Plant Sciences 9:1, 17-57. DOI: 10.1080/07352689009382281.

Mok M, Martin R C, Dobrev P I, Vankova, R, Ho, P S, Yonekura-Sakakibara, K, Sakakibara, H and Mok, D W S (2005) Topolins and hydroxylated thidiazuron derivatives are substrates of cytokinin 0-glucosyltransferase with position specificity related to receptor recognition. Plant Physiology 137(3), 1057-1066. DOI:10.1104/pp. 104.057174.

Naeem M, Khan M M A and Moinnuddin (2012), Triacontanol: a potent plant growth regulator in agriculture. Journal of Plant Interactions 7(2), 129-142. DOI:10.1080/17429145.2011.619281.

Osborne D J and McManus M T (2005) Hormones, Signals and Target Cells in Plant Development. Cambridge University Press, Cambridge and references therein.

Papenfus H B, Stirk W A, Finnie J F, Van Staden J (2012) Seasonal variation in the polyamines of *Ecklonia maxima*. Botanica Marina 55(5), 539-546.

Pilet P (1971) Effect of auxins on root protoplasts. Comptes Rendus des Seances de l'Academie des Sciences, Serie D: Sciences Naturelles 273, (23), 2253-6.

Piotrowska A and Bajguz, A (2011) Conjugates of abscisic acid, brassinosteroids, ethylene, gibberellins and jasmonates. Phytochemistry 72(12), 2097-2112. DOI: 10.1016/j.phytochem.2011.08.012.

Quastel J H (1954) Soil Conditioners. Annual Reviews of Plant Physiology 5, 75-92.

Reinert J and Yeoman M M, Plant Cell and Tissue Culture. A Laboratory Manual. Springer-Verlag, Berlin, Heidelberg.

Rinaudo M (2007) Chapter 2.21 Seaweed polysaccharides. In: Kamerling J P (ed) Comprehensive Glycoscience from Chemistry to Systems Biology, Volume 2: Analysis of Glycans; Polysaccharide Functional Properties. Elsevier, Oxford. DOI: 10.1016/B978-044451967-2/00140-9.

Sandberg G (1987) Indole-3-acetic acid and related compounds. In: Rivier L. and Crozier A (eds) Principles and practice of plant hormone analysis. Academic Press, London.

Sinha S, Astani A, Ghosh T, Schnitzler P and Ray B (2010) Polysaccharides from *Sargassum tenerrimum*: Structural features, chemical modification and anti-viral activity. Phytochemistry 71(2-3), 235-242.

Sivagnanavelmurugan M, Karthik Ramnath G, Jude T B, Palavesam A, Immanuel G (2015) Effect of *Sargassum wightii* fucoidan on growth and disease resistance to *Vibrio parahaemolyticus* in *Penaeus monodon* post-larvae. Aquaculture Nutrition 21(6), 960-969.

Somasundaram S N, Shanmugam S, Subramanian B, Jaganathan R (2016) Cytotoxic effect of fucoidan extracted from *Sargassum cinereum* on colon cancer cell line HCT-15. International Journal of Biological Macromolecules 91, 1215-1223.

Stec N, Banasiak J and Jasinski M (2016) Abscisic acid—an overlooked player in plant-microbe symbioses formation?. Acta Biochimica Polonica 63(1), 53-58.

Stirk W A and Van Staden J (1997) Comparison of cytokinin- and auxin-like activity in some commercially used seaweed extracts. Journal of Applied Phycology 8, 503-508.

Stirk W A, Novák O, Strnad M and van Staden, J (2003) Cytokinins in macroalgae. Plant growth regulation 41(1), 13-24.

Stirk W A, Arthur G D, Lourens, A F, Novák O, Strnad M and van Staden J (2004), Changes in cytokinin and auxin concentrations in seaweed concentrates when stored at elevated temperature. Journal of Applied Phycology 16(31-39), 2004.

Stirk W A, Tarkowská D, Turečová V, Strnad M and van Staden J (2014) Abscisic acid, gibberellins and brassinosteroids in Kelpak®, a commercial seaweed extract made from *Ecklonia maxima*. Journal of Applied Phycology 26, 561-567.

Su Y-H, Liu Y-B and Zhang X-S (2011) Auxin-cytokinin interaction regulates meristem development. Molecular Plant 4(4), 616-625.

Sun H, Tao J, Gu P, Xu G and Zhang Y (2016) The role of strigolactones in root development. Plant Signaling & Behavior Ahead of Print. DOI:10.1080/15592324.2015.1110662

Tay S A B, MacLeod J K, Palni L M S and Letham D S (1985) Detection of cytokinins in a seaweed extract. Phytochemistry 24(11), 1985.

Tay S A B, Palni L M S and MacLeod J K (1987) Identification of cytokinin glucosides in a seaweed extract. Journal of Plant Growth Regulation 5, 133-138.

Teale W D, Papanov I A and Palme K (2006) Auxin in action: signalling, transport and the control of plant growth and development. Nature Reviews: Molecular Cell Biology 7, 847-859. DOI:10.1038/nrm2020.

Ueda K, Kuroda R, Kimura T, Akao T, Shinohara N, Ushirokawa T, Fukagawa A, Akimoto T (2008) A quantitative analysis of polysaccharides of brown algae akamoku collected off the Oshima Island (Fukuoka Prefecture). (Second report) Kenkyu Hokoku-Fukuoka-ken Kogyo Gijutsu Senta 18, 43-46.

Villarreal-Rivera L and Martinez-Lozano S J (2001) Levels of alginic acid, fucoidan and laminaran in some species of the algae Phaeophyta. Phyton 179-181.

Vinoth K T, Suja G, Suganya P, Lakshmanasenthil S, Geetharamani D, Marudhupandi T (2015) Fucoidan—a α-D-glucosidase inhibitor from *Sargassum wightii* with relevance to type 2 diabetes mellitus therapy. International journal of biological macromolecules 72, 1044-7.

Yamaguchi S (2008) Gibberellin metabolism and its regulation. Annual Reviews of Plant Biology 59, 225-51. DOI: 10.1146/annurev.arplant.59.032607.092804.

Yu H, Hou B (2006) Analysis on the bioactivity of cytokinin glucosides in plant. Zhiwu Shenglixue Tongxun 42(5), 897-899.

Yuan W, Liu, Changheng S Y, Li N, Zhang M, Shi Y, Xia X, Qiao R, Hu W, Ju W et al (2016) An extraction method of fucoidan sulfate by utilizing *Sargassum kjellmanianum*. Faming Zhuanli Shenqing (2016), CN 105273104 A 20160127.

Yuan Y and Macquarrie D J (2015) Microwave assisted step-by-step process for the production of fucoidan, alginate sodium, sugars and biochar from *Ascophyllum nodosum* through a biorefinery concept. Bioresource Technology 198, 819.

Yuguchi Y, Tran V T T, Bui L M, Takebe S, Suzuki S, Nakajima N, Kitamura S Thanh T T T (2016) Primary structure, conformation in aqueous solution, and intestinal immunomodulating activity of fucoidan from two brown seaweed species *Sargassum crassifolium* and *Padina australis*. Carbohydrate Polymers 147, 69-78.

Zhong S-Y, Wang W-M, Chen S-H, Cai L (2015) Preparation and chemical composition analysis of different molecular weights of fucoidan from *Sargassum wighti*. Shipin Yu Fajiao Gongye 41(6), 70-75.

TABLE 1

Concentration of growth hormones in seaweed.

| HORMONE | CONCENTRATION IN SEAWEED IMPLIED BY ROOM TEMPERATURE EXTRACT (COMPOSITION 1) (pmol/g) | CONCENTRATION IN SEAWEED IMPLIED BY ROOM TEMPERATURE EXTRACT (COMPOSITION 1) (ng/g) | CONCENTRATION IN SEAWEED IMPLIED BY 90° C. EXTRACT (COMPOSITION 2) (pmol/g) | CONCENTRATION IN SEAWEED IMPLIED BY 90° C. EXTRACT (COMPOSITION 2) (ng/g) | CONCENTRATION IN SEAWEED IMPLIED BY ETHANOL/WATER EXTRACT (CONTROL) (pmol/g) | CONCENTRATION IN SEAWEED IMPLIED BY ETHANOL/WATER EXTRACT (CONTROL) (ng/g) | CONCENTRATION IN *S. heterophyllum* (pmol/g) FROM KWAZULU-NATAL |
|---|---|---|---|---|---|---|---|
| AUXINS AND INDOLES | | | | | | | |
| indole-3-acetic acid (IAA) | | | 12284 ± 1965 | 2152 ± 344 | | | |
| indole-3-acetic acid ethyl ester | | | 1.8 ± 0.3 | 0.36 ± 0.06 | 0.9 ± 0.2 | 0.18 ± 0.03 | |
| indole-3-acetyl-glycine (IAGly) | 9 ± 2 | 2.2 ± 0.4 | | | | | 3.6 ± 0.6 |
| indole-3-acetyl-L-alanine (IAAla) | | | 50 ± 0.2 | 12 ± 2 | 53 ± 9 | 13 ± 2 | |
| Indole-3-acetyl-L-aspartic acid | | | | | | | |
| Indole-3-acetyl-L-leucine (IALeu) | | | | | | | |
| Indole-3-acetyl-L-phenylalanine | | | | | | | |
| Indole-3-acetyl-L-valine (IAVal) | | | | | | | |
| indole-3-carboxylic acid (I3CA) | 536 ± 91 | 86 ± 15 | 4224 ± 718 | 681 ± 116 | 7480 ± 1272 | 1206 ± 205 | |
| indole-3-carboxylic acid methyl | 1.4 ± 0.24 | 0.24 ± 0.04 | 198 ± 34 | 35 ± 6 | 1.9 ± 0.3 | 0.34 ± 0.06 | |
| indole-3-propionic acid (IPA) | | | | | | | |
| indole-3-butyric acid (IBA) | | | 7556 ± 1058 | 1536 ± 215 | | | |
| indole-3-pyruvic acid (IPiA) | | | | | | | |
| indole-3-elyoxylic acid methyl ester | 7552 ± 830 | 1535 ± 169 | 1500 ± 165 | 305 ± 34 | 926 ± 102 | 188 ± 21 | |
| DL-indole-3-lactic acid (ILA) | | | 104 ± 16 | | 134 ± 20 | 28 ± 4 | |
| 5-fluoroindole (5FI) | | | | | | | |
| 4-chloroindole-3-acetic acid | | | | | | | |
| 4-chloroindole-3-acetic acid methyl | | | | | | | |
| 5-chloroindole-3-acetic acid | | | | | | | |
| 5-bromoindole-3-acetic acid | | | | | | | |
| indole-3-carboxaldehyde (IAld) | 264 ± 32 | 38 ± 5 | 2102 ± 252 | 305 ± 37 | 1175 ± 141 | 171 ± 20 | |
| indole-3-acetamide (IAM) | | | | | | | |
| tryptophol (IEt) | | | 1523 ± 259 | 245 ± 42 | 522 ± 89 | 84 ± 14 | |
| melatonin (M) [N-acetyl-5-methoxytryptamine] | | | | | | | |
| Total auxins | 8,362 ± 955 | 1,661 ± 189 | 29,542 ± 4468 | 5,259 ± 796 | 10,308 ± 1636 | 1,694 ± 267 | |
| CYTOKININS-ISOPRENOID | | | | | | | |
| N6-isopentenyladenine (iP) | | | 206 ± 19 | 42 ± 4 | 101 ± 9 | 21 ± 2 | 48 ± 5 |
| N6-isopentenyladenosine (iPR) | 7 ± 2 | | | | | | |
| trans-zeatin (tZ) | 2.4 ± 0.8 | | | | | | |
| trans-zeatin riboside (tZR) | | | | | | | |
| trans-zeatin-9-glucoside (tZ9G) | | | | | | | |
| trans-zeatin-O-glucoside (tZOG) | 16 ± 3 | | | | | | |
| trans-zeatin riboside-O-glucoside | | | | | | | |
| cis-zeatin (cZ) | 43 ± 6 | 9 ± 1 | 32 ± 4 | 7.1 ± 0.9 | 73 ± 10 | 16 ± 2 | 11 ± 2 |
| cis-zeatin riboside (cZR) | | | | | | | 0.6 ± 0.1 |
| cis-zeatin-O-glucoside (cZOG) | | | | | | | 1.0 ± 0.3 |
| cis-zeatin riboside-O-glucoside | | | | | | | 1.1 ± 0.2 |
| dihydrozeatin (DHZ) | | | | | | | |
| dihydrozeatin riboside (DHZR) | | | | | | | |
| Dihydrozeatin-O-glucoside (DHZOG) | | | | | | | |
| dihydrozeatin riboside-O-glucoside | | | | | | | |
| CYTOKININS-AROMATIC | | | | | | | |
| N6-benzyladenine (BA) | | | 0.04 ± 0.00 | 0.01 ± 0.00 | 0.44 ± 0.04 | 0.10 ± 0.01 | 0.6 ± 0.1 |
| N6-benzyladenosine (BAR) | | | | | | | |
| ortho-topolin (oT) | | | | 198 ± 0.26 | 48 ± 6 | | 2.9 ± 0.7 |
| ortho-topolin riboside (oTR) | | | | | | | |

TABLE 1-continued

Concentration of growth hormones in seaweed.

| HORMONE | CONCENTRATION IN SEAWEED IMPLIED BY ROOM TEMPERATURE EXTRACT (COMPOSITION 1) (pmol/g) | CONCENTRATION IN SEAWEED IMPLIED BY ROOM TEMPERATURE EXTRACT (COMPOSITION 1) (ng/g) | CONCENTRATION IN SEAWEED IMPLIED BY 90° C. EXTRACT (COMPOSITION 2) (pmol/g) | CONCENTRATION IN SEAWEED IMPLIED BY 90° C. EXTRACT (COMPOSITION 2) (ng/g) | CONCENTRATION IN SEAWEED IMPLIED BY ETHANOL/WATER EXTRACT (CONTROL) (pmol/g) | CONCENTRATION IN SEAWEED IMPLIED BY ETHANOL/WATER EXTRACT (CONTROL) (ng/g) | CONCENTRATION IN S. heterophyllum (pmol/g) FROM KWAZULU-NATAL |
|---|---|---|---|---|---|---|---|
| ortho-topolin-O-glucoside (oTOG) | | | | | | | 0.1 ± 0.1 |
| ortho-topolin riboside-O-glucoside | | | | | | | |
| meta-topolin (mT) | | | | | | | 1.7 ± 0.5 |
| meta-topolin riboside(mTR) | | | | | | | |
| meta-topolin-O-glucoside | | | | | | | 2.9 ± 0.6 |
| para-topolin (pT) | 1.1 ± 0.2 | 0.25 ± 0.05 | 677 ± 122 | 163 ± 29 | 6 ± 1 | 1.3 ± 0.2 | |
| para-topolin riboside (pTR) | | | | | | | |
| ortho-methoxytopolin (MeoT) | | | | | | | |
| meta-methoxytopolin (MemT) | | | | | | | |
| para-methoxytopolin (MepT) | | | | | | | |
| kinetin (K) | | | | | | | |
| kinetin riboside (KR) | | | | | | | |
| Total cytokinins | 44 ± 6 | 9 ± 1 | 915 ± 145 | 212 ± 34 | 378 ± 20 | 86 ± 10 | 95 ± 13 |
| GIBBERELLINS | | | | | | | |
| gibberellin A3 (GA3) | 8.3 ± 1.5 | 2.9 ± 0.5 | | | 9 ± 2 | 3.2 ± 0.6 | |
| gibberellin A6 (GA6) | 0.32 ± 0.07 | 0.11 ± 0.02 | | | 113 ± 25 | 39 ± 9 | |
| gibberellin A7 (GA7) | 0.73 ± 0.005 | 0.24 ± 0.02 | 0.66 ± 0.05 | 0.22 ± 0.02 | 16 ± 1 | 5.2 ± 0.4 | |
| Total gibberellins | 9.4 ± 1.6 | 3.3 ± 0.5 | 0.66 ± 0.05 | 0.22 ± 0.02 | 138 ± 28 | 47 ± 10 | |
| SALICYLATES | | | | | | | |
| salicylic acid (SA) | 346 ± 62 | 48 ± 9 | 4.0 ± 0.7 | 0.6 ± 0.1 | 2163 ± 389 | 299 ± 54 | |
| ABSCISIC ACIDS | | | | | | | |
| (+)-cis,trans-abscisic acid (ABA) | 46 ± 12 | 12 ± 3 | 49 ± 13 | 13 ± 4 | | | |
| JASMONATES | | | | | | | |
| (−)-jasmonic acid (JA) | | | 45 ± 10 | 10 ± 2 | 305 ± 67 | 64 ± 14 | |
| (−)-jasmonic acid methyl ester | 523 ± 68 | 117 ± 15 | 24 ± 3 | 5.4 ± 0.7 | 50 ± 6 | 11 ± 1 | |
| Total jasmonates | 523 ± 68 | 117 ± 15 | 69 ± 13 | 15 ± 3 | 355 ± 73 | 75 ± 15 | |

TABLE 2

Concentration of growth hormones in Composition 1 and Composition 2, and comparison with commercial compositions.

| HORMONE | CONCENTRATION IN ROOM TEMPERATURE EXTRACT (ng/mL) (COMPOSITION 1) | CONCENTRATION IN 90° C. EXTRACT (ng/mL) (COMPOSITION 2) | CONCENTRATION IN KELPAK® (ng/mL)[a] | CONCENTRATION IN SEASOL (ng/mL)[b] | CONCENTRATION IN KELPRO (BARMAC) (ng/mL)[c] | CONCENTRATION IN MAXICROP (ng/g)[d] |
|---|---|---|---|---|---|---|
| AUXINS AND INDOLES | | | | | | |
| indole-3-acetic acid (IAA) | | 215 ± 34 | 2.0 ± 0.6 | 154 | 2,900 | 500,000 |
| indole-3-acetic acid ethyl ester (IAAEt) | | 0.036 ± 0.006 | | | | |
| indole-3-acetyl-glycine (IAGly) | 0.22 ± 0.04 | | 1.0 ± 0.3 | | | |
| indole-3-acetyl-L-alanine (IAAla) | | 1.2 ± 0.2 | 0.06 ± 0.01 | | | |
| Indole-3-acetyl-L-aspartic acid (IAAsp) | | | 2.2 ± 0.8 | | | |
| Indole-3-acetyl-L-leucine (IAleu) | | | 0.087 ± 0.01 | | | |
| Indole-3-acetyl-L-phenylalanine (IAPhe) | | | | | | |
| Indole-3-acetyl-L-valine (IAVal) | | | | | | |
| [indole-3-carboxylic acid (I3CA)] | 8.6 ± 1.5 | 68 ± 12 | | | | |
| [indole-3-carboxylic acid methyl ester (I3CAMe)] | 0.025 ± 0.004 | 3.5 ± 0.6 | | | | |
| indole-3-propionic acid (IPA) | | | 0.4 ± 0.2 | | 157,000 | |
| indole-3-butyric acid (IBA) | | 154 ± 22 | | | | |
| indole-3-pyruvic acid (IPiA) | | | 1.2 ± 0.2 | | | |

TABLE 2-continued

Concentration of growth hormones in Composition 1 and Composition 2, and comparison with commercial compositions.

| HORMONE | CONCENTRATION IN ROOM TEMPERATURE EXTRACT (ng/mL) (COMPOSITION 1) | CONCENTRATION IN 90° C. EXTRACT (ng/mL) (COMPOSITION 2) | CONCENTRATION IN KELPAK ® (ng/mL)[a] | CONCENTRATION IN SEASOL (ng/mL)[b] | CONCENTRATION IN KELPRO (BARMAC) (ng/mL)[c] | CONCENTRATION IN MAXICROP (ng/g)[d] |
|---|---|---|---|---|---|---|
| indole-3-glyoxylic acid methyl ester (IGAMe) | 153 ± 17 | 31 ± 3 | | | | |
| DL-indole-3-lactic acid (ILA) | | 2.1 ± 0.3 | 0.28 ± 0.07 | | | |
| 5-fluoroindole (5FI) | | | | | | |
| 4-chloroindole-3-acetic acid (4ClIAA) | | | | | | |
| 4-chloroindole-3-acetic acid methyl ester (4ClIAAMe) | | | | | | |
| 5-chloroindole-3-acetic acid (5ClIAA) | | | | | | |
| 5-bromoindole-3-acetic acid (5BrIAA) | | | | | | |
| indole-3-carboxaldehyde (IAld) | 3.8 ± 0.5 | 30 ± 4 | | | | |
| indole-3-acetamide (IAM) | | | | | | |
| tryptophol (IEt) [3-(2-hydroxyethygindole] | | 25 ± 4 | | | | |
| melatonin (M) [N-acetyl-5-methoxytryptamine] | | | | | | |
| Total Auxins | 6[d] | 373[d] | 7.2 | 154 | 159,900 | 500,000 |
| CYTOKININS-ISOPRENOID | | | | | | |
| N6-isopentenyladenine (iP) | | 4.2 ± 0.4 | 0.04 ± 0.02 | 16 ± 2 | | |
| N6-isopentenyladenosine (iPR) (riboprine) | | | 0.007 ± 0 | 2 ± 1 | | |
| trans-zeatin (tZ) | | | 0.06 ± 0.03 | 0.7 ± 0.3 | 6,000 | |
| trans-zeatin riboside (tZR) | | | | 7 ± 1 | 13,000 | |
| trorts-zeatin-9-glucoside (tZ9G) | | | 0.015 ± 0 | | | |
| trans-zeatin-O-glucoside (tZOG) | | | 1.4 ± 0.3 | 15 | | |
| trans-zeatin riboside-O-glucoside (tZROG) | | | 0.005 ± 0 | <2.5 | | |
| cis-zeatin (cZ) | 0.9 ± 0.1 | 0.71 ± 0.09 | 0.002 ± 0 | | | |
| cis-zeatin riboside (all) | | | | | | |
| cis-zeatin-O-glucoside (cZOG) | | | 4 ± 0 | | | |
| dihydrozeatin (DHZ) | | | | 1.06 ± 0.02 | | |
| dihydrozeatin riboside (DHZR) | | | 0.004 ± 0 | 37 ± 3 | | |
| Dihydrozeatin-O-glucoside (DHZOG) | | | | 22 | | |
| dihydrozeatin riboside-O-glucoside (DHZROG) | | | 0.015 ± 0 | 13 | | |
| CYTOKININS-AROMATIC | | | | | | |
| N6-benzyladenine (BA) | | 0.0010 ± 0.00 | 0.05 ± 0.01 | | | |
| N6-benzyladenosine (BAR) | | | 0.011 ± 0 | | | |
| ortho-topolin (oT) | | | 0.04 ± 0.01 | | | |
| ortho-topolin riboside (oTR) | | | | | | |
| ortho-topolin riboside-O-glucoside (oTROG) | | | 0.011 ± 0 | | | |
| meta-topol in (mT) | | | 0.024 ± 0.007 | | | |
| meta-topolin riboside (mTR) | | | | | | |
| para-topolin (pT) | 0.025 ± 0.005 | 16 ± 3 | | | | |
| para-topolin riboside (pTR) | | | | | | |
| ortho-methoxytopolin (MeoT) | | | | | | |
| meta-methoxytopolin (MemT) | | | | | | |
| para-methoxytopolin (MepT) | <LOD | <LOD | ND | ND | ND | ND |
| kinetin (K) | | | | | | |
| kinetin riboside (KR) | | | | | | |
| Total cytokinins | 0.93 | 21 | 5.7 | 113-116 | 19,000 | |
| GIBBERELLINS | | | | | | |
| gibberellin A1 (GA1) | | | 0.00005 ± 0.00001[e] | | | |
| gibberellin A3 (GA3) | 0.29 ± 0.05 | | 0.00005 ± 0.00001 | | 51 | |
| gibberellin A4 (GA4) | | | 0.0017 ± 0.0005 | | | |
| gibberellin A6 (GA6) | 0.011 ± 0.002 | | 0.0006 ± 0.0002 | | | |
| gibberellin A7 (GA7) | 0.024 ± 0.002 | 0.022 ± 0.002 | 0.00005 ± 0.00001 | | | |
| Total gibberellins | 0.33 | 0.02 | 0.002(0.57) | | 51 | |
| SALICYLATES | | | | | | |
| salicylic acid (SA) | 4.8 ± 0.9 | 0.06 ± 0.01 | | | | |
| ABSCISIC ACIDS | | | | | | |
| (+)-cis,trans-abscisic acid (ABA) | 1.2 ± 0.3 | 1.3 ± 0.4 | 0.02070 ± 0.00004 | | | 200,000 |
| JASMONATES | | | | | | |
| (−)-jasmonic acid (JA) | | 1.0 ± 0.2 | | | | |
| (−)-jasmonic acid methyl ester (MeJA) | 12 ± 2 | 0.54 ± 0.07 | | | | |

TABLE 3

Activity of cytokinins in the tobacco callus bioassay (Matsubara 1990, Letham et al. 1983).

| HORMONE | MINIMUM CONCENTRATION ($\mu$M) | OPTIMUM CONCENTRATION ($\mu$M) |
|---|---|---|
| N6-isopentenyladenine (iP) | 0.0001 | 0.02 |
| N6-isopentenyladenosine (iPR) (riboprine) | 0.01 | 0.5 |
| trans-zeatin (tZ) | 0.0001 | 0.004-0.05 |
| trans-zeatin riboside (tZR) | 0.003 | 0.3 |
| trans-zeatin-9-glucoside (tZ9G) | >50 | |
| trans-zeatin-O-glucoside (tZOG) | 0.001 | |
| trans-zeatin riboside-O-glucoside (tZROG) | 0.003 | |
| cis-zeatin (cZ) | 0.03 | 0.5 |
| cis-zeatin riboside (cZR) | 0.03 | 0.3 |
| dihydrozeatin (DHZ) | 0.01 | 0.4 |
| dihydrozeatin riboside (DHZR) | 0.01 | 4 |
| Dihydrozeatin-O-glucoside (DHZOG) | 0.001 | |
| dihydrozeatin riboside-O-glucoside (DHZROG) | 0.002 | |
| N6-benzyladenine (BA) | 0.0008 | 0.07 |
| N6-benzyladenosine (BAR) | 0.02 | 1 |
| kinetin (K) | 0.001 | 0.1 |

TABLE 4 trans-Zeatin equivalents in Composition 1 and Composition 2 based on Tobacco callus/*P. lunatus* callus bioassay.

| CYTOKININ | nM in tZ EQUIVALENTS IN ROOM TEMPERATURE EXTRACT (COMPOSITION 1) | nM in tZ EQUIVALENTS IN 90° C. EXTRACT (COMPOSITION 2) | nM in tZ EQUIVALENTS IN KELPAK |
|---|---|---|---|
| N6-isopentenyladenine (iP) | | 4.2 | 0.042 |
| N6-isopentenyladenosine (iPR) (riboprine) | | | 0.0002 |
| trans-zeatin (tZ) | | | 0.29 |
| trans-zeatin-O-glucoside (tZOG)[a] | | | 3.6 |
| trans-zeatin riboside-O-glucoside (tZROG)[a] | | | 0.0005 |
| cis-zeatin (cZ) | 0.03 | 0.03 | 0.00008 |
| dihydrozeatin riboside (DHZR) | | | 0.00001 |
| dihydrozeatin riboside-O-glucoside (DHZROG)[a] | | | 0.00003 |
| N6-benzyladenine (BA) | | 0.0002 | 0.01 |
| N6-benzyladenosine (BAR) | | | 0.0001 |
| ortho-topolin (oT) | | | 0.002 |
| para-topolin (pT) | 0.0001 | 0.09 | |
| total | 0.03 | 4.3 | 3.9 |

TABLE 5

Ratio of M to G in some commercial alginates.

| SPECIES | M/G |
|---|---|
| *Sphacelaria bipinnata* | 0.4 |
| *Laminaria hyperborea* (stipes) | 0.37-0.65 |
| *Desmarestia aculeata* | 0.58 |
| *Pylaiella* | 0.6 |
| *Chordaria flagelhformis* | 0.63 |
| *Dictyosiphon lomentaria* | 0.9 |
| *Dictyota dichotoma* | 1.05 |
| *Fucus serratus* | 1.06 |
| *Ascophyllum nodosum* | 1.0-1.85 |
| *Laminaria digitata* | 1.16-1.63 |
| *Laminaria hyperborea* (fronds) | 1.28-1.35 |
| *Pelvetia canaliculata* | 1.28 |
| *Macrocystis pyrifera* | 1.56 |
| *Ecklonia cava* and *Eisenia bicyclis* | 1.6 |
| *Laminaria longicruris* | 2.03 |

TABLE 6

Treatment types for assessment of effect of composition application on lettuce yield.

| Treatment No. | Treatment Name | Rate | Treatment Description |
|---|---|---|---|
| 1. | Seaweed Extract 1 | 50 ml/liter | Application of Seaweed Extract in the nursery Foliar application at 5 days after transplanting |
| 2. | Seaweed Extract 2 | 100 ml/liter | Application of Seaweed Extract in the nursery |

TABLE 6-continued

Treatment types for assessment of effect of composition application on lettuce yield.

| Treatment No. | Treatment Name | Rate | Treatment Description |
|---|---|---|---|
| 3. | Seaweed Extract 3 | 150 ml/liter | Application of Seaweed Extract in the nursery Foliar application at 5 days after transplanting |
| 4. | Seaweed Extract 4 | 200 ml/liter | Application of Seaweed Extract in the nursery Foliar application at 5 days after transplanting |
| 5. | Seaweed Extract 5 | 250 ml/liter | Application of Seaweed Extract in the nursery Foliar application at 5 days after transplanting |
| 6. | Conventional (Control) | 0.75 g of UREA, 0.35 g of MAP and 0.86 g of Potassium nitrate per liter stock solution. NPK 13:13:20 | Application of stock solution daily for one week Application of NPK 5 days after transplanting |
| 7. | Untreated | 0 ml/liter | |

TABLE 7

Effect of treatment as per Table 6 on lettuce yield.

| Treatment | Plant + Root Weight(kg) | Root weight (kg) | Plant weight without roots (Kg) |
|---|---|---|---|
| T1 | 2.83 | 0.11 | 2.73 |
| T2 | 2.53 | 0.11 | 2.42 |
| T3 | 2.71 | 0.11 | 2.60 |
| T4 | 3.36 | 0.13 | 3.24 |
| T5 | 3.38 | 0.13 | 3.26 |
| T6 | 3.00 | 0.11 | 2.90 |
| T7 | 3.18 | 0.13 | 3.05 |

The invention claimed is:

1. A composition for stimulating growth of a plant comprising:
(a) para-topolin and one or more other plant hormones; and
(b) fucoidan and one or more other acidic polysaccharides, wherein the composition is about 1 in 6 to 1 in 2 dilution of an extract of brown seaweed of the species *Sargassum wightii*, which is extracted from the seaweed of between about 20% and about 80% dry with boiling water at a ratio of 10 L water per 1 kg seaweed (fresh weight) at suitable temperature for suitable time period, followed by removing solid seaweed material to obtain the extract.

2. The composition of claim 1, wherein the one or more other plant hormones are selected from the group consisting of an auxin; a cytokinin; a phenolic plant hormone; an isoprenoid plant hormone; an aromatic plant hormone; a lipid plant hormone, a gibberellin and a salicylate, or analogues or derivatives thereof.

3. The composition of claim 2, wherein the auxin is selected from the group consisting of indole-3-acetic acid (IAA); indole-3-acetic acid ethyl ester; indole-3-acetyl-glycine (IAGly); indole-3-acetyl-L-alanine (IAAla); indole-3-carboxylic acid (I3CA); indole-3-carboxylic acid methyl ester; indole-3-butyric acid (IBA); indole-3-glyoxylic acid methyl ester; DL-indole-3-lactic acid (ILA); indole-3-carboxaldehyde (IAld); and tryptophol (IEt).

4. The composition of claim 2, wherein the isoprenoid plant hormone includes an abscisic acid and/or an isoprenoid cytokinin.

5. The composition of claim 4, wherein the abscisic acid includes (+)-cis,trans-abscisic acid (ABA).

6. The composition of claim 2, wherein the aromatic plant hormone includes an aromatic cytokinin.

7. The composition of claim 2, wherein the lipid plant hormone is or includes a jasmonate.

8. The composition of claim 2, wherein the one or mere gibberellin is selected from the group consisting of gibberellin A3 (GA3); gibberellin A6 (GA6); and gibberellin A7 (GA7).

9. The composition of claim 2, wherein the salicylate is or includes salicylic acid.

10. The composition of claim 1, wherein the concentration of each of the para-topolin and the one or more other plant hormones in the composition is between about 0.01 parts per billion (ppb) by weight, and about 1 part per million (ppm) by weight, and/or the total concentration of the para-topolin and one or more other plant hormones in the composition is between about 1.5 ppb by weight and about 1.5 ppm by weight.

11. The composition of claim 2, wherein:
the total concentration of auxins in the composition is between about 1 and about 1 ppm by weight;
the total concentration of cytokinins in the composition is between about 0.1 and about 50 ppb by weight;
the total concentration of gibberellins in the composition is between about 0.005 and about 5 ppb by weight;
the total concentration of salicylates in the composition is between about 0.01 and about 20 ppb by weight;
the total concentration of abscisic acid in the composition is between about 0.1 and about 10 ppb by weight; and/or
the total concentration of jasmonate in the composition is between about 0.1 ppb and about 50 ppb by weight.

12. The composition of claim 1, wherein the one or more other acidic polysaccharides that are or include an alginate; an agar; and/or a carrageenan, or an analogue or derivative thereof.

13. The composition of claim 12, wherein the concentration of each of said fucoidan and said one or more other acidic polysaccharides in the composition is between about 50 ppm by weight to about 5 weight percent (wt. %), and/or the total concentration of said fucoidan and said one or more other acidic polysaccharides in the composition is between about 0.1 wt. % to about 10 wt. %.

14. The composition of claim 12, wherein the concentration of alginate in the composition is between about 0.1 wt. % and about 5 wt. %, and/or the concentration of fucoidan in the composition is between about 50 ppm to about 5000 ppm by weight.

15. A method of producing the composition of claim 1, the method including the step of obtaining an extract from a brown seaweed of the species *Sargassum wightii*, which is extracted from the seaweed of between about 20% and about 80% dry with boiling water at a ratio of 10 L water per 1 kg seaweed (fresh weight) at suitable temperature for suitable time period, followed by removing solid seaweed material to obtain the extract and dilution of the extract to obtain the composition.

16. The method of claim 15, wherein the seaweed is washed with water prior to obtaining the extract.

17. The method of claim 15, wherein obtaining the seaweed extract includes the step of boiling the seaweed in water at a temperature of between about 80° C. and about 130° C. at elevated pressure between about 2 atm and about 20 atm.

18. A method of stimulating the growth of a plant, the method including the step of applying the composition of claim 1 to the plant, to thereby stimulate the growth of the plant.

19. The method of claim 18, including the step of diluting the composition about 1 in 5 or 1 in 2 by volume prior to application to the plant.

20. The composition of claim 6, wherein the aromatic cytokinin is selected from the group consisting of N6-benzyladenine (BA) and ortho-topolin (oT).

21. The composition of claim 7, wherein the jasmonate is (−)-jasmonic acid (JA) or (−)-jasmonic acid methyl ester.

22. The composition of claim 4, wherein the isoprenoid cytokinin is N6-isopentenyladenine (iP) or cis-zeatin (cZ).

23. The composition of claim 1, wherein the composition is a liquid.

24. The composition of claim 1, wherein the composition is a solid.

25. The composition of claim 1, where the composition further comprises an additive selected from the group consisting of urea, ammonium nitrate, calcium nitrate, ammonium sulphate, diammonium phosphate, monoammonium phosphate, triple super phosphate, potassium nitrate, and potassium chloride.

* * * * *

UNITED STATES PATENT AND TRADEMARK OFFICE
CERTIFICATE OF CORRECTION

| | |
|---|---|
| PATENT NO. | : 11,751,573 B2 |
| APPLICATION NO. | : 16/764919 |
| DATED | : September 12, 2023 |
| INVENTOR(S) | : Bernard Port-Louis and Benjamin Port-Louis |

It is certified that error appears in the above-identified patent and that said Letters Patent is hereby corrected as shown below:

In the Claims

In Claim 8, Column 48, Line 14: please delete "one or mere" and insert -- one or more --.

In Claim 12, Column 48, Line 43: please delete "that are or" and insert -- are or --.

Signed and Sealed this
Seventeenth Day of October, 2023

Katherine Kelly Vidal
*Director of the United States Patent and Trademark Office*